United States Patent
Basch et al.

(10) Patent No.: US 6,982,317 B2
(45) Date of Patent: Jan. 3, 2006

(54) C21 POLYPEPTIDE THAT MODULATES THE STABILITY OF TRANSCRIPTIONAL REGULATORY COMPLEXES REGULATING NUCLEAR HORMONE RECEPTOR ACTIVITY

(75) Inventors: Ross S. Basch, New York, NY (US); Xin-Min Zhang, Bronx, NY (US)

(73) Assignee: New York University, New York, NY (US)

( * ) Notice: Subject to any disclaimer, the term of this patent is extended or adjusted under 35 U.S.C. 154(b) by 647 days.

(21) Appl. No.: 09/987,701

(22) Filed: Nov. 15, 2001

(65) Prior Publication Data

US 2005/0119456 A1     Jun. 2, 2005

Related U.S. Application Data

(60) Provisional application No. 60/248,191, filed on Nov. 15, 2000.

(51) Int. Cl.
*C07K 14/47*     (2006.01)
*C07K 16/18*     (2006.01)

(52) U.S. Cl. .................. 530/350; 530/300; 530/324; 530/387.1; 530/388.1; 530/387.9

(58) Field of Classification Search ............... 530/300, 530/350, 324, 387.1, 388.1, 387.9
See application file for complete search history.

(56) References Cited

OTHER PUBLICATIONS

Bassi et al, American Journal of Human Genetics, May 4, 1999, vol. 64, pp. 1604-1616.*

* cited by examiner

*Primary Examiner*—Terry McKelvey
(74) *Attorney, Agent, or Firm*—Browdy and Neimark PLLC

(57) ABSTRACT

A gene in humans and mice, designated C21, encodes a family of proteins that play a role in transcriptional regulation. Two isoforms ($\alpha$ and $\beta$) produced by alternative splicing has been identified in humans. A transgenic model was created that shows that over-expression of C21 in mouse hematopoietic cells alters myeloid development and suggests that members of this family are involved in regulating stem cell differentiation. Over-expressing C21 in 3T3 fibroblasts increases their resistance to apoptotic stimuli. The C21 protein forms a complex with a class of molecules that plays a critical role in transcription, the co-repressors of nuclear hormone receptors.

7 Claims, 20 Drawing Sheets

```
   1  ccgggagggg ggagcggcgt tggaggccac cgtttccagc atcaacaaca
  51  gcaacttgtg attggcggtg accggatatt cagttgcaca tccccacatc
 101  aatgcactgc caatgggtta tatcctgtgt tgtgacctca tggtttaagt
 151  gggaataaag ATGAGTATAA GCAGTGATGA GGTCAACTTC TTGGTATATA
 201  GATACTTGCA AGAGTCAGGA TTTTCTCATT CAGCATTTAC CTTTGGTATA
 251  AAAAGCCATA TCAGTCAGTC CAATATAAAT GGTGCCCTCG TCCCACCCGC
 301  TGCATTGATT TCTATCATCC AGAAAGGTCT ACAGTATGTA GAAGCAGAAG
 351  TTAGTATTAA TGAGGATGGT ACCTTGTTTG ATGGTCGACC AATAGAGTCT
 401  CTGTCCCTGA TAGATGCCGT AATGCCTGAT GTAGTACAAA CAAGACAACA
 451  AGCTTATAGA GATAAGCTTG CACAGCAACA GGCAGCAGCT GCTGCAGCTG
 501  CCGCAGCTGC AGCCAGCCAA CAAGGATCTG CAAAAAATGG AGAAACACA
 551  GCAAATGGGG AGGAGAATGG AGCACATACT ATAGCAAATA ATCATACTGA
 601  TATGATGAA GTGGATGGGG ATGTTGAAAT CCTCCTAAT AAAGCTGTTG
 651  TGTTGCGGGG CCATGAATCT GAAGTTTTA TCTGTGCCTG GAACCCTGTT
 701  AGTGATCTCC TACCATCAGG GTCTGGAGAC TCAACAGCAA GAATATGGAA
 751  TCTTAGTGAG AACAGCACCA GTGGCTCTAC ACAGTTAGTA CTTAGACATT
 801  GTATACGAGA AGGAGGGCAA GATGTTCCGA GCAACAAGGA TGTCACATCT
 851  CTAGATTGGA ATAGTGAAGG TACACTTCTA GCAACTGGTT CCTATGATGG
 901  GTTTGCCAGA ATATGGACTA AAGATGGTAA CCTTGCTAGC ACCTTAGGGC
 951  AGCATAAAGG CCCTATATTT GCATTAAAAT GGAATAAGAA AGGAAATTTC
1001  ATCCTAAGTG CTGGAGTAGA CAAGACTACA ATTATTTGGG ACGCACATAC
1051  TGGTGAAGCC AAGCAACAGT TTCCTTTTCA TTCAGCACCA GCATTGGATG
1101  TTGATTGGCA GAGCAACAAC ACCTTTGCTT CTTGTAGTAC AGATATGTGC
1151  ATTCATGTCT GTAAATTAGG ACAAGACAGA CCTATTAAAA CATTCCAAGG
1201  ACATACGAAT GAAGTAAATG CTATCAAATG GGACCCAACT GGCAATCTCT
1251  TGGCCTCCTG TTCTGACGAC ATGACTTTAA AGATATGGAG TATGAAACAA
1301  GACAATTGTG TCCATGATTT GCAGCAACAT AATAAAGAAA TTTATACTAT
1351  CAAATGGAGT CCAACAGGAC CAGGACTAA TAATCCAAAT GCCAACCTTA
1401  TGTTAGCAAG TGCATCCTTT GATTCTACTG TTAGCTTATG GGATGTAGAC
1451  CGAGGATAT GCATCCATAC CTTGACAAAA CACCAAGAGC CTGTGTACAG
1501  TGTAGCTTTC AGTCCTGATG GCAGGTATCT GCCAAGTGGT TCTTTTGACA
1551  AATGTGTACA CATGTGGAAC ACGCAGACAG GTGCTCTAGT TCACAGCTAT
1601  AGGGAACAG GTGGAATATT TGAAGTTTGC TGGAATGCAG CAGGAGACAA
1651  AGTTGGAGCC AGTGCATCAG ATGGTTCAGT TTGTGTATTA GACCTTCGGA
1701  AATAGcgcta ctagttggaa gccatggacc gactatgaat gtgtacatag
1751  ccaaaatgag tgtccctgac ccatgtaatg ttatagtccc acttgaacca
1801  tggccagtcc aatacagcca aatctaaaag aaatatatac atacagtgta
1851  tataaacaaa attcacccct gaagatgaca gagttttgtc acagcttgtg
1901  aattctgttc accaagtgct ggaatctaat ctgctgtgcc cctaaaatag
```

FIG. 5A

```
1951  catttagaag ttttggatat gaaaaacaga agagagaaaa tatacattat
2001  aaaagcagta catacatgta ccagtttttg gatactaaat gacagccttg
2051  tttctccct. ttgaatcagc agacaccatg gattatattc ttttttttcc
2101  ttcagtagtg agcagtttgt atgtacagag aaaatggact tacaaaaact
2151  tgcagcagta gtttgttctt gctttaaaat ttcgtttttg gtttagatta
2201  tggatgcatg aagtaaggga gtgaatcagt ttcttgttta tattttttc
2251  accttttaaa caaaaaattc tttaaaatat tttaatgcat tctttgaag
2301  aggtagatgt ttggtacatt ttatggctcc cagagcatat attcagttgg
2351  tgcatgttgt ggaagggga attggaaatt aaatggaaaa cctatgactt
2401  tggtcctgtc aatctgtaag acacatcagt aaaaggtat tatgctctgt
2451  tggttttgtt ttttgtttt gctttttttt ttttttnctt ttttgttttt
2501  tggtgatgtg gcttaaatgc aatagtttct ttttgggac atatttctgc
2551  caattaaaga ctagaagggc acaacttttt ttttaattac catagagaag
2601  atacattaaa aaaaatcttc tgatgttttg tagccataac taaattatgg
2651  taaaaatgtg cactattgtg aaaaggagca acgtagtttt gggtttttg
2701  ttgtttgttt gttttgcttt gttttttaag agattaaaat gtttctggat
2751  aaggattagc ttctcgaagt gtccatcatt ctgtgtanaa gcttaaatat
2801  gtaatgtaac caaactccag tattaaaaat ctctcatgtt gtttcttta
2851  tacaaagcaa gataacggca tataacactg ccattacatg gcaaaatgtt
2901  tgctacctta gtttaaaaaa caatctcaaa caaaagactt gcttcaaggt
2951  gttttaaat agcagtgatt cagaatttt tttaatgaaa gtataattgc
3001  actaaccttc ttcctgctgc tctgattctg catttgtggt acttgtgact
3051  acgttttttc aaatatagat agatttaagc tgctaatttt ttttttttta
3101  gtaatcacta ctatatcatg tcttttactc tgtttataat atcaagtatt
3151  ttcttaaaga tatagatatt aaaccttgtg ctcatgcaac ttagagtaac
3201  atatacagac aaatgattgc atgaggccat gtttatatgt gtgactaata
3251  aggcttgtca tgattaacat aatccaggta tgtcatttct gaagagaata
3301  gtcatcaaat ttatatctcg aagattttaa ttaagggaat tgcttattgt
3351  ttgagcttag caaattaata acactatttc tgtcactaat tatttttgagg
3401  ccttttagta ctaaaatttt aacctgtgtt ctaagtagaa actgatttaa
3451  cccaagtaat gcagctttga ttgatttcag cattcgttgc tttgctattt
3501  ttacaaaaca gcattgattg aagcaagttt tggttttact aaggtagggt
3551  agcatttgct attggtaaag agaataaata cacttaattt cacaatacat
3601  tgttatatgt accccagttg ttgttagtgg ggactatgat actgtaataa
3651  tatttttaaa aatttacatc aagagaggca gtcattcacg atggttttgt
3701  gccagctctt tttagggttt tggatcacat tagagatatt tagaacatat
3751  taccctgtga cttacgtagg aaacctaata tgctgagtat ctggcacttg
3801  aattctgct tttattgctg gaggtccaca tgtgtggttg acctctgtta
3851  ttgtttaaaa aaaaaaaaaa aaaaaaaaaa aaaaa
```

C21 POLYPEPTIDE THAT MODULATES THE STABILITY OF TRANSCRIPTIONAL REGULATORY COMPLEXES REGULATING NUCLEAR HORMONE RECEPTOR ACTIVITY

CROSS-REFERENCE TO RELATED APPLICATION

The present application claims priority under 35 U.S.C. §119(e) from U.S. provisional application No. 60/248,191, filed Nov. 15, 2000, the entire contents of which are hereby incorporated by reference.

GOVERNMENT LICENSE RIGHTS

The experiments performed in this application were supported by the National Institutes of Health, Grant Nos. DK43376 and DK49895. The U.S. Government has a paid-up license in this invention and the right in limited circumstances to require the patent owner to license others on reasonable terms as provided for by the terms of Grant Nos. DK43376 and DK49895.

BACKGROUND OF THE INVENTION

1. Field of the Invention

The present invention relates to molecules that interact with proteins regulating the nuclear hormone receptor family of transcription factors.

2. Description of the Related Art

All of the cells of the lymphohematopoietic system can be generated from a single cell (Nowell et al, 1969; Spangrude et al, 1988; Capel et al, 1990; Jordan et al, 1990; Wu et al, 1968). This pluripotential hematopoietic stem cell (PHSC) is separated from the mature cells of the peripheral blood by a series of intermediate cells of increasingly restricted developmental potential (Hodgson et al, 1979; Magli et al, 1982; Eaves et al, 1992; Jones et al, 1990; Lansdorp et al, 1990). The most restricted are committed to a single lineage and have limited capacity for self-renewal. Recombinant growth factors and clonal culture systems have made it possible to identify and isolate some committed progenitors, but the more immature PHSC has proven more elusive. Neither the exact number of PHSC nor the process by which their number is maintained is known and human PHSCs have not been unambiguously identified (Orlic et al, 1994). Most human hematopoietic progenitors express the CD34 antigen on their surface and this marker has been used extensively to identify and isolate hematopoietic progenitors (Krause et al, 1996). A CD34+CD38− fraction, which constitutes 0.1% of freshly isolated bone marrow cells, contains most of the PHSC activity in normal marrow (Terstappen et al, 1991). PHSC are not undifferentiated cells, but are uniquely specialized cells, whose role is to provide progenitors for the various hematopoietic lineages in a demand-responsive manner, while protecting the stem cell pool from depletion. The molecular basis for this ability is not known but is under intense scrutiny.

Several approaches have been used to try to identify the genes whose products regulate the stem cell pool. Yang et al (1996) made an EST database for CD34+ cells by single pass sequencing of 402 clones from a directional library. Thirty-five percent of the sequences were from previously unknown genes but none of these were differentially expressed in PHSC. Graf et al (1995), using differential display to identify differences between $CD38^{HI}$ and $CD38^{LO}$ cells, identified one previously unidentified sequence ("345"), that was expressed at ~2.5 times higher concentration in the $CD38^{LO}$ population. The sequence contained no open reading frame and lacked a polyadenylation site. The pace of the search for hematopoietically relevant genes has quickened lately. Using a cDNA library prepared from CD34+ cord blood cells, close to 10,000 ESTs were identified (Mao et al, 1998). The majority of these were either known sequences (47.6%) or corresponded to previously catalogued ESTs (26.4%), but 14.3% were new ESTs. A retroviral gene trap vector that selects for integration in or near expressed 5' exons has also been used in an attempt to identify genes that were repressed during hematopoietic differentiation (Muth et al, 1998). Two genes, of unknown function, were identified but targeted deletions failed to show hematopoietic abnormalities.

In all living creatures, cells are continuously dying. They are either killed by injurious agents or they are induced to commit suicide. Cells that are damaged by injury, such as by mechanical damage, exposure to toxic chemicals, undergo a characteristic series of changes: they swell (because the ability of the plasma membrane to control the passage of ions and water is disrupted) and the cell contents leak out, eliciting an inflammatory response in the surrounding tissues. Cells that are induced to commit suicide shrink, have their mitochondria break down with the release of cytochrome c, develop bubble-like blebs on their surface and undergo DNA and chromatin fragmentation. Ultimately they break into small, membrane-wrapped, fragments which are engulfed by nearby phagocytic cells without causing inflammation. The pattern of events in death by suicide is called programmed cell death or apoptosis.

Programmed cell death is needed for remodeling of structures during development. Well-known examples include the resorption of the tadpole tail at the time of its metamorphosis into a frog; the formation of the fingers and toes of the fetus by removing (by apoptosis) the tissue between them, and the sloughing off of the inner lining of the uterus (the endometrium) at the start of menstruation.

Programmed cell death is also required to destroy cells that represent a threat to the integrity of the organism. In the immune system, some cell-mediated killing of virus-infected cells occurs by inducing apoptosis and, as cell-mediated immune responses wane, the effector cells are removed by an apoptotic mechanism. Defects in the apoptotic machinery are associated with autoimmune diseases, such as lupus erythematosus and rheumatoid arthritis.

Genetic damage can cause somatic cells to become malignant and lead to abnormal embryonic development (leading to birth defects). Cells respond to DNA damage by increasing their production of p53 which can induce apoptosis. Mutations in the p53 gene, producing a defective protein which does not induce apoptosis, are often found in cancer cells.

The decision to commit suicide depends on the balance between the positive signals needed for survival and signals initiating a death pathway (negative signals). The survival of many cells requires that they receive continuous stimulation from other cells and, for many, continued adhesion to the surface on which they are growing. In the absence of these positive signals, cells initiate a program leading to cell death. Cellular damage by increased levels of oxidants, damage to DNA by these oxidants or other agents like ultraviolet light, X-rays and some chemotherapeutic drugs, as well as agents that bind to specific receptors on the cell surface, also initiate the apoptosis program. These death activators include tumor necrosis factor (TNF) and lymphotoxin that both bind the TNF receptor; and Fas ligand (FasL), a molecule that binds to Fas (CD95).

Cells appear to use different pathways to initiate apoptosis depending on the source of the signal. In a healthy cell, the outer membranes of mitochondria, the endoplasmic reticulum (ER) and the nuclear envelope express the protein Bcl-2 on their surface. Bcl-2 binds a molecule of Apaf-1, which is itself bound to a molecule of caspase 9. Caspase 9 is one of a family of over a dozen caspases (cysteine-aspartate proteases). Internal damage in the cell results in release of cytochrome c from the mitochondria and causes Bcl-2 to release the heterodimer of Apaf-1 and caspase 9. These aggregate in the cytosol. Caspase 9 cleaves and, in so doing, activates other caspases. The sequential activation of one caspase by another creates an expanding cascade of proteolytic activity that leads to digestion of structural proteins in the cytoplasm degradation of chromosomal DNA and death of the cell.

Apoptosis can also be triggered by external signals. Fas and the TNF receptor are integral membrane proteins with their receptor domains exposed at the surface of the cell. Binding of the complementary death activator (FasL and TNF, respectively) transmits a signal to the cytoplasm that leads to activation of caspase 8. Caspase 8 (like caspase 9) initiates a cascade of caspase activation leading to cell death.

Several known proteins or families of proteins that function to regulate apoptosis include:

1. Members of the BCL-2 family. Some members of this family inhibit apoptosis, including Bcl-2 and Bcl-x. Others, such as BAX, stimulate apoptosis. BAX is thought to accomplish this by binding to and inhibiting the anti-apoptotic functions of Bcl-2 and Bcl-x.

2. FLAMES 1 and 2 are proteins that regulate cell death mediated by receptors of the TNF receptor family. TRAIL receptors are cell death receptors which are members of the TNF receptor family and exert cell suicide effects on cancerous but not normal cells.

3. IAP family members are homologous to the baculovirus IAPs. The open reading frames (ORFs) possess three baculoviral inhibition of apoptosis protein repeat (BIR) domains and a carboxy-terminal RING zinc-finger. The human IAP genes have a distinct but overlapping pattern of expression in fetal and adult tissues. These proteins significantly increase the number of known apoptotic suppressors. A fourth member of the family, termed survivin has also been identified. All appear to be caspase inhibitors.

IEX-IL is an nf-kB regulated survival factor, that protects cells from Fas or TNF induced apoptosis.

The nuclear hormone receptor (NHR) superfamily is a large family of mainly ligand-dependent transcription factors that play a role in the regulation of reproduction, growth, differentiation, and homeostasis. The family includes receptors for steroid hormones (estrogen, androgen, adrenal glucocorticoid, aldosterone, and progesterone), thyroid hormone and retinoic acid as well as a group of so-called "orphan receptors" that have poorly, defined ligand(s).

Members of the family share several structural features including a conserved DNA binding domain (DBD) that targets the receptor to specific DNA sequences which are called hormone response elements (HRE). The carboxyl-end of the receptor contains the ligand-binding domain (LBD) and embedded within this LBD is a hormone-dependent transcriptional activation domain. The LBD serves as a molecular switch that recruits co-activator or co-repressor proteins that regulate transcription of the target genes. Ligand-dependent receptors like the thyroid hormone receptor (T3R) and retinoic acid receptor (RAR) stimulate transcription when ligand is bound and repress it when the ligand is absent (Hu et al, 2000).

The best-characterized mammalian co-repressors are N-CoR (nuclear receptor co-repressor) (Chen et al, 1995) and SMRT (silencing mediator of retinoid and thyroid receptor) (Horlein et al, 1995). These co-repressors fill overlapping but non-redundant roles in regulating transcription. Both SMRT and N-CoR are large proteins (>170 kD) that exist in multi-protein complexes that have an estimated size of 1.5–2 mDa. A SMRT complex, isolated by a combination of conventional and immunoaffinity chromatography has been shown to contain histone deacetylase 3 (HDAC3) and transducin (beta)-like I (TBL1), a WD-40 repeat-containing protein (see below). The HDAC3-containing, SMRT and N-CoR complexes can bind to unliganded thyroid hormone receptors (T3Rs) in vitro (Li et al, 2000). Although both co-repressors are expressed widely, extensive hematological abnormalities including blocks in erythrocyte and T-cell development (Jepsen et al, 2000) follow targeted deletion of N-CoR.

Co-repressors mediate transcriptional silencing by inhibiting the basal transcription machinery or by recruiting chromatin-modifying enzymes (Hu et al, 2000; Li et al, 2000; Wong et al, 1998; Burke et al, 2000). Histone deacetylation, which produces a more compact chromatin structure that is inaccessible to transcriptional activators (Burke et al, 2000), appears to be the predominant means of chromatin modification. Studies of PAR and T3R show that ligand binding leads to the displacement of an HDAC-containing complex from the nuclear receptor in exchange for a histone acetyltransferase (HAT)-containing complex and this may serve as a general mechanism for switching nuclear receptors from a transcriptionally repressive to a transcriptionally active state (Xu et al, 1999). Transcriptional repression by N-CoR involves a co-repressor complex that contains one or more HDAC and may include mSin3A/B (Huang et al, 2000). Changes in repression correlate with alterations in the level of N-CoR and/or SMRT. These levels are regulated by both the rate of synthesis of the co-repressors and, more dramatically, by their rate of degradation. Targeted proteolysis of transcriptional co-regulators has been established as a mechanism for cell-specific regulation of gene transcription (Zhang et al, 1998a). Although the composition of the repressor complex is not fully understood a protein called TBL1 is present in some cells (Huang et al, 2000; Guenther et al, 1998) and in these cells, the extent of transcriptional repression was regulated by the amount of TBL1 present.

Citation of any document herein is not intended as an admission that such document is pertinent prior art, or considered material to the patentability of any claim of the present application. Any statement as to content or a date of any document is based on the information available to applicant at the time of filing and does not constitute an admission as to the correctness of such a statement.

SUMMARY OF THE INVENTION

The present inventor has discovered a gene in humans and in mice, designated C21, which encodes a family of proteins that play a role in transcriptional regulation. Two isoforms (α and β) produced by alternative splicing have been identified in humans. A transgenic model was created that shows that over-expression of C21 in mouse hematopoietic cells alters myeloid development and suggests that members of this family are involved in regulating stem cell differentiation. Over-expressing C21 in 3T3 fibroblasts increases their resistance to apoptotic stimuli. The C21 protein forms a complex with a class of molecules that plays a critical role in transcription, the co-repressors of the nuclear hormone receptors (NHR). These co-repressors mediate the down-regulation of gene expression. C21 binds to the co-repressors and appears to interfere with the ubiquitin-mediated proteolysis of the co-repressors, causing an elevation of the co-repressor concentration. Members of the family are expressed at high levels in fetal hematopoietic tissues as well as in many hematopoietic cell lines. Like many WD40 proteins, C21 family members appear to act by serving as an adaptor or bridge, facilitating the interaction of proteins that do not interact directly.

The present invention thus provides a C21 polypeptide, which interacts with, and has the activity of modulating the stability of, transcriptional regulatory complexes that regulate nuclear hormone receptor activity, and fragments of C21 polypeptide that retain this activity. Also comprehended by the polypeptide according to the present invention is a variant of the C21 polypeptide that has an amino acid sequence with at least 85% sequence identity to the C21 polypeptide of SEQ ID NO:2, and which interacts with, and also has the activity of modulating the stability of, transcriptional regulatory complexes that regulate nuclear hormone receptor activity.

The present invention further provides a molecule having the antigen-binding portion of an antibody specific for the polypeptide according to the present invention.

Other aspects of the present invention are directed to a nucleic acid molecule encoding the polypeptide, fragment or variant thereof, of the present invention, a vector containing this nucleic acid molecule, and a host cell transformed with the nucleic acid molecule.

BRIEF DESCRIPTION OF THE DRAWINGS

FIG. 1A is the starting BMC (3.2% CD34+). FIG. 1B is after removal of lineage positive cells (72% CD34+). FIG. 1C is sorted CD34+/CD38– cells (99% CD34+, 97% CD38–). FIG. 1D is sorted CD34+/CD38+ cells (96% CD34+, 98% CD38+).

FIGS. 2A (virtual Northern blots) and 2B (RT-PCR analysis) show differential expression of C12, C21, C23 and C40 by CD34+/CD38– and CD34+/CD38+ BMC. In the blots of FIG. 2A, double-stranded cDNAs amplified from total RNA obtained from the CD34+/CD38– and CD34+/CD38+ cells were used to demonstrate expression rather than conventional Northern blots because of the paucity of RNA available. The cDNAs were electrophoresed through a 1% agarose gel, transferred to nitrocellulose membranes and hybridized with C20, C12, C21, C23, C40 and β-actin probes respectively. The resultant autoradiographs were scanned and their digitized images are shown in the figure.

Figures 2A, 2B:
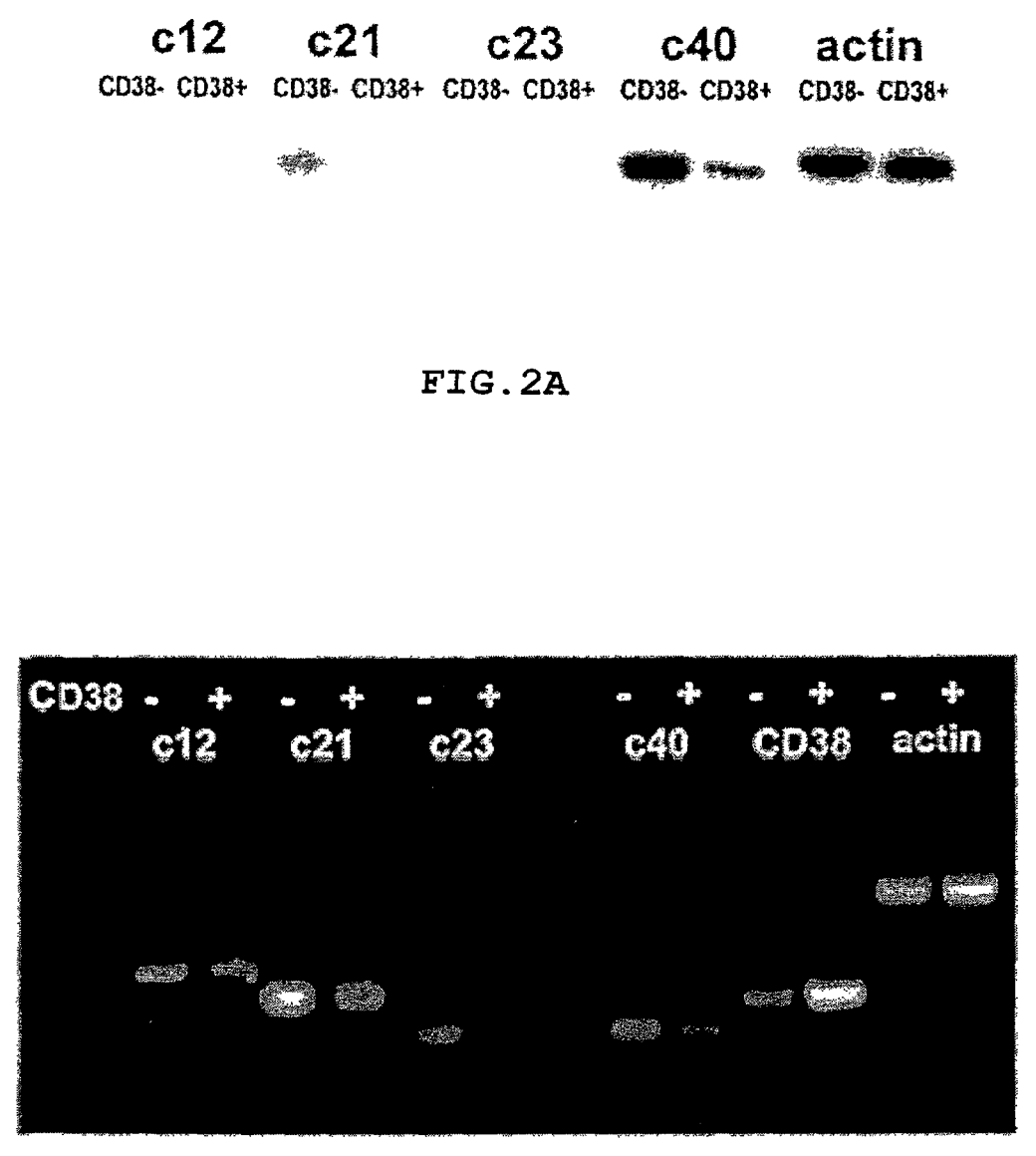

In the RT-PCR analysis of FIG. 2B, ethidium bromide stained agarose gel electrophoresis of reaction products are shown. Preparations from CD34+/CD38– and CD34+/CD38+ cells were placed in adjacent lanes and are labeled CD38– and CD38+. The RT-PCR was performed with total RNA extracted from ~35000 sorted, lineage negative CD34+/CD38– and CD34+/CD38+ BMC. Each sample was amplified with primers for C12, C21, C23 and C40 as well as primers that would amplify the cDNAs of CD38 and actin, which were included as controls. Each pair of lanes is labeled to indicate the primer pairs used in the amplification. Although the same number of CD38– and CD38+ cells were used for the RNA preparations, analysis of the photographic image indicates that there was ~1.8 times as much actin message in the CD34+/CD38+ sample than in the CD34+/CD38– sample. Despite this, all four cDNAs are more abundant in the reaction mixtures prepared from the CD34+/CD38– cells. CD38, as expected was more abundant in the CD34+/CD38+ cell population. The PCR was performed with specific primers selected to amplify fragments that could be distinguished from each other on the basis of the size of expected product (C12 (500 bp), C21(156 bp), C23 (151 bp) and C40 (192 bp)). Primers for actin (668 bp) and CD38 (236 bp) were synthesized from published sequences. The amplification was performed under the following conditions: 1 minute at 94° C. followed by 28 cycles of 30 seconds at 94° C., 30 seconds at 58° C. and 2 minutes at 72° C. with a final 10-minute extension at 72° C.

Figure 1A:
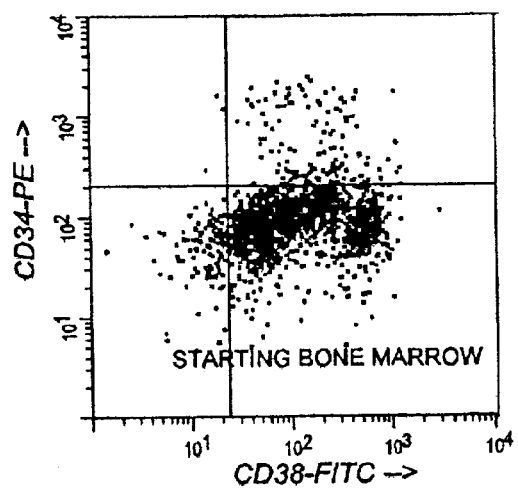
FIGS. 1A–1D are dot plots (two-dimensional histograms) illustrating the purification of CD34/+CD38– and CD34+/CD38+ cells from human bone marrow (BM). The abscissa represents the fluorescence intensity of the staining with anti-CD38 coupled to fluorescein and the ordinate the intensity of the staining with anti-CD34 coupled to phycoerythrin.
Figure 1B:
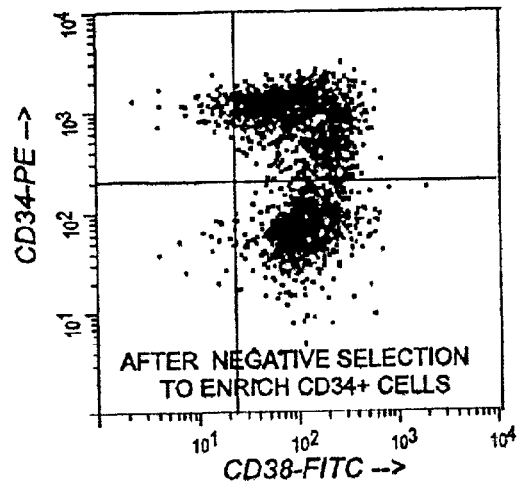
Figure 1C:
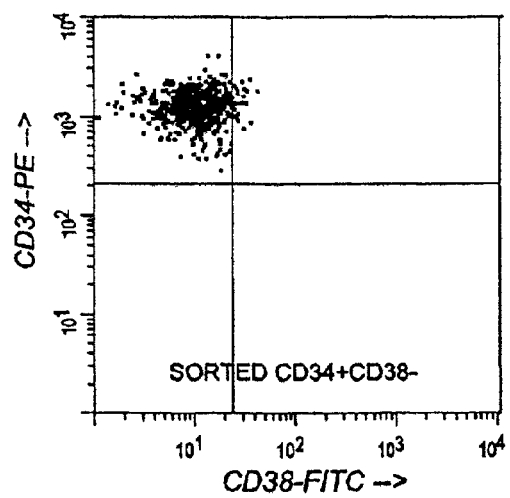
Figure 1D:
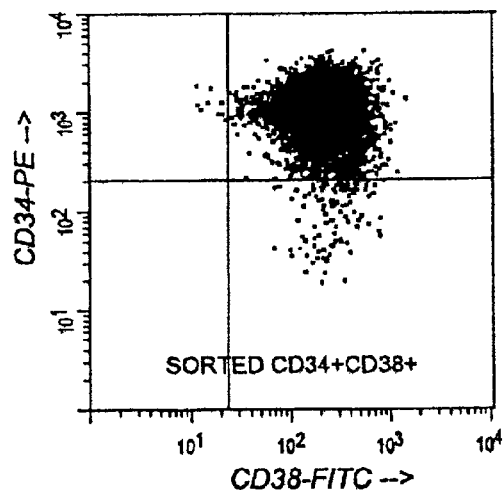
Figure 3A:
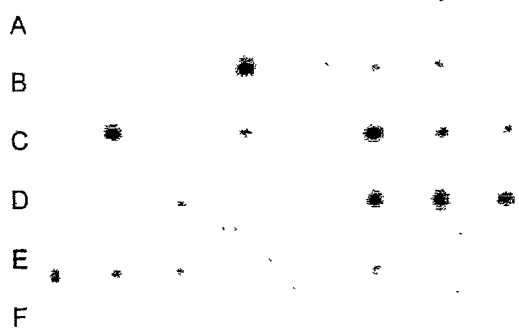
Figure 3B:
Figure 3C:
Figure 3D:

FIGS. 3A–3D show the expression of mRNA encoding C12, C21 and C23 by human tissues. Multiple tissues dot blots, purchased from Clontech, were hybridized with $^{32}$P-labeled probes. In each case the probe used was the original fragment cloned after the PCR-mediated subtractive hybridization. The same filter was used for all hybridizations. C23 was hybridized first (FIG. 3B), then C21 (FIG. 3C) and finally C12 (FIG. 3D). Between hybridizations the bound radioactive probes were stripped and the filter exposed to fresh film to assure that the stripping had been complete. The template shown in FIG. 3A identifies the source of the RNA in each position. The autoradiographs were scanned to produce the images shown. The signals obtained with the three neural tissues RNA were cut from the original image and moved to the row D, positions 6, 7 and 8.

Figure 4A:
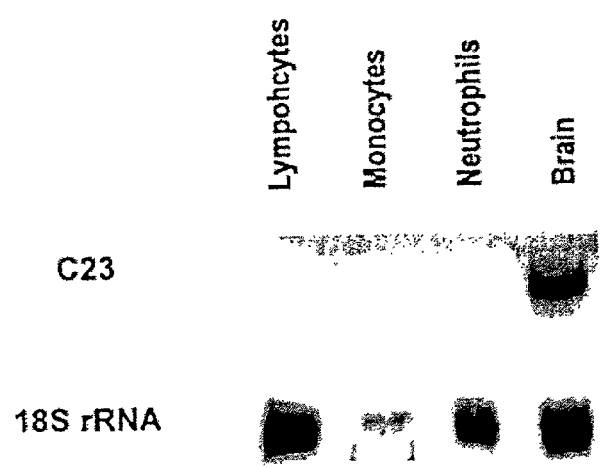
Figures 4B, 4C:
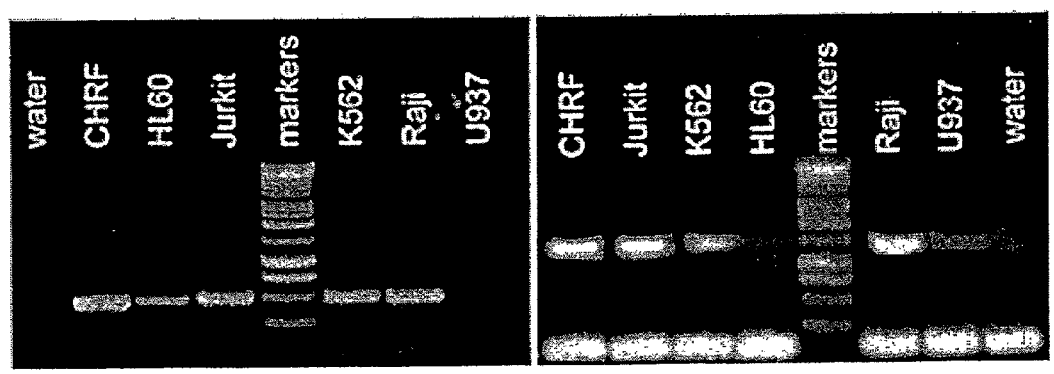

FIGS. 4A–4C show the expression of C23, C21 and C12 mRNA by hematopoietic cells. FIG. 4A shows the expression of C23 mRNA by peripheral white cells. Digital reproduction of an autoradiograph showing the results of an RNAse protection assay (RPA) to detect the expression of a message that included the far 3' end of the 3' UTR. Lymphocytes, monocytes and polymorphonuclear leukocytes were isolated by flow cytometry from human peripheral blood based on their light scatter properties. Total RNA from human brain was used as positive control for C23. 18s rRNA was used as an internal control to normalize the amount of RNA added to each lane of the gel. In FIGS. 4B and 4C, the expression of C21 and C12 mRNA by human leukemic cell lines is shown. Digital reproduction of autoradiographs show the results of RT-PCR amplification of the ORF (1548 bp) of C21 (FIG. 4B) and a 500 bp fragment of C12 (FIG. 4C) in RNA extracted from human leukemic cell lines. In each case a single band of the appropriate molecular mass was detected.

FIGS. 5A–5B show the sequence of the cDNA (SEQ ID NO:1) encoding C21. The open reading frame is indicated in CAPITOL letters. The WD-sequence regions are shaded, and the potential phosphorylation site sequence is underlined.

Figure 6:
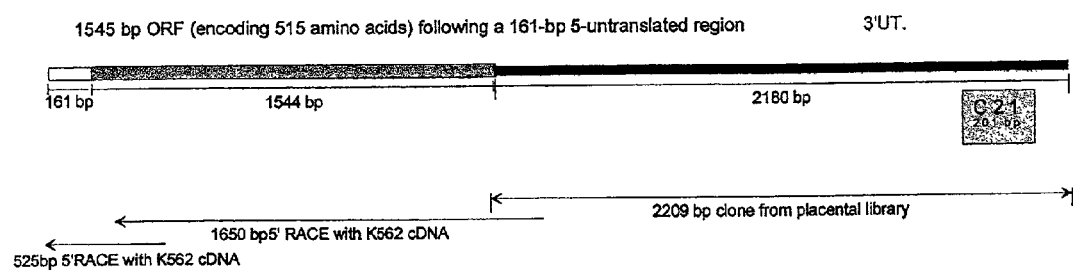

FIG. 6 is a schematic illustration of the strategy for cloning C21 cDNA. A human placental cDNA library was screened by PCR with primers from the original C21 sequence shown in the shaded box. The isolated clone (2180 bp) contained the entire 3' UTR shown in the solid black line. Sequential 5' RACE, using K562 double stranded cDNA as a template, revealed the 1545 bp ORF, indicated by the shaded line in the figure preceded by the 161 bp 5' UTR, indicated by the unshaded line.

Figure 7:
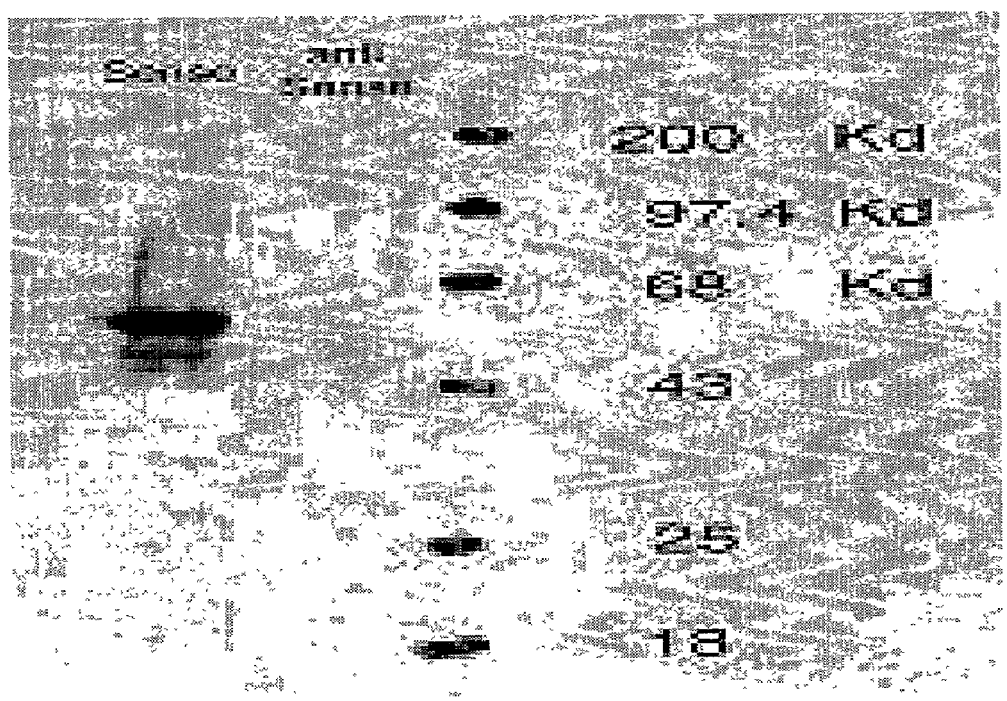

FIG. 7 shows the in vitro translation of the ORF of C21 mRNA. The ORF was amplified using a 5' primer that began with the ATG start codon and a modified 3' primer that included a c-myc tag. The PCR product was ligated into PCR3.1 under the control of the T7 promoter. The vector was linearized with EcoRI, and mRNA was synthesized using T7 RNA polymerase. This mRNA was used to support in vitro translation by a rabbit reticulocyte system which incorporated biotin labeled-lysine. The product was detected with streptavidin-horse radish peroxidase (HRP) and a chemiluminescent detection system (ECL). Both sense and antisense messages were used to prime the translation system.

FIGS. 8A–8D show Western blotting with anti-peptide antibodies made against deduced sequences from C21 α and β. After transfer, the membranes were stained with polyclonal rabbit anti-C21 peptide antibodies and the transferred proteins visualized with HRP-labeled donkey anti-rabbit IgG. The bound HRP was detected using luminol as the substrate.

Figures 9A, 9B:
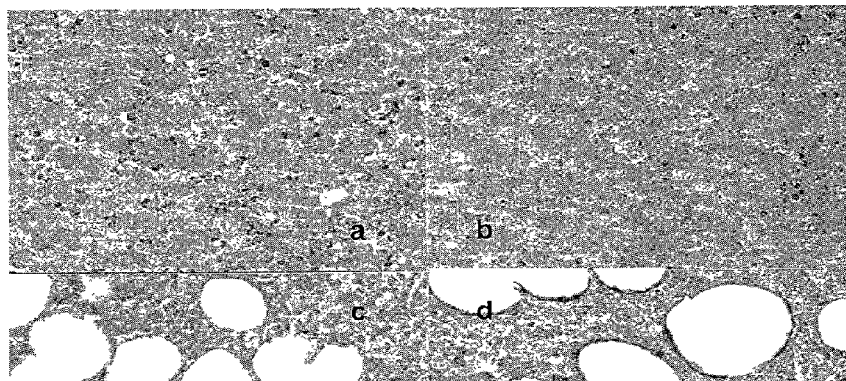
Figures 9C, 9D:
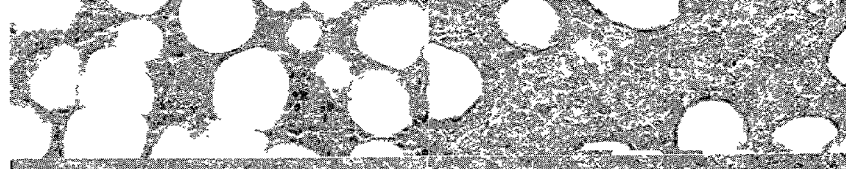
Figures 9E, 9F:
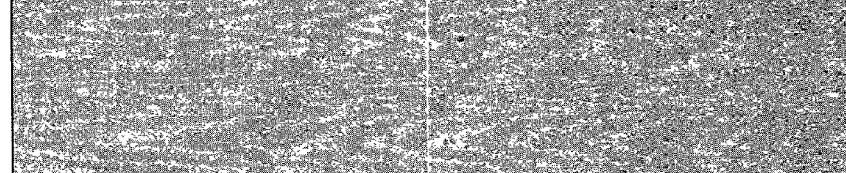
Figures 9G, 9H:
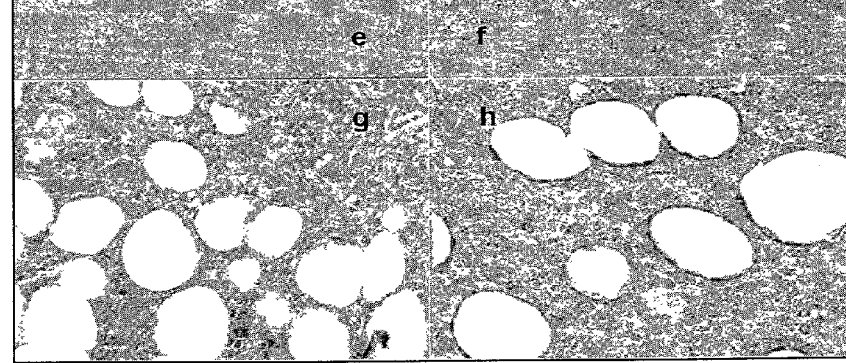

FIGS. 9A–9H show that C21 is expressed by hematopoietic progenitors in fetal liver and adult marrow. FIG. 9A is C21α vs 17 Week Fetal Liver. FIG. 9B is C21β vs 17 Week Fetal Liver. FIG. 9C is C21α vs Adult Bone Marrow. FIG. 9D is C21β vs Adult Bone Marrow. FIGS. 9E–9H are the same tissues (1–2 sections above or below) stained with pre-immune rabbit serum. Original Magnification is 40×. Stained with HRP coupled goat anti-rabbit IgG. AEC chromagen. Counter stained with Haematoxylin.

Figure 10:
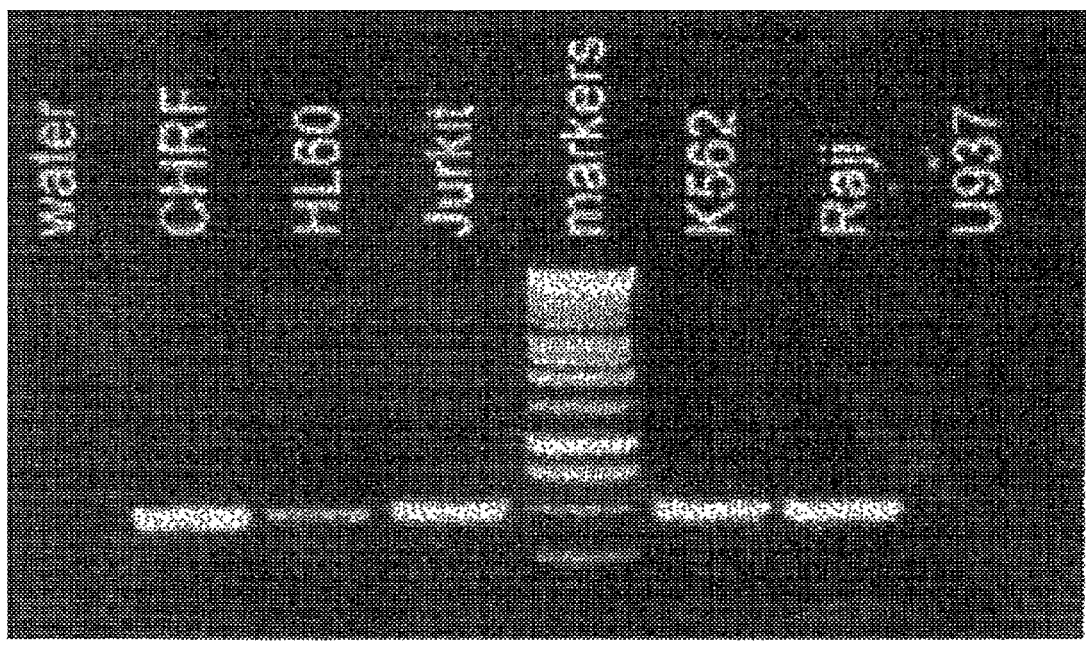

FIG. 10 is an agarose gel showing C21 mRNA expression by hematopoietic tumor cell lines. RT-PCR was used to examine the expression of C21. The primers used amplified only the a isoform and produced a 1546 bp fragment.

Figure 11:
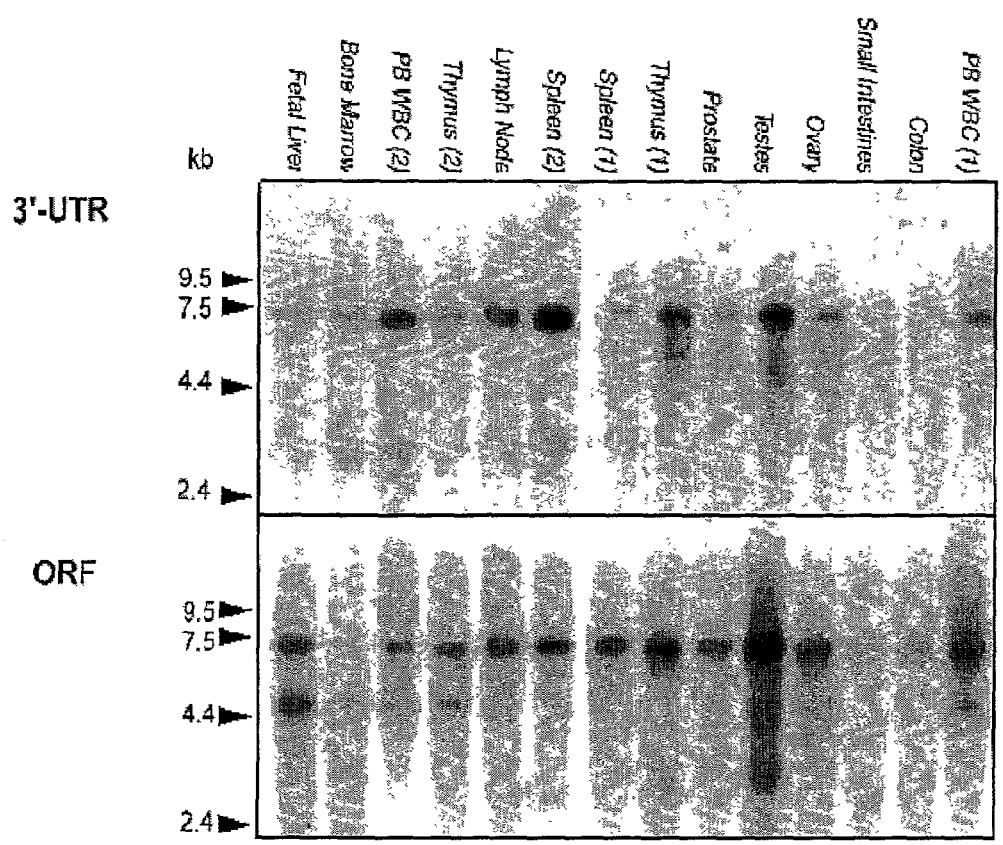

FIG. 11 shows Northern blots of human tissue RNA with either the 3' UTR or ORF of C21α as a $^{32}$P-labeled probe.

Figure 12A:
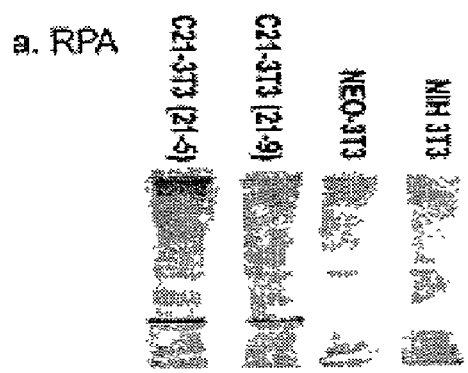
Figure 12B:
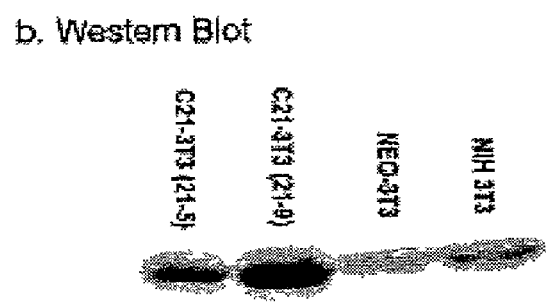

FIGS. 12A and 12B show the expression of hC21 in mouse fibroblasts in ribonuclease proteation assay (RPA; FIG. 12A) and Western blot (FIG. 12B). The cDNA encoding the ORF of hC21α was amplified by PCR, and the product ligated in the sense configuration into pcDNA3.1. After transformation of the appropriate E. coli, the plasmids were isolated and used to transfect NIH3T3 cells using lipofectamine. G418 resistant clones were selected and analyzed for their expression of C21.

Figures 13A, 13B:
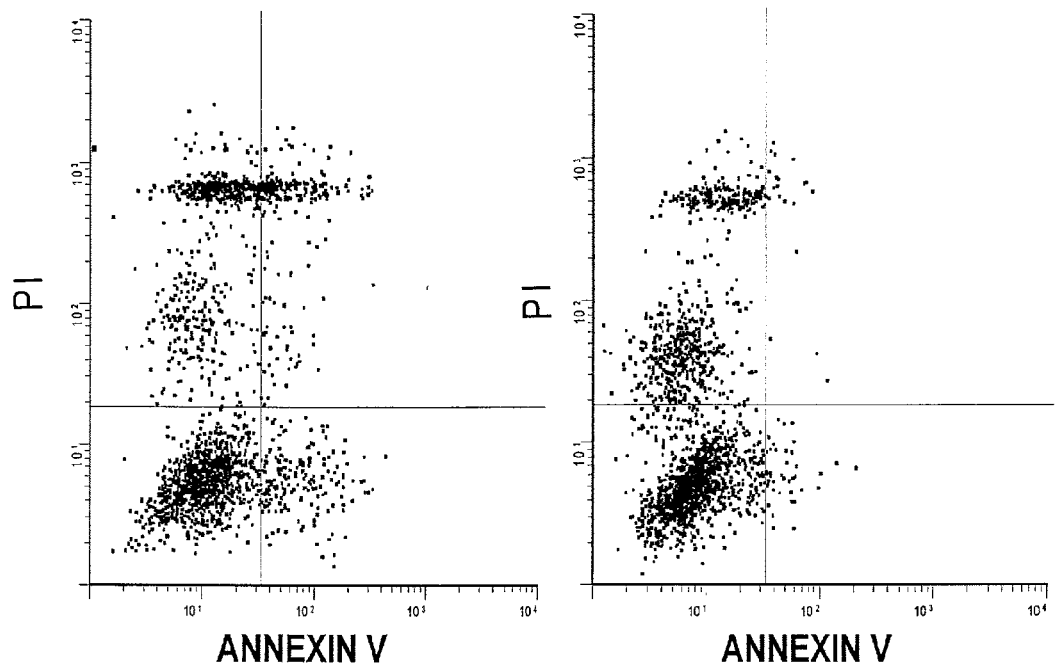

FIGS. 13A and 13B show that the expression of C21 increases the resistance of 3T3 fibroblasts to apoptosis induced by serum starvation. The figure shows 2-dimensional histograms (cytographs) of the staining of control 3T3-neo (FIG. 13A) and transfected 3T3-C21α (FIG. 13B) cells with propidium iodide (PI) and fluorescein-coupled Annexin V.

Figure 14:
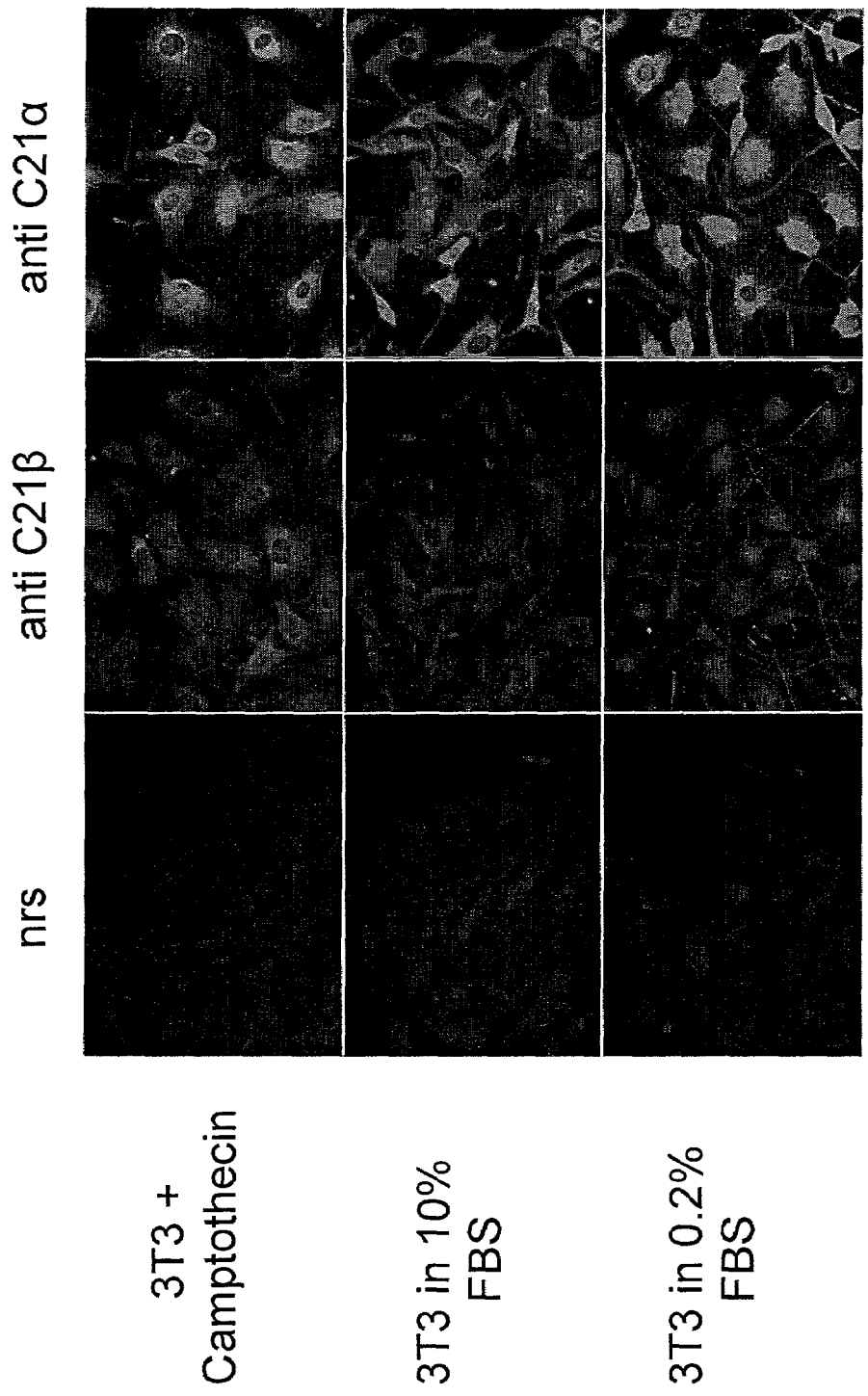

FIG. 14 shows the intracellular localization of C21. Apoptosis was induced by either serum starvation (incubation with DMEM containing 0.2% FBS for 16 hours) or growth with 100 ng/ml of the topoisomerase inhibitor, camptothecin (CPT). The cells were washed, fixed with 3.8% paraformaldehyde, permeabilized with 0.0.5% Triton-PBS and blocked with 10% human serum in PBS. They were then incubated with the anti-C21 antibodies (1:25) and stained with FITC-F(ab')2 anti-rabbit IgG antibody that had previously been absorbed to remove reactivity with human immunoglobulins.

Figures 15A, 15B:
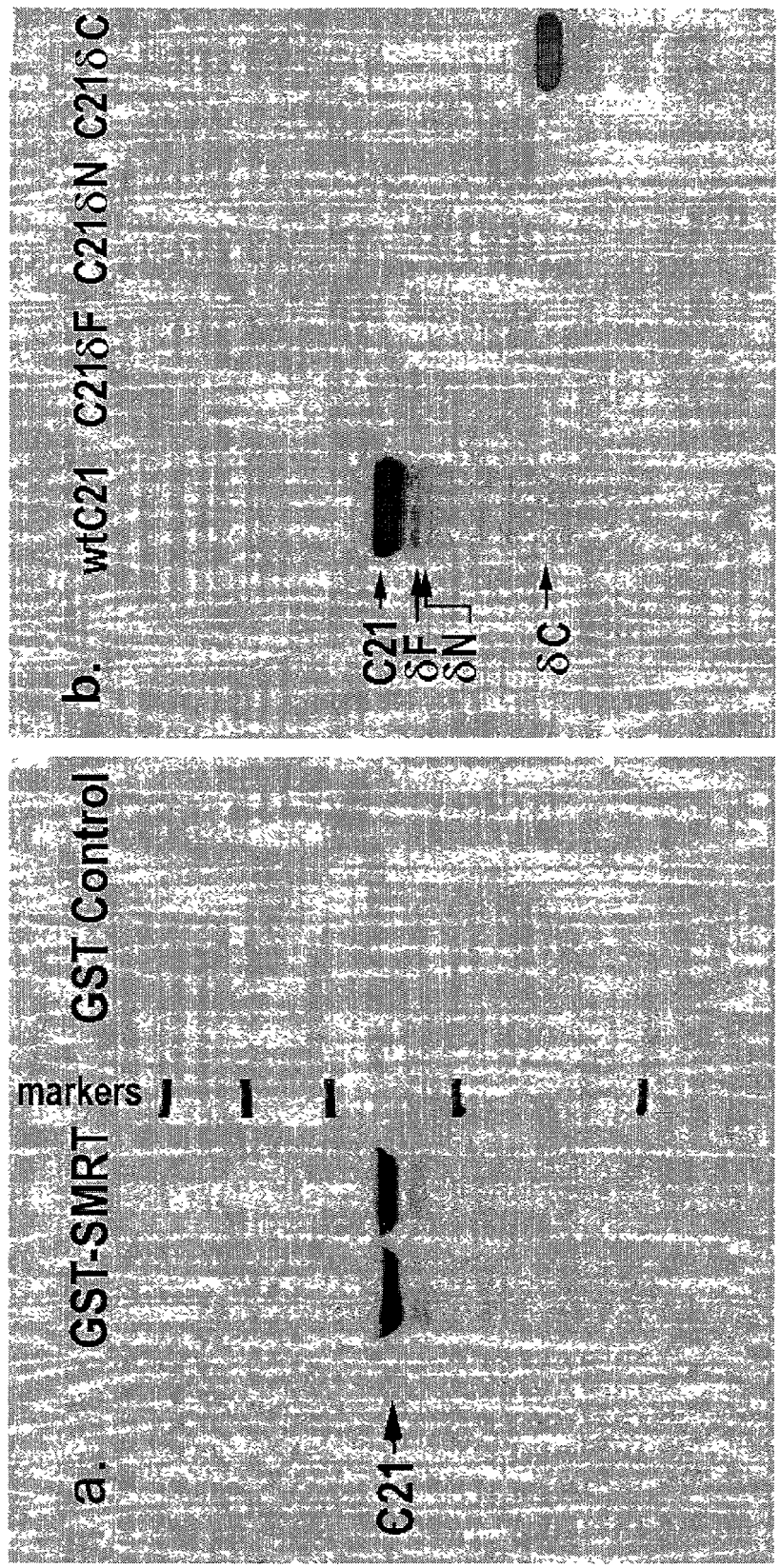

FIGS. 15A and 15B show GST-pull-down of in vitro synthesized C21 by SMRT (1-900). Hu SMRT(1-900) cDNA was amplified by PCR and cloned in-frame into pGEX-6p-1 (GST fusion expression vector for bacterial expression). Expression of the GST fusion protein (FIG. 15A) or control (FIG. 15B) was induced with IPTG and the product adsorbed onto glutathione sepharose 4B. hC21 (full-length ORF or fragments lacking the C-terminal half(δ C), the F-box (δ F), the N terminal 40 amino acid (δ N) or a construct lacking both the N-terminus and the F-box (δN+F) was cloned in-frame into pCDNA3 vector with a Flag tag at the N-terminus. The plasmid, linearized with EcoRI, was purified and used as a template to label the product. For the pull-down experiments, 5 ng of $^{35}$S-labeled hC21 protein(s) and 20 ul of GST agarose or GST-SMRT agarose were mixed. All four C21 constructs labeled with equal efficiency and the same quantity of labeled protein were used in each experiment. The denatured proteins were then electrophoresed through a 10% SDS PAGE gel.

Figure 16:
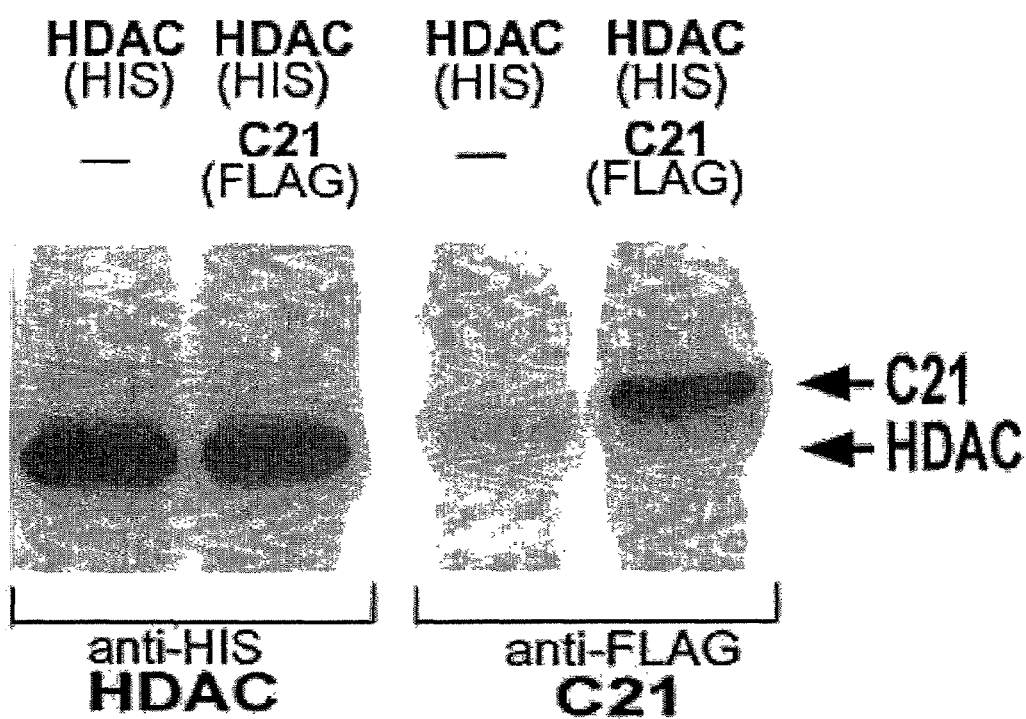

FIG. 16 shows that C21 co-precipitates with SMRT. COS7 cells were transfected with pCDNA His-HDAC3 and either pCDNA Flag-HC21 or an empty Flag vector. After 48 hours, the cells were lysed in RIPA buffer. The lysates were cleared and passed over a Ni-agarose column to adsorb the His-tagged HDAC3 and any associated proteins. After extensive washing, the bound proteins were eluted with SDS-PAGE loading buffer and analyzed. After transfer to nitrocellulose the SDS-PAGE-separated proteins were stained with anti-Flag and anti-His monoclonal antibodies.

Figure 17:
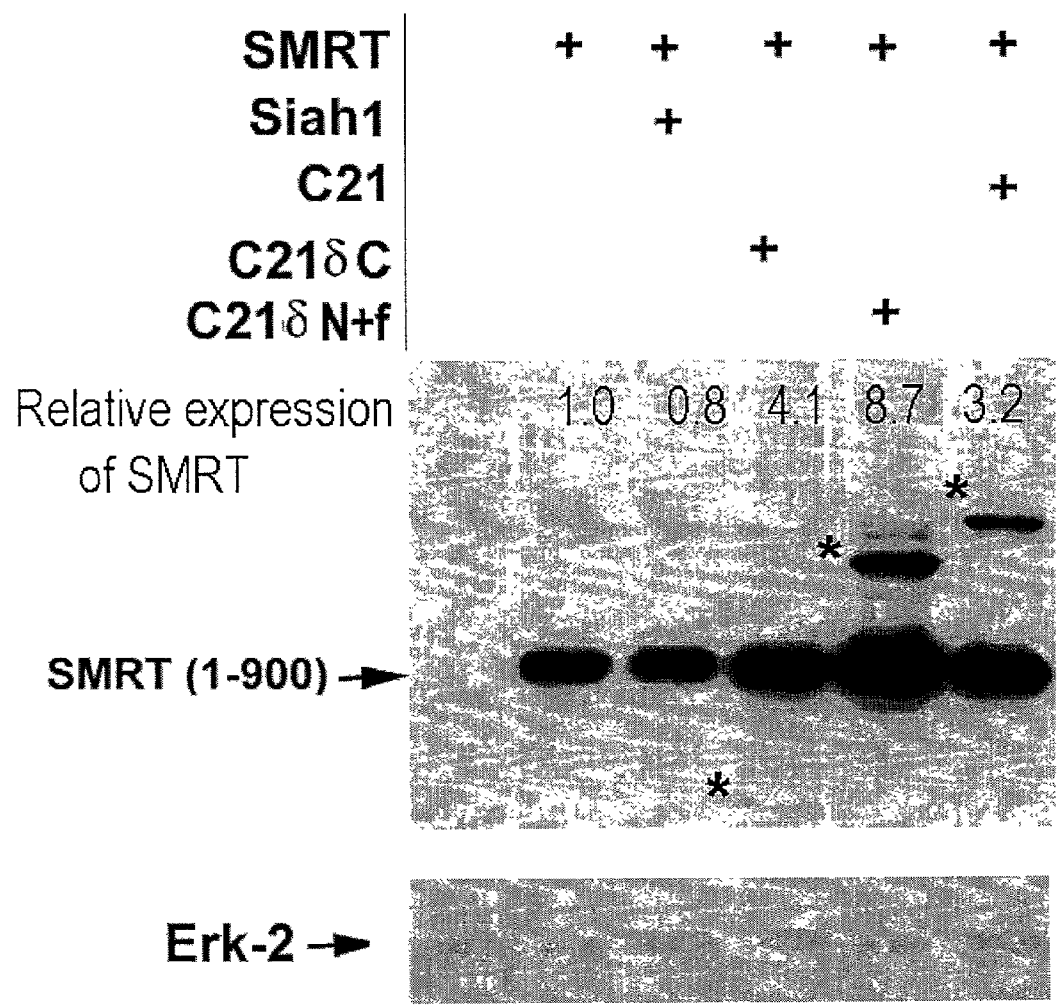

FIG. 17 shows that C21 expression increases the expression of nuclear hormone receptor co-repressors. 36 hours after transfection the cells were lysed in SDS loading buffer. Equal amounts of proteins were electrophoresed in SDS-PAGE gel and blotted. Anti-His mAb was used to detect the transiently expressed proteins. The C21 constructs used in this experiment were also His-tagged and are visible on the blot after staining. They are marked with * in the figure. The immunoprecipitates were quantified by phosphorimaging. After stripping, the blots were re-stained with anti-ERK as a control for loading differences.

Figure 18:
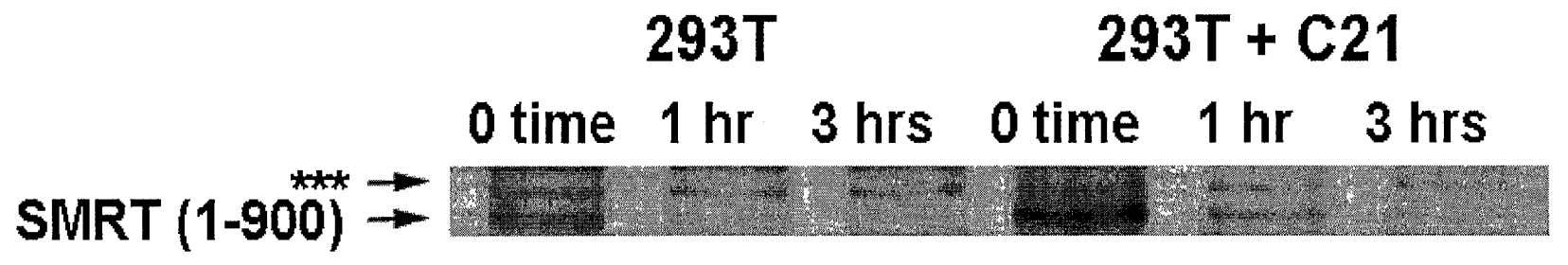

FIG. 18 shows that C21 stabilizes SMRT. 293T cells were transfected with PcDNA His-SMRT(1-300) and either C21 or an empty vector using CaPO4 mediated transfection. After 36 hours, the cells were pulse labeled for 1 hour with 0.1 mCi of [$^{35}$S]methionine, and the label chased with cold media. At the end of the labeling period and again after 1 and 3 hours, the cells were sampled, lysed in RIPA buffer, and the His-tagged proteins isolated with Ni-agarose. The eluted proteins were subjected to SDS-PAGE, and the dried gels were used to expose X-ray film.

Figure 19:
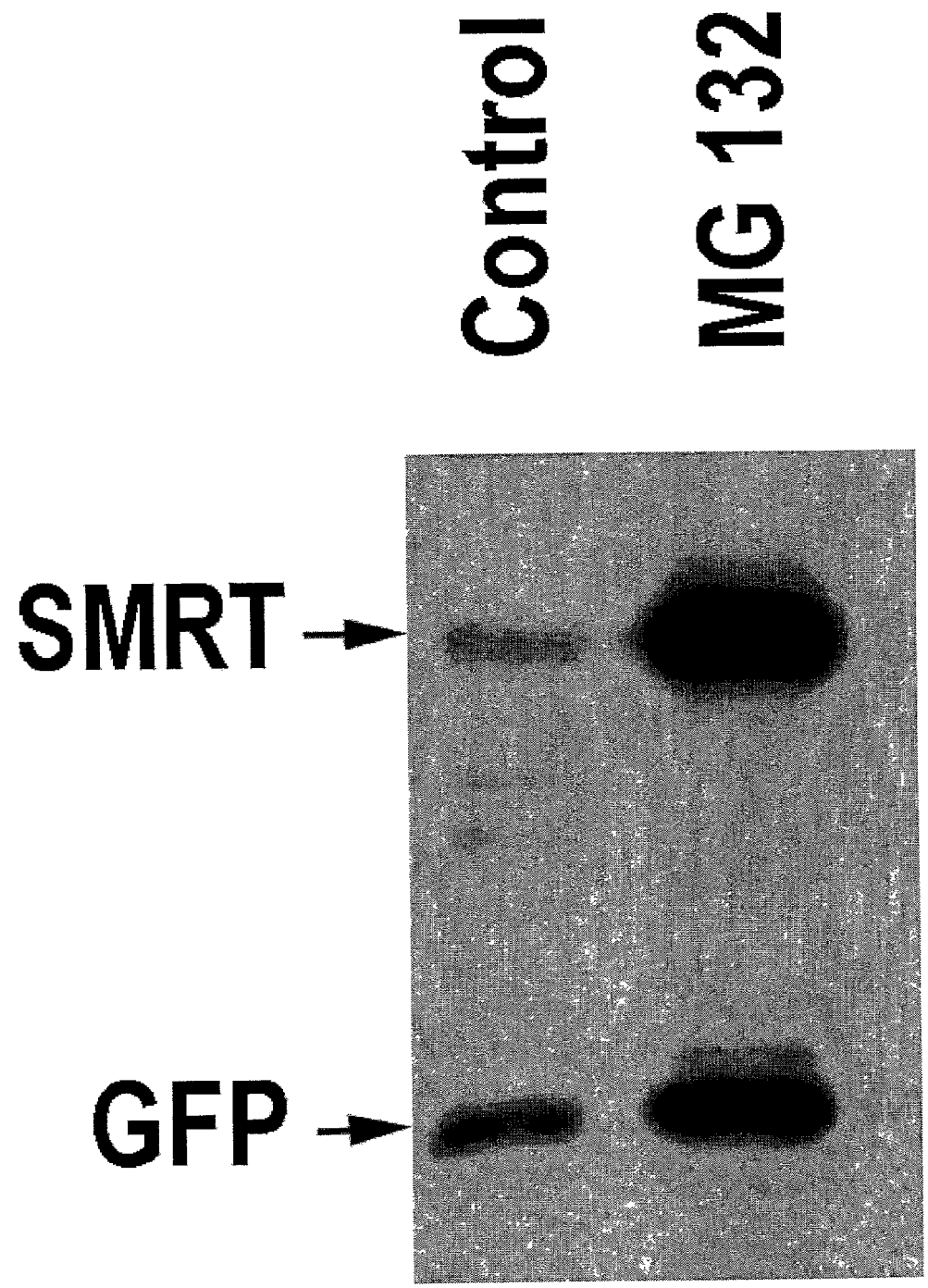

FIG. 19 shows the effect of proteasome inhibition on SMRT expression. COS7 cell, expressing SMRT(1-900) were treated with 15 um MG132 for 10 hours. The His-tagged SMRT was detected by Western blotting.

DETAILED DESCRIPTION OF THE INVENTION

The present invention is based on the discovery of a single C21 gene which encodes a family of proteins that can be detected by Western blotting and that plays a role in transcriptional regulation. The heterogeneity is due to the presence of multiple isoforms, produced by differential exon utilization. Although the ORF of the predominant form contains only 1545 bp, the gene occupies ~100 kb of genomic DNA on chromosome 3q and contains 16 exons. C21 has significant homology (79%) to only one other vertebrate gene, TBL1. Both C21 and TBL1 interact with proteins that regulate the nuclear hormone receptor family of transcription factors. C21a co-precipitates with a co-repressor of nuclear hormone receptors (NHR), SMRT (silencing mediator of retinoic acid and thyroid hormone receptors), in pull down experiments, and co-precipitates in complexes immunoprecipitated by antiserum to HDAC3 (histone deacetylase). Among the consequences of this interaction are stabilization of the co-repressor molecules and transcriptional silencing.

C21 was isolated in the laboratory of the present inventor as a 201 bp fragment in a cDNA library prepared from a bone marrow preparation highly enriched for human hematopoietic stem cells. This fragment, which had no homology with any sequence in the Gene Bank, hybridized with RNA from K562 (a human erythroleukemia cell line) and a placental library, and cDNAs prepared from these tissues were used as a source of mRNAs for subsequent analysis. 5' RACE identified an open reading frame (ORF) encoding a putative 514 amino acid protein. The nucleotide sequences and the putative protein translation of these messages and the homologous mouse sequences are presented in the Sequence Listing as SEQ ID NO:1 (human C21α cDNA), SEQ ID NO:2 (human C21α protein), SEQ ID NO:3 (human C21β cDNA), SEQ ID NO:4 (human C21β protein), SEQ ID NO:11 (mouse C21 cDNA), and SEQ ID NO:12 (mouse C21 protein). 3' RACE using a primer encoding nucleotides no. 1410–1425 in the ORF (SEQ ID NO:1) produced a new sequence that diverged from the original sequence at nucleotide no. 1570. The new sequence encodes 45 amino acids, is in-frame, and encodes an alternative carboxyl terminus for the protein. 5' RACE extended the published sequence by 80 nucleotides and also revealed an additional mRNA with a small insert between exons 2 and 3 of the original structure. This insert of 22 nucleotides GTAAGACTCTCCAACTCCCAAT (SEQ ID NO:16) is within the 5' UTR and is not present in all samples but occurs with a frequency large enough to rule out its being a PCR artifact. It may have a regulatory function or be involved in tissue specificity.

Dot blots and Northern analysis showed that the product of the C21 gene is expressed widely and Northern analysis, using sequences from the ORF as a probe, revealed size heterogeneity of the expressed mRNA. Northern analysis with RNA extracted from a variety of sources including the human leukemia cells K562, CHRF, Jurkat and Raji, showed two predominant forms (4.7 kb and ~7.3 kb) of mRNA. The smaller form is more abundant in hematopoietic tissues. Several isoforms of the protein exist. C21β, differs from the original sequence at the carboxyl-terminus (3' end of the ORF). Western blotting with highly specific anti-peptide antibodies shows several additional isoforms, whose pattern of expression varies from tissue to tissue. The mouse homologue has also been identified and Northern blotting of mouse tissues shows size heterogeneity that is similar to the human RNA. Analysis of the genomic DNA encoding C21 revealed that the isoforms are produced by the use of alternative splice donor sites. C21 maps to chromosome 3q26-27.

The cDNAs for C21 encode previously unknown members of the β-transducin or WD-repeat family (Neer et al, 1994). This family of proteins is defined by the occurrence of 4–8 repetitions of a conserved motif in each member polypeptide. The conserved core of the repeating unit usually ends with the sequence Trp-Asp, thus defining the WD40 repeat. Asparagine (N) is almost as common as aspartic acid in the terminal position. The WD-repeat motif is present in a large group of functionally diverse proteins (>90 members). None are known to have enzymatic activity. It is believed that the WD-repeat domains mediate protein—protein interactions. The splice site that distinguishes between C21α and C21β is immediately 3' of the last WD-repeat sequence signature.

At the nucleotide level the sequence of C21α has 79% homology to *Homo sapiens* mRNA for transducin (β)–1 like protein (TBL1) (#Y12781, GenBank Accession No. NM005647). The only homology of C21 and TBL1 to the prototypic signal transducing guanine nucleotide binding regulatory (G) protein β sub unit is in the WD-repeat domains. TBL1 has been mapped to the X chromosome and deletions in the region containing TBL1 are associated with adult onset sensorineural deafness (Bassi et al, 1999). Both C21 and TBL1 are homologous to a *Drosophila* protein called ebi (GenBank Accession No. AF146345 for encoding nucleotide sequence). Ebi has been reported to regulate epidermal growth factor receptor signaling (Dong et al, 1999), promote the degradation of a repressor of neuronal differentiation (Ttk88), and to limit S phase entry (Boulton et al, 2000). The regions of maximal nucleotide conservation among TBL1, ebi and C21 are in the N-terminal end of the molecule and in the WD40 repeats. The C-terminal ends of these proteins are not homologous. The carboxyl terminal exon of C21α has some homology to several members of the Arp2/3 complex of proteins that control actin polymerization (Welch et al, 1997). The equivalent region of C21β has no homology to any known protein. Like TBL1, C21 contains a series of WD-repeat domains within the C-terminal half of the ORF. The N-terminal half of TBL1 interacts with both HDAC3 and SMRT to form an effective transcriptional repressor (Guenther et al, 2000). Ectopic expression of TBL1 potentiates repression by unliganded T3R. TBL1 does not bind directly to T3R; it binds to SMRT and/or N-CoR, and this interaction was reported to contribute an autonomous repression function to the complex. The methods used in these experiments could not distinguish among the possibilities that: 1) TBL1 activated N-CoR, producing increased repression, 2) it increased the quantity of N-CoR present in the target cells by protecting it from degradation or 3) it recruited an additional co-repressor.

C21, TBL1 and ebi all contain a variant F-box near the N terminus of the molecule. F-box proteins are a family of eukaryotic proteins that contain a ~40-amino acid motif called the F-box because it was first identified in cyclin F. F-box proteins, in combination with Skp1 and Cullin, forms part of a E3 ubiquitin ligase that plays a critical role in the targeting of phosphorylated proteins for ubiquitination and subsequent proteasomal degradation. The bulk of this protein degradation is carried out by the 26S proteasome, and proteins are targeted to this compartment by the covalent attachment of a multiubiquitin chain. Because proteolysis is irreversible, proteasomal degradation provides a unidirectional regulatory switch. The initiation of DNA replication, chromosome segregation, and exit from mitosis are all triggered by the destruction of key regulatory proteins (DeSalle et al, 2001; Schwob et al, 1994; Glotzer et al, 1991). Ubiquitination is initiated by a ubiquitin-activating enzyme (E1), which adenylates ubiquitin and becomes linked to it via a thioester bond. Ubiquitin then is transferred to a ubiquitin-conjugating enzyme, E2. While E2s can attach ubiquitin directly to lysine residues in a substrate, most physiological ubiquitination reactions probably require a ubiquitin ligase, or E3 (Hershko et al, 1983). E3s have been implicated in substrate recognition. Once the substrate is multi-ubiquitinated, it then is recognized and degraded by the 26S proteasome (Hershko et al, 1983).

This pathway leading to proteasomal degradation has been reviewed recently (Ciechanover, 1993; Hochstrasser, 1992) and the role of the F-box has been reviewed by Pagano (Kipreos et al, 2000). The F-boxes in C21, TBL1 and ebi all lack a tryptophan near the NH2-end of the motif that is associated with Skp1 binding to F-box proteins that recognize phosphorylated protein (Kipreos et al, 2000). A cDNA, described only as the "human homologue of ebi" encodes a protein that the authors believe plays a role in the ubiquitin mediated destruction of β-catenin (Matsuzawa et al, 2001) and they suggested that this ebi can bind Skp1 and is a key component in a new pathway for targeting unphosphorylated proteins for ubiquitination and subsequent proteasomal degradation (Matsuzawa et al, 2001; Liu et al, 2001).

Co-transfection of C21 with SMRT has been shown to lead to greatly enhanced SMRT expression in a transient expression model. Since SMRT is degraded via a ubiquitin-mediated mechanism and inhibition of ubiquitination leads to elevation of SMRT, the data from the laboratory of the present inventor suggest the possibility that C21 may act by preventing the degradation of nuclear co-repressors. This stabilization appears to be part of a complex regulatory network that governs the level of unliganded nuclear receptor. Although this result is the opposite of what might have been predicted on the basis of the results described above for ebi-mediated targeting of β-catenin (Matsuzawa et al, 2001), both sets of data suggest that the C21 family interacts with proteins subject to proteasomal degradation and the actual outcome, protection or targeting, may depend on either the nature of the target protein or the identity of the other proteins that interact with C21. It may also be controlled by which of the C21 family members that does the interacting. The physiological effects of altering co-repressor stability are not known but it is predicted that this family plays a role in maintaining stem cells in their undifferentiated state.

When the cDNA encoding C21α was over-expressed in 3T3 cells, the growth properties were altered: clones expressing C21, grown under sub-optimal growth conditions, plated with 2–3 times the efficiency of untransfected 3T3 cells. The increased plating efficiency is a result of increased resistance to apoptotic stimuli leading to increased survival in the interval before the cells attach to the plastic surface of the culture vessel. All cell lines that over-express this protein become resistant to the apoptotic effects of serum starvation. Apoptosis in thymocytes is regulated by the activity of an NHR family member, RORγ (Kurebayashi et al, 2000). When this transcription factor is present, thymocyte development proceeds normally. However, in its absence, apoptosis increases and thymocyte development fails. Stabilization of a NHR-co-repressor complex by C21 could explain how C21 inhibits apoptosis.

Transgenic mice that over-express C21 in their hematopoietic cells have significant abnormalities in granulocyte development. As shown in Table 1 of Example 2, mice expressing C21 under the control of the vav promoter, have normal numbers of total WBC but have a significant "shift to the left", i.e., these animals have very few mature granulocytes and an increased number of immature forms. This phenotype resembles what happens when wild type RARα is over-expressed in hematopoietic cells (Kastner et al, 2001) suggesting that anything that leads to an increase in the proportion of unliganded RAR inhibits RA-controlled differentiation.

Based on the above characterization of C21, the present invention is directed to a C21 polypeptide having the amino acid sequence of SEQ ID NO:2 (human C21α) which interacts with, and has the activity of modulating the stability of, transcriptional regulatory complexes (i.e., transcriptional co-repressor complexes) that regulate nuclear hormone receptor activity and to a nucleic acid molecule encoding the polypeptide of the present invention. As will be appreciated by those of skill in the art, the polypeptide of the present invention is also intended to encompass a fragment of the C21 polypeptide which retains the activity of the full-length C21 polypeptide. Further comprehended by the C21 polypeptide according to the present invention is a variant of the c21 polypeptide having an amino acid sequence with at least 85%, preferably at least 90% or 95%, sequence identity to SEQ ID NO:2, which interacts with, and also has the activity of modulating the stability of, transcriptional regulatory complexes that regulate nuclear hormone receptor activity. For instance, the human β form of C21 (SEQ ID NO:4) and the mouse C21 (SEQ ID NO:12), which have approximately 92% and 97% sequence identity with SEQ ID NO:2 (human C21α), are considered as variant polypeptides comprehended by the polypeptide of the present invention.

A second aspect of the present invention provides for antibodies raised against the polypeptide according to the present invention and molecules which includes the antigen-binding portion of such antibodies.

It should be understood that when the term "antibodies" is used with respect to the antibody embodiments of the present invention, this is intended to include intact antibodies, such as polyclonal antibodies or monoclonal antibodies (mAbs), as well as proteolytic fragments thereof such as the Fab or F(ab')$_2$ fragments. Furthermore, the DNA encoding the variable region of the antibody can be inserted into other antibodies to produce chimeric antibodies (see, for example, U.S. Pat. No. 4,816,567) or into T-cell receptors to produce T-cells with the same broad specificity (see Eshhar, et al, 1990 and Gross et al, 1989). Single-chain antibodies can also be produced and used. Single-chain antibodies can be single-chain composite polypeptides having antigen binding capabilities and comprising a pair of amino acid sequences homologous or analogous to the variable regions of an immunoglobulin light and heavy chain (linked $V_H$-$V_L$ or single-chain $F_v$). Both $V_H$ and $V_L$ may copy natural monoclonal antibody sequences or one or both of the chains may comprise a CDR-FR construct of the type described in U.S. Pat. No. 5,091,513 (the entire content of which is hereby incorporated herein by reference). The separate polypeptides analogous to the variable regions of the light and heavy chains are held together by a polypeptide linker. Methods of production of such single-chain antibodies, particularly where the DNA encoding the polypeptide structures of the $V_H$ and $V_L$ chains are known, may be accomplished in accordance with the methods described, for example, in U.S. Pat. Nos. 4,946,778, 5,091,513 and 5,096,815, the entire contents of each of which are hereby incorporated herein by reference.

An antibody is said to be "capable of binding" a molecule if it is capable of specifically reacting with the molecule to thereby bind the molecule to the antibody. The term "epitope" is meant to refer to that portion of any molecule capable of being bound by an antibody which can also be recognized by that antibody. Epitopes or "antigenic determinants" usually consist of chemically active surface groupings of molecules such as amino acids or sugar side chains and have specific three dimensional structural characteristics as well as specific charge characteristics.

Polyclonal antibodies are heterogeneous populations of antibody molecules derived from the sera of animals immunized with an antigen.

Monoclonal antibodies (mAbs) are a substantially homogeneous population of antibodies to specific antigens. MAbs may be obtained by methods known to those skilled in the art. See, for example Kohler et al, (1975); U.S. Pat. No. 4,376,110; Harlow et al, (1988); and Colligan et al, (2001), the entire contents of which references are incorporated entirely herein by reference. Such antibodies may be of any immunoglobulin class including IgG, IgM, IgE, IgA, and any subclass thereof. The hybridoma producing the mAbs of this invention may be cultivated in vitro or in vivo. High titers of mabs can be obtained by in vivo production where cells from the individual hybridomas are injected intraperitoneally into pristane-primed Balb/c mice to produce ascites fluid containing high concentrations of the desired mAbs. MAbs of isotype IgM or IgG may be purified from such ascites fluids, or from culture supernatants, using column chromatography methods well known to those of skill in the art.

Chimeric antibodies are molecules, the different portions of which are derived from different animal species, such as those having a variable region derived from a murine mAb and a human immunoglobulin constant region. Chimeric antibodies are primarily used to reduce immunogenicity during application and to increase yields in production, for example, where murine mabs have higher yields from hybridomas but higher immunogenicity in humans, such that human/murine chimeric or humanized mAbs are used. Chimeric and humanized antibodies and methods for their production are well-known in the art, such as Cabilly et al (1984), Morrison et al (1984), Boulianne et al (1984), Cabilly et al European Patent 0 125 023 (1984), Neuberger et al (1985), Taniguchi et al European Patent 0 171 496 (1985), Morrison et al European Patent 0 173 494 (1986), Neuberger et al WO 8601533 (1986), Kudo et al European Patent 0 184 187 (1986), Sahagan et al (1986); Robinson et al WO 9702671 (1987), Liu et al (1987), Sun et al (1987), Better et al (1988), and Harlow et al (1988). These references are hereby incorporated herein by reference.

A "molecule which includes the antigen-binding portion of an antibody," is intended to include not only intact immunoglobulin molecules of any isotype and generated by any animal cell line or microorganism, or generated in vitro, such as by phage display technology for constructing recombinant antibodies, but also the antigen-binding reactive fraction thereof, including, but not limited to, the Fab fragment, the Fab' fragment, the F(ab')$_2$ fragment, the variable portion of the heavy and/or light chains thereof, and chimeric or single-chain antibodies incorporating such reactive fraction, or molecules developed to deliver therapeutic moieties by means of a portion of the molecule containing such a reactive fraction. Such molecules may be provided by any known technique, including, but not limited to, enzymatic cleavage, peptide synthesis or recombinant techniques.

A further aspect of the present invention is directed to a nucleic acid molecule which encodes the polypeptide of the present invention. As one embodiment, the nucleic acid molecule contains the nucleotide sequence encoding the amino acid sequence of SEQ ID NO:2. In a preferred embodiment, the nucleotide sequence encoding SEQ ID NO:2 (human C21α) is nucleotides 161 to 1705 of SEQ ID NO:1.

The nucleic acid molecule of the present invention further comprehends those nucleic acid molecules that encode variants of the polypeptide of SEQ ID NO:2, such as the variant polypeptides of SEQ ID NO:4 or SEQ ID NO:12. These nucleic acid molecules have high homology to nucleotides 161 to 1705 of SEQ ID NO:1 and include the nucleic acid molecules having the nucleotide sequence of nucleotides 161 to 1705 of SEQ ID NO:3 or nucleotides 202 to 1746 of SEQ ID NO:11, which hybridize to nucleotides 161 to 1705 of SEQ ID NO:1 under highly stringent conditions.

The nucleotide sequence of naturally-occurring variants of human C21α in question, such as, for example, allelic variations and splice variants, may be determined by hybridization of a cDNA library using a probe which is based on the identified polynucleotide, under highly stringent conditions. Stringency conditions are a function of the temperature used in the hybridization experiment and washes, the molarity of the monovalent cations in the hybridization solution and in the wash solution(s) and the percentage of formamide in the hybridization solution. In general, sensitivity by hybridization with a probe is affected by the amount and specific activity of the probe, the amount of the target nucleic acid, the detectability of the label, the rate of hybridization, and the duration of the hybridization. The hybridization rate is maximized at a Ti (incubation temperature) of 20–25° C. below Tm for DNA:DNA hybrids and 10–15° C. below Tm for DNA:RNA hybrids. It is also maximized by an ionic strength of about 1.5 M Na$^+$. The rate is directly proportional to duplex length and inversely proportional to the degree of mismatching.

Specificity in hybridization, however, is a function of the difference in stability between the desired hybrid and "background" hybrids. Hybrid stability is a function of duplex length, base composition, ionic strength, mismatching, and destabilizing agents (if any).

The Tm of a perfect hybrid may be estimated for DNA: DNA hybrids using the equation of Meinkoth et al (1984), as $$Tm = 81.5° \text{ C.} + 16.6 \ (\log M) + 0.41 \ (\% \ GC) - 0.61 \ (\% \ \text{form}) - 500/L$$

and for DNA:RNA hybrids, as $$Tm = 79.8° \text{ C.} + 18.5 \ (\log M) + 0.58 \ (\% \ GC) - 11.8 \ (\% \ GC)^2 - 0.56(\% \ \text{form}) - 820/L$$

where

M, molarity of monovalent cations, 0.01–0.4 M NaCl,

% GC, percentage of G and C nucleotides in DNA, 30%–75%,

% form, percentage formamide in hybridization solution, and

L, length hybrid in base pairs.

Tm is reduced by 0.5–1.5° C. (an average of 1° C. can be used for ease of calculation) for each 1% mismatching.

The Tm may also be determined experimentally. As increasing length of the hybrid (L) in the above equations increases the Tm and enhances stability, the full-length human C21α DNA sequence can be used as the probe.

Filter hybridization is typically carried out at 68° C., and at high ionic strength (e.g., 5–6×SSC), which is non-stringent, and followed by one or more washes of increasing stringency, the last one being of the ultimately desired stringency. The equations for Tm can be used to estimate the appropriate Ti for the final wash, or the Tm of the perfect duplex can be determined experimentally and Ti then adjusted accordingly.

Hybridization conditions should be chosen so as to permit allelic variations and splice variants, but avoid hybridizing to other genes. In general, stringent conditions are considered to be a Ti of 5° C. below the Tm of a perfect duplex, and a 1% divergence corresponds to a 0.5–1.5° C. reduction in Tm. Typically, rat clones were 95–100% identical to database rat sequences, and the observed sequence divergence may be artifactual (sequencing error) or real (allelic variation). Hence, use of a Ti of 5–15° C. below, more preferably 5–10° C. below, the Tm of the double stranded form of the probe is recommended for probing a cDNA library.

As used herein, highly stringent conditions are those which are tolerant of up to about 15% sequence divergence. Without limitation, examples of highly stringent (5–15° C. below the calculated Tm of the hybrid) conditions use a wash solution of 0.1×SSC (standard saline citrate) and 0.5% SDS at the appropriate Ti below the calculated Tm of the hybrid. The ultimate stringency of the conditions is primarily due to the washing conditions, particularly if the hybridization conditions used are those which allow less stable hybrids to form along with stable hybrids. The wash conditions at higher stringency then remove the less stable hybrids. A common hybridization condition that can be used with the highly stringent wash conditions described above is hybridization in a solution of 6×SSC (or 6×SSPE), 5× Denhardt's reagent, 0.5% SDS, 100 μg/ml denatured, fragmented salmon sperm DNA at an appropriate incubation temperature Ti.

Other additional aspects of the present invention include a vector containing the nucleic acid molecule of the present invention, a host cell transformed with the nucleic acid of the present invention, and a method for producing the polypeptide of the present invention. This method involves culturing the host cell transformed with the nucleic acid molecule of the present invention in nutrient medium and then recovering the polypeptide expressed and produced by the cultured host cell.

The C21 family of regulatory proteins which is differentially expressed by early hematopoietic cells has been identified by the present inventor. These proteins, referred to herein as polypeptides of the present invention, interact with transcriptional repressor complex and are members of a new class of regulatory molecules that regulate the stability of their targets by controlling their susceptibility to ubiquitin mediated proteasomal degradation. Evidence is accumulating that the regulation of transcriptional activity is a central mechanism in the control of lineage specification and that members of the C21 family of proteins play an important role in this process. C21 exists in multiple isoforms, and two of these (α and β) are expressed at high levels in immature hematopoietic cells. Expression of both C21 α and β isoforms declines during hematopoietic maturation but the β form is found in some mature myeloid cells.

C21 interacts with the transcriptional repressor complex and specifically binds to SMRT. This binding results in elevation of the intracellular concentration of SMRT. Aberrant or unregulated alterations in C21 levels may have leukemogenic potential. The laboratory of the present inventor has already shown that over-expression leads to abnormal myeloid development in young mice, and these animals will be followed as they age. Approximately 40% of acute myelogenous leukemia (AML) cases of the M2 subtype are due to a chromosomal translocation that combines a sequence-specific DNA binding protein, AML1, with a potent transcriptional repressor, ETO. Like C21, ETO interacts with nuclear receptor co-repressors SMRT and N-CoR, which recruit histone deacetylase (HDAC) to the AML1-ETO oncoprotein (Muramatsu et al, 2001; He et al, 1998). Inhibitors of HDAC are the potent inducer/enhancers of differentiation in acute myeloid leukemia (Kosugi et al, 1999) and the potential therapeutic benefit of HDAC inhibition has been established by the use of enzyme inhibitors in vitro and at least one reported case of experimental therapy (Kramer et al, 2001). CI-994 (acetyldinaline), an HDAC inhibitor, is currently in Phase II trials. If members of the C21 family regulate HDAC recruitment by N-CoR/SMRT, they may provide another target for therapeutic attack in this disease.

The gene encoding C21 is located in a chromosomal region that is known to be the site of many chromosomal abnormalities. A significant proportion of AML, of the non-M2 type, involve translocations that involve the q arm of chromosome 3 and these have a poor prognosis (Grimwade et al, 1998). Interestingly, leukemias involving chromosome 3q are among the subset of malignancies that do not have mutations in p53 (Munoz et al, 1999). Recently the observation was made that AML with chromosome 3q abnormalities was highly correlated with prior exposure to mutagens (Lindquist et al, 2000).

The consequences of the interaction of C21 with the nuclear transcription repressor complex have only begun to be explored, but several clinically important consequences suggest themselves in addition to a possible involvement of C21 with leukemia. The stabilizing interaction of C21 with nuclear co-repressors may be replicated by small molecules that mimic C21 binding. Such molecules could provide a new and novel means of altering the differentiation of cultured hematopoietic cells and might allow the expansion of undifferentiated progenitors or stem cells (Muramatsu et al).

The anti-apoptotic effect of over-expression could protect stem cells (hematopoietic as well as others) from inappropriate or excessive apoptotic stimuli. Defects in the related TBL-1 gene lead to degeneration of the Organ of Corti in middle age, perhaps suggesting that this gene family plays a role in protection against environmental or age-related damage. If means were available to control the expression of C21 in specific tissues or to replicate their effects with small molecules, it might extend their functional life in vivo and also permit their growth in culture. Selective expansion of normal HSC could provide a source of uncontaminated stem cells for autologous BM transplants in patients with both hematological malignancies and advanced solid tumors as well as providing a large pool of cells that could be used as vehicles for genetic therapies. Other proteins with anti apoptotic effects such as Bcl-2, prevent the elimination of cells that are otherwise targeted for destruction, and act as oncogenes. The high frequency of genetic abnormalities at or near 3q26 may indicate the C21 also can serve as an oncogene. Amplification or over-expression of C21 might reduce the ability of cells to respond to environmental changes and thus might alter resistance to cytotoxic drugs. Pharmacological manipulation of C21 levels could be useful in altering resistance to chemotherapeutic agents or after toxic or radioactive exposures.

Having now generally described the invention, the same will be more readily understood through reference to the following examples which are provided by way of illustration and are not intended to be limiting of the present invention.

EXAMPLE 1

Using CD34+/CD38− cells as starting material, the laboratory of the present inventor has identified four mRNAs, expressed by these cells that are either absent or present in reduced amounts in more mature CD34+/CD38+ cells. One of these cDNAs (C40) encodes a known member of the subfamily of protein phosphatases (CL100) that exhibits dual substrate specificity for phosphotyrosine- and phosphoserine/threonine-containing substrates and specifically inactivates MAP kinases. This phosphatase has been shown to play a role in regulating the differentiation of several cell types. The second cDNA, (C23) is identical to LR11 (gp250) a member of the Low Density Lipoprotein Receptor family. LR11 is unusual in that in addition to 11 ligand-binding repeats, it contains a series of fibronectin type III repeats near its carboxyl-terminal end which are similar to those found in cytokine receptors. It is highly expressed in developing brain but hematopoietic expression has not been reported. The 178 bp fragment that was originally cloned is part of a 4145 bp 3' UTR that had not been previously sequenced and is among the largest human 3' UTR ever reported. The other isolates (C21 and C12) do not correspond to known protein sequences. They are homologous to EST sequences from a fetal brain library. C21 encodes a previously unknown gene that is a member of the WD-40 family. An open reading frame encoding a 515 amino acid protein has been identified.

MATERIALS AND METHODS

Cell Preparations

Bone marrow specimens were obtained from discarded orthopedic surgical specimens. Peripheral blood leukocytes were obtained from 20 ml whole blood samples provided by volunteers. CD34+/CD38− cells were prepared from adult marrow by a combination of immunomagnetic techniques and cell sorting. Both positive and negative immunoselection were used. Negative selection to enrich CD34+ cells was performed using an immunomagnetic system (STEM-SEPT™; Stem Cell Technologies, Vancouver, British Columbia, Canada). The system uses a cocktail of monoclonal antibodies that have been bound in bispecific antibody complexes directed against cell surface antigens on human hematopoietic cells (CD2, CD3, CD14, CD19, CD25, CD56, CD66b and glycophorin A) and dextran. The separation column consists of dextran-coated ferro-magnetic steel wool packed in a plastic column and mounted in a high gauss magnetic field. The column retains antibody-coated cells. Since the magnetic separation used in the first step of this preparation removes cells expressing lineage specific markers, the resultant cell populations are all lineage negative (Lin-). The Lin-CD34-enriched cells were then stained with anti-CD34-PE (clone HPCA-1; Becton Dickinson, San Jose, Calif.) and anti-CD38 FITC (clone HIT2; CALTAG, South San Francisco, Calif.). The antibodies were used at saturating concentrations, approximately 0.5 ug/ml. The stained cells were sorted on an Epics Elite modified for high speed sorting. CD34+/CD38+ and CD34+/CD38−populations were sorted. A representative result obtained using this protocol is shown in FIGS. 1A–1D. The final purity of the sorted populations was always >98%.

Peripheral blood neutrophils, lymphocytes and monocytes were also prepared by sorting. Whole blood was incubated in Tris-buffered ammonium chloride to lyse the erythrocytes. The white blood cells (WBC) were pelleted by low speed centrifugation and resuspended in phosphate buffered isotonic saline containing 1 mg/ml of bovine serum albumin (PBS-BSA). The unstained samples were sorted on the basis of low angle (forward) and right angle light scatter and three populations, corresponding to lymphocytes, monocytes and neutrophils were isolated.

Construction of Subtracted Library

Total RNA was prepared from the sorted cells and double-stranded cDNAs were prepared from these RNAs using the CapFinder™ PCR cDNA Synthesis Kit provided by Clontech Laboratories (Palo Alto, Calif.). cDNAs from CD34+/CD38− and CD34+/CD38+ cells were used as "tester" and "driver" to produce the subtracted cDNA. A total of 57,000 CD34+/CD38−cells were used to prepare the tester RNA while 478,000 CD34+/CD38+ cells were used to prepare the driver RNA. The RNA was isolated using a modification of the method of Chomczynski et al (1987) (Stratagene, La Jolla, Calif.). The tester and driver cDNAs were digested with Rsa I, a four base cutter that leaves blunt ends. The tester cDNA was then divided into two portions, each of which was ligated to the adaptors provided by Clontech in their PCR Subtraction kit. These adaptors lack terminal $PO_4$ and thus only a single adaptor was added to each tester strand. Tester cDNA and driver cDNAs were heated to 100° C., for 3 minutes, and then the driver hybridized with each of the tester samples at 68° C., for 8 hours. Under these conditions, abundant messages hybridize rapidly while rare messages anneal more slowly and after hybridization, the residual single stranded material is enriched for low abundance sequences. The two hybridization mixtures (one for each of the adaptors) were mixed without being denatured again. Additional denatured driver was added and the mixture hybridized for 16 hours. Differentially expressed cDNAs were then amplified by PCR. The missing complementary strands of the adaptors were filled in by a brief incubation at 75° C., and then thermally denatured to begin a conventional PCR cycle. After 30 cycles the reaction was stopped and a small aliquot removed, diluted and amplified further using the nested primers provided in the kit. The pCR2.1 (plasmid) vector was used to prepare the library. As supplied by Invitrogen (Carlsbad, Calif.), pCR2.1 contains a pre-nicked insertion site for T/A cloning.

3' and 5' RACE

3' and 5' RACE were performed with Marathon-ready cDNA (Clontech) according to the manufacturer's protocol. The first PCR was performed with a specific primer and an adaptor primer (primer 1) using the following conditions: 1 minute at 94° C., followed by 35 cycles of 30 seconds at 94° C., 30 seconds at 60° C., and 2–4 minutes at 72° C. with a final 10 minute extension at 72° C. The PCR products were diluted and subjected to a second PCR using an internal specific primer and adaptor primer 2. After electrophoresis in agarose containing ethidium bromide, the bands were excised. The DNA was purified using a silica-gel membrane (Gel Purification Kit; Qiagen, Valencia, Calif.) and ligated into PCR2.1 vector. PCR using specific primers was used to identify positive colonies. Five plasmids from each band were sequenced.

Library Screening

The subtracted cDNA library was used to transform *E. coli* InV2F' cells (Invitrogen). Plasmids were prepared from individual colonies. After digestion with EcoR1, the plasmid DNAs were electrophoresed through a 1% agarose gel and transferred to nitrocellulose membranes. Duplicate membranes were hybridized with $^{32}$P-labeled cDNA from CD34+/CD38− and CD34+/CD38+ cells. The membranes were hybridized at 42° C. overnight and washed under high stringency conditions. X-ray film, exposed at −70° C. overnight with an intensifier screen, was used to detect the hybridized DNA. Plasmids, which hybridized strongly with the $^{32}$P-labeled CD34+/CD38− cDNA but not with the $^{32}$P-labeled CD34+/CD38+ cDNA, were sequenced.

"Virtual" Northern Blots

Double stranded cDNAs synthesized from a new preparation of Lin-, CD34+/CD38- (39,000 cells) and Lin-, CD34+/CD38+ (410,00 cells) were electrophoresed on 1% agarose gel and transferred to nitrocellulose membranes. Five replicate membranes were prepared and these were hybridized with the probes prepared from each of the cDNAs that appeared to be differentially expressed on the basis of the screening assay described above.

Northern Analysis and Dot Blots

Multiple Tissue Northern Blot™ and Human RNA Master Blot™ membranes were purchased from Clontech. Hybridizations were performed with ($\alpha$-$^{32}$P)dATP labeled probes that also contained a modified dCTP that facilitates removal of the hybridized probe so that the blot can be hybridized repeatedly (Strip-ez™, Ambion Inc, Austin Tex.). The Master Blots, as provided by the manufacturer, include 16 RNAs from regions of the central nervous system. Results are only shown from whole brain, medulla and spinal cord. The images obtained after scanning the autoradiographs of the blots from these tissues (samples D6, D7 and D8 of FIGS. 3B–3D) were moved to the positions shown in the figure.

Ribonuclease Protection Assay $^{32}$P-UTP labeled probes were transcribed using T7 RNA polymerase from double stranded DNA templates. For hybridization, 1 ug of total RNA was dried, dissolved in hybridization buffer and mixed with the labeled probe (600,000 cpm/sample). The samples were denatured at 90° C. and then hybridized at 56° C. overnight. The unhybridized RNA was digested with a mixture of RNases A and T1. After hybridization and RNase digestion the samples were treated with proteinase K, extracted with phenol, ethanol precipitated and dried. They were analyzed by electrophoresis in a standard acrylamide sequencing gel and the protected sequences were detected by autoradiography. The C23 probe was prepared by amplifying a 150 bp cDNA from original isolate.

Sense Primer 5'-AGGGAATGTAACCCTTCTCA-3' (SEQ ID NO:5)

Anti-Sense Primer 5'-TCTTACTAGATGCAGTGACC-3' (SEQ ID NO:6)

The resultant cDNA was then unidirectionally ligated into pCR3.1 TA vector and linearized with EcoR1. A ribosomal 18s probe (PTRI RNA18s), purchased from Ambion, was used to normalize the quantity of material applied to each lane of the gel. The protected fragment is 80 bp long.

RT-PCR

The expression of C21 and C12 mRNA by human leukemic cell lines was measured by RT-PCR. The RNAs were reverse transcribed with MMLV-RT using oligo (dT) to prime the reaction. For C21, the full 1548 bp ORF was used as a template in the subsequent PCR, while for C12 a 500 bp fragment was used. The primers used were:

C21 sense GATGAGTATAAGCAGTGATGT (SEQ ID NO:7)

antisense CTATTTTTGTTCTTTCCGAAGGTCTAATA (SEQ ID NO:8)

C12 sense CAACAGAGCTTCACTTTACCC (SEQ ID NO:9)

antisense CTAGGGATGGTTTCCATGA (SEQ ID NO:10)

The Both PCR reactions were performed using the following conditions: 1 minute at 94° C. followed by 30 cycles of 30 seconds at 94° C., 30 seconds at 58° C., and 2 minutes at 72° C. The PCR products were diluted and electrophoresed in agarose containing ethidium bromide.

Sequence Analysis

Plasmid DNA was sequenced by the chain termination method in the Core Sequencing Facility of Kaplan Cancer Center using an Applied Biosystems automated sequencer. The resulting sequences were analyzed using software provided by Research Computing Resources of the Kaplan Comprehensive Cancer Center.

Results

Lin-/CD34+/CD38- and Lin-/CD34+/CD38+ cells were purified as described in the Materials and Methods section and used to prepare the cDNA library. The subtracted, normalized PCR-amplified difference product was TA cloned into pCR2.1 to produce a plasmid library. The library was plated, and individual colonies isolated and expanded. Forty insert-containing clones were analyzed. Four clones were obtained that reacted predominantly with the tester cDNA and probes were synthesized from these. FIG. 2A shows "virtual" Northern blots produced by hybridizing these probes with cDNA produced from Lin- CD34+/CD38- and CD34+/CD38+ BMC. FIG. 2B shows the results of RT-PCR to amplify defined sequences from each of the four messages, under conditions in which the amount of product produced is proportional to the quantity of message present. The mRNA for CD38 was also amplified to provide a non-serological indication of the purity of the Lin, CD34+/CD38- cells.

Clone C40 contained a 352 bp DNA fragment. Its sequence is identical to nucleotides 1192–1538 of the protein phosphatase CL100 (EMB#X68277). In view of this large region of sequence identity, it was concluded that the CL100 was the differentially expressed message identified by C40 and no further analysis was attempted. The other three isolates did not correspond to known protein sequences. All of them were homologous to EST sequences present in public domain sequence databases.

C23 was originally isolated as a 178 bp fragment that was identical to nucleotides 804–981 of a 1896 bp sequence obtained from a fetal brain library (#U90916). It is also homologous to several smaller EST sequences. No protein homology was detected. A probe, prepared from C23, hybridized with RNA from human spleen and cDNA prepared from this splenic RNA was used to sequence and identify the gene. Sequential 5' and 3' RACE using the sequence of the original fragment to design primers, confirmed the EST sequence. In addition ~2 kb of new sequence was determined. No homology to any functional gene was found until >4000 bp was sequenced. Sequencing the 5' end of a 5' RACE product demonstrated that C23 is a member of the LDLR family. Subsequent sequencing indicated that it is identical to an unusual member of the LDLR family, LR11 (Yamazaki et al, 1997; Novak et al, 1996).

Dot blots with RNA from a wide range of human tissues show that C23 is widely expressed and is highly expressed in fetal tissues (FIG. 3A). The highest level of expression was found in neural tissue, liver, pituitary and peripheral WBC. Significant expression was also detected in hematopoietic tumor cell lines such as CHRF, Raji, KG1, and U937 but not in K562 (data not shown). RNase protection analysis demonstrated that C23 was highly expressed in neutrophils and could be detected in lymphocytes (FIG. 4A).

C21 was originally isolated as a 201 bp fragment. No protein homology was detected. This fragment was used to probe a placental cDNA library and a 2209 bp fragment was identified and sequenced. cDNA prepared from the K562

RNA was used to sequence the remainder of C21. Using both 5' and 3' RACE, a poly A region of this cDNA and a complete open reading frame were identified. The 3596 bp sequence is shown in FIGS. 5A–5B, and the sequencing strategy used to characterize this gene is shown in FIG. 6B. The 3'-UTR encoded in this ORF is >2000 bp. The cDNA encodes a previously unknown member of the WD-40 family (Neer et al, 1994). At the nucleotide level, the sequence has 79% identity across the open reading frame to *Homo sapiens* mRNA for transducin (beta)-like 1 (TBL1) (#Y12781) (Bassi et al, 1999) and 68% homology to ebi, a *drosophila* nuclear protein (Dong et al). Prosite analysis detected four WD-40 repeats within the ORF.

A dot blot (FIG. 3B) shows that the product of this gene is expressed widely and the virtual Northern blot shown in FIG. 2A indicates that it is preferentially expressed in the CD34+/CD38− population, and it appears to be a highly expressed gene. RT-PCR using primers that flanked the ORF, amplified a 1548 bp cDNA from mRNA templates extracted from the human leukemic cell lines CHRF, Jurkat, HL60, K562, U937 and Raji (FIG. 4B). On Northern blots, a probe encoding the ORF, hybridized with 4.3 kb and ~7.8 kb messages in RNAs extracted from a variety of sources, including the human leukemic cells (data not shown).

C12 was originally isolated as a 267 bp fragment that is homologous to several ESTs. No protein homology was detected. A virtual Northern blot (FIG. 2A) confirmed that this gene is differentially expressed in the CD34+/CD38− population. It, too, has a relatively wide tissue expression (FIG. 3C) with the highest levels occurring in adult adrenal gland, heart, stomach and liver. Among the hematopoietic organs, both adult bone marrow and thymus had significant levels. Using RNA from a Jurkat cell library, ~1 kb of cDNA that appears to be the 3' end of the molecule was sequenced. The laboratory of the present inventor has been unable to obtain a sequence encoding an open reading frame using either 5' extension of the original sequence or by using this sequence as a probe with a placental cDNA library. However, since an RNase protection assay, using the original C12 isolate as a probe, protected the appropriately sized fragment when hybridized with RNA isolated from K562 (data not shown) and RT-PCR amplified a cDNA of the correct size from the panel of human leukemic cells, it is expected that this is an expressed message and not a cloning artifact.

Discussion

The molecular processes that maintain the stem cell pool are largely unknown. Understanding this process requires identifying the unique attributes of PHSC. Because of their rarity, molecular characterization of PHSC has been difficult to achieve. Much of what has been accomplished has been directed towards analyzing the temporal expression of genes that are known to play a role in various aspects of hematopoiesis. Primary cultures of hematopoietic progenitors and developing embryonic stem (ES) cells express cytokine and growth factor receptors and transcription factors known to be important in hematopoiesis (Cheng et al, 1996; Keller et al, 1993; Orlic et al, 1995). These studies have been extended to the single cell level and expression by "sister" pairs of cells has been studied (Brady, 1993). Targeted deletion of several transcription factors known to be active in hematopoietic cells results in failure of either primary or definitive hematopoiesis (Zhang et al, 1998b; Simon, 1998; Meyer et al, 1998; Lessard et al, 1998; Neubauer et al, 1998; Okuda et al, 1998).

cDNA libraries prepared from enriched stem cell preparations have been used to identify genes uniquely expressed by stem cells or single CD34+/CD38− cells. Tyrosine kinases and phosphatases that are differentially expressed in early hematopoietic cells (Hoehn et al, 1996; Bierhuizen et al, 1997; Dosil et al, 1996) have been found by using degenerate PCR. Tnk-, a tyrosine kinase gene, was isolated from CD34+/CD38− derived mRNA (Hoehn et al, 1996) and a similar strategy was used to identify FLP-1 (Fetal Liver Phosphatase (Dosil et al, 1996).

The laboratory of the present inventor has extended the search for genes that are differentially expressed in PHSC by using PCR-driven subtraction and has identified four mRNAs that are differentially expressed by Lin−, CD34+/CD38− cells. None of these genes encode a message whose expression is limited to PHSC. All of them are expressed in a variety of tissues, suggesting that they are involved in processes that are important to many cell types and not just hematopoietic cells. To date, none of the efforts to identify a gene uniquely expressed by PHSC have been successful. Such hematopoietic, stem cell-specific regulatory genes may be very rare or perhaps do not exist. Stem cells, regardless of the function of their differentiated progeny, share many characteristics. They are self-renewing, but rarely actively proliferating; they are protected from toxic agents in their environment and finally, they are isolated from excessive stimulation by environmental factors that might otherwise deplete the stem cell pool. These properties are not unique requirements for cells of the hematopoietic lineage. Furthermore evidence has accumulated suggesting that the plasticity of stem cells is far greater than previously believed (Lemischka, 1999). Cells derived from muscle and brain have been shown to be capable of developing into hematopoietic cells (Jackson et al, 1999; Bjornson et al, 1999) and bone marrow derived cells have been shown to give rise to hepatocytes (Theise et al, 2000) and myoblasts (Gussoni et al, 1999). How the fate of any of these cells is determined remains unclear.

One of the genes that is shown to be differentially expressed in CD34+/CD38− cells, clone C40, is identical to CL100 (Alessi et al, 1993). In the bone marrow, CL100 is expressed by CD34+/CD38− cells, and it could not be detected in mature hematopoietic cells. It is a member of the subfamily of protein phosphatases that exhibits dual substrate specificity for phosphotyrosine and phosphoserine/threonine residues in proteins and is related to the late H1 gene of vaccinia virus. The CL100 phosphatase, expressed and purified in bacteria, inactivates recombinant MAP kinase in vitro by the concomitant dephosphorylation of both its phosphothreonine and phosphotyrosine residues. Deactivation of these signaling cascades at the MAPK level is critically dependent on dephosphorylation of the TXY motif by members of the MKP family of dual-specificity phosphatases.

Since MAP kinases play such a central role in the regulation of transcriptional activation, an enzyme activity that inactivates MAP kinase could serve to protect stem cells of any lineage from inadvertent or inappropriate activation. For example it has recently been shown that all-trans retinoic acid, which enhances the long-term hematopoietic repopulating activity of cultured hematopoietic cells (Purton et al, 2000) and delays the differentiation of PHSC (Purton et al, 1999) increases the levels of the mouse orthologue of CL100 (MKP-1) (Lee et al, 1999). MKP-1 also plays a role in maintaining quiescence in smooth muscle cell and is downregulated when proliferation is induced (Lai et al, 1996). In rat arterial smooth muscle cells over expressing MKP-1, growth was arrested in the G1 phase and entry into the S phase was blocked. Similarly, MKP-1 is constitutively expressed on myoblast C2C12 cells, but when these cells are transferred to differentiation medium, expression declines (Bennett et al, 1997). These results suggest that CL100 may play an important role in maintaining stem cells in a quiescent state and protecting the stem cell pool from depletion.

C23 is identical to LR11 (gp250), an unusual member of the Low Density Lipoprotein Receptor family (Novak et al, 1996; Horn et al, 1997; Jacobsen et al, 1996); Yamazaki et al, 1996). This growing family of receptors transports macromolecules into cells by receptor mediated endocytosis. The family members bind a wide range of unrelated ligand and it is not known if all of this binding is functionally significant. LR11 is unusual in that in addition to 11 ligand-binding repeats, it contains a series of fibronectin type III repeats near its carboxyl-terminal end which are similar to those found in cytokine receptors Yamazaki et al, 1997). It is highly expressed in brain but hematopoietic expression has not been reported. In the peripheral blood, neutrophils are the predominant source of mRNA for LR11. Among the striking properties of LR11 is its high degree of structural conservation (>80% identity among mammals). It is also unusual in that its expression is unaffected by cholesterol and estrogen. The 178 bp fragment that was cloned here is part of a 4145 bp 3' UTR that had not been previously sequenced. This is among the largest known human 3' UTRs Pesole et al, 1998).

C21 encodes a previously unknown gene that is a member of the WD-40 family (Neer et al, 1994). This mRNA is expressed widely but the most striking feature of our survey of the expression of this gene is the high level detected in fetal tissues (FIG. 3B, row E). The WD-40 group is a large family of proteins, all of whom appear to be regulatory in function. It is believed that the WD-40 repeats mediate protein—protein interactions and are likely to play a role in the control of cytotypic differentiation. None have known enzymatic activity. Members of the family are involved in signal transduction, RNA processing, gene regulation, vesicular trafficking and cytoskeletal assembly. There are also several members of the family whose function is unknown. The two orthologues of C21 belong to this group with no known function. The fly orthologue of C21, ebi (Dong et al, 1999), encodes an evolutionarily conserved protein with a unique amino terminus, distantly related to F-box sequences, and tandemly arranged carboxyl-terminal WD40 repeats. Genetic evidence indicates that ebi is involved in EGF receptor signal transduction. The human orthologue, TBL1 (Bassi et al, 1999), has no known function but is associated with X-linked late-onset sensorineural deafness.

As noted above LR11 has a 4145 bp 3' UTR. Both C21 and C12 also have 3' UTRs that exceed 2000 bases and the published sequence of CL100 has a 3' UTR of >700 bp but may be considerably longer since the single AATAAA sequence in the 3' UTR may not be an authentic polyadenylation site (Salamov et al, 1997). The mean 3' UTR length for all human cDNAs deposited in public databases is 740 bp (Pesole et al, 1998). Although the probability of selecting four genes at random and having all of them exceed the mean is fairly large (0.16), if 3' UTR length is normally distributed, the probability of three of the four having 3' UTRs that exceed the mean by 3–5 fold is extremely small. The results suggest that long 3' UTRs are in some way characteristic of genes expressed by developing hematopoietic cells. The role of 3' UTRs in the regulation of gene expression is less well understood than that of 5' UTRs. Both cis- and trans-acting regulatory effects have been described. 3' UTRs can affect gene expression by influencing the localization, stability and translation of mRNAs. Sequence length as well as structure seem critical. A series of structural motifs that influence RNA stability, etc. have been described (Pesole et al, 2000) but none of these are present in the sequences that are reported here. The diverse roles of 3' UTRs have been reviewed in Decker et al (1995) and Rajagopalan et al (1997). The differential expression of these genes by immature hematopoietic cells, in contrast to more mature cells, suggests that these long 3' UTRs may be characteristic of genes that play a regulatory role during development.

EXAMPLE 2

Isolation of C21

C21 was identified in a cDNA library prepared by subtractive hybridization between CD34+/CD38– and CD34+/CD38+ BMC in an attempt to identify genes expressed in the earliest stages of hematopoietic differentiation. To determine if the human cDNA could actually be translated into a protein, the laboratory of the present inventor used it in an in vitro translation system and the results are shown in FIG. 7. The product produced from the cloned cDNA encodes a protein which has the predicted molecular mass of 56–57 kDa. The homologous mouse gene was also identified.

Genomic Structure of Human hC21

C21 is located on chromosome 3 between 3q26 and 3qter. The gene occupies ~100 Kb and the coding structure is assembled from 14–16 small exons. The translational start site is located in the $3^{rd}$ exon and is 50 kb downstream from the first exon. The mouse sequence (SEQ ID NO:11), which encodes the amino acid sequence of mouse C21 (SEQ ID NO:12) also is assembled from 16 exons but the full intronic sequences are not yet known.

Expression of C21

To facilitate analyzing the expression of the C21 proteins, the deduced peptide sequences were used to prepare anti-peptide antibodies directed against the non-identical portions of the two isoforms. Two rabbits were immunized with each of the carboxyl terminal peptides of C21α and C21β. The deduced sequences of the C-terminal peptides are shown below.

C21 α TQTGALVHSYRGTGGIFEVCWNA(C)AGDKV-GASASDGSVCVLDLR (SEQ ID NO:17)

C21 β TQVCLHYLNGQVLLNLGRSICLYTLPHHLV-VIPLVALIELLVLK (residues 471 to 514 of SEQ ID NO:4)

Figures 8A, 8B, 8C, 8D:
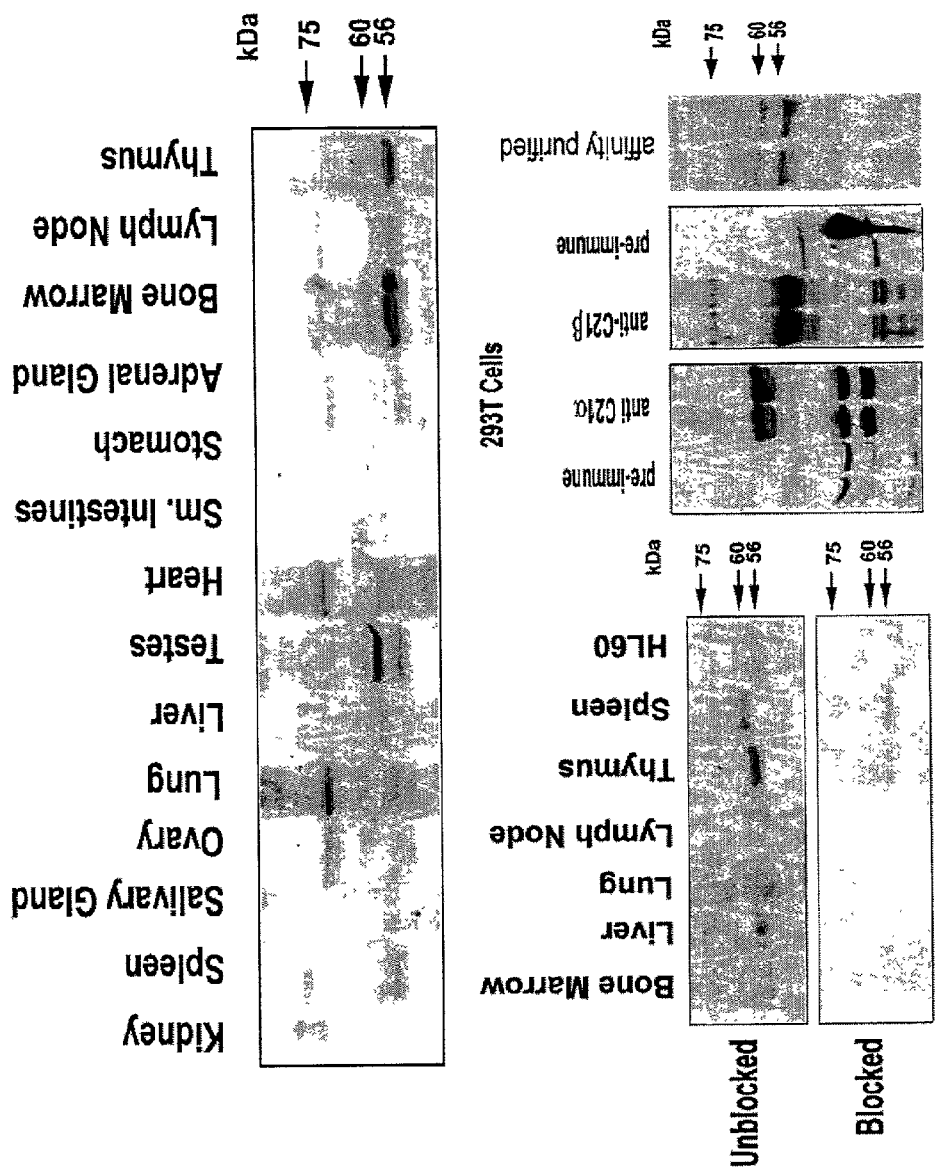

The rabbits were immunized with the peptides having the sequence shown in bold face above coupled to ovalbumin in Freund's Adjuvant (CFA) and boosted with the same antigens in Incomplete Adjuvant every 2 weeks for a total of 4 injections. Antibody titers were measured by ELISA using both the immunizing peptide and the recombinant C21. Since the peptide used to produce the antibody for C21α is identical to the homologous peptide found in TBL1, the necessary specificity could not be demonstrated. Therefore, a new antibody directed against the region of C21 (amino acids 117–125 of SEQ ID NO:2) that differed most from TBL1 was prepared. The resultant antibody was then absorbed with a peptide, CGVSHQNPSK-amide (SEQ ID NO:13) coupled to acrylamide, representing the equivalent sequence in TBL1, to further reduce the possibility of cross-reactivity. The resultant antibody was then affinity purified using the immunizing peptide. The site recognized by this antibody is 30 amino acids downstream of the putative F-box in the amino terminal half of C21. FIGS. 8A–8D shows Western blots obtained with these antibodies. The anti-C21 β antibodies consistently detect a single band with the molecular mass (~56 kD) predicted by the sequence of the ORF (FIG. 8A). Both the new affinity purified antiserum and the anti-C21α antiserum identify the same 56 kDa peptide, but they produce more complex patterns that vary from tissue to tissue. Additional components are found at ~60 kDa and ~75 kDa (FIGS. 8B–8C). The addition of soluble peptide to the diluted antiserum inhibited the staining of all three bands by the affinity-purified antibody (FIG. 8B). In bone marrow the predominant form is the 56 kDa peptide. Cell lines (293T and HL60) express readily detectable quantities of C21. In general, in these cell lines only a single major band is detected. The results obtained with 293T cells are particularly striking since anti-C21α produces a single band at ~60 kDa, while anti-C21β detects only a smaller band at 56 kDa (FIG. 8C). The results obtained with the affinity purified antibody are shown in FIG. 8D, where this antibody, specific for C21, is directed at an epitope shared by both isoforms and detects both bands. The results in FIGS. 8C and 8D are particularly informative since they: 1) prove that more than one form of C21 exists, 2) show that the β-isoform identified by 5' RACE encodes an expressed protein, 3) show that a single cell type produces more than one isoform, 4) demonstrate that the higher molecular weight form detected by the antibody to the C-terminal fragment of the α form is C21 and not TBL1 (since the peptide used for the immunization of the animals that made the affinity absorbed antibody is not present in TBL1), and, finally, 5) they confirm the specificity of the staining shown in FIGS. 9A–9H.

C21 Expression in Normal Human Tissues

C21α and C21β are expressed by hematopoietic cells in adult bone marrow and fetal liver (FIGS. 9A–9D). C21α, the isoform originally detected in the subtracted library, stains fetal liver hematopoietic cells with far greater intensity than does C21β. The reverse is true in adult bone marrow where C21α stains a very small fraction of the cells (<0.5%) while C21β stains ~5% of the cells with high intensity (FIGS. 9C–9D). These results indicate that the expression of the two isoforms is developmentally regulated and suggest that there is a reciprocal relationship between the expression of the α-isoform that is prominent in fetal tissues and the β-isoform that is more highly expressed in the adult. Pre-immune serum from these rabbits did not stain these hematopoietic cells (FIGS. 9E–9H) and the staining that was observed was blocked by incubating the diluted antiserum (1:200) with the immunizing peptide (1 ug/ml; data not shown). Both C21α and C21β stain distal convoluted tubules and collecting ducts in adult kidney, but neither stains fetal kidney (data not shown). C21β selectively stains the capillary endothelium of the glomeruli while C21α does not. Antibodies to both isoforms also stain a small number of other normal tissues. These include Paneth cells in the stomach and Leydig cells and primary spermatogonia in the testis. No staining was observed with parenchymal cells of the heart, lung, brain, liver, small and large intestines and pancreas.

Expression of C21 at the mRNA level has also been detected. Semi quantitative RT-PCR showed that C21 was expressed at high levels in CD34+/CD38– cells (data not shown), and cell lines derived from human hematopoietic tumors (FIG. 4B) (Neer et al, 1994). Northern analyses produced a more complicated result. A probe from the 3' untranslated region detected a 7.3 kb transcript in many tissues. The expression of this 7.3 kb message does not correlate with the pattern of protein expression shown in FIGS. 8A–8D, suggesting that this message is either not translated into protein (possible unspliced) or that its protein product is extremely unstable and therefore present at very low steady state levels. Hybridization with a probe restricted to the open reading frame (ORF) revealed a different pattern. It is shown on the lower half of FIG. 10. In addition to the 7.3 kb band there is an abundant 4.7 kb message that is expressed predominantly in hematopoietic tissues and appears to correlate with the protein patterns shown above. Mouse tissues show a similar pattern.

Effect of Over-Expression of hC21α in Mouse Fibroblasts

Two clones of C21-3T3 (21.9 and 21.5) were selected for study. Both ribonuclease protection assays (FIG. 11A) and Western blotting (FIG. 11B) showed that the transfected cells were actually expressing C21. The probe used in the RPA to demonstrate the expression of the human mRNA was selected so that the human product could be distinguished from the endogenous mouse message. The protected fragment is 180 bp. The anti-C21α peptide antiserum used in the Western blot is directed against a region of the molecule that is identical in man and mouse. Since 3T3 cells express mouse C21 and this has the same MW as the human protein, only quantitative differences could be demonstrated.

The transfected 3T3 cells showed a dramatic alteration in their growth properties. They did not show altered cell-cycle parameters. The proportion of cells in S phases in exponentially growing cells and in cells approaching their saturation density is the same. What was striking was differences in the plating efficiency of the transfected and control cells. The control 3T3 cells, grown in 5% bovine serum, plate with an efficiency of ~20%. In the same medium, transfected cells plate at 3–5 fold higher efficiency. There are no differences in either the rate of attachment or the degree of spreading of the transfected cells compared to the controls. If, however the cells are maintained in suspension before plating, the control cells die more rapidly than the C21 transfected cells, suggesting that C21α might increase the plating efficiency of the transfected cells by protecting them from apoptosis. Direct testing confirmed this hypothesis. The rate of apoptosis in cells grown under conditions of serum starvation was measured. An example of the results is shown in FIGS. 12A and 12B. PI staining of DNA was used as a marker of cell death. Annexin V, which stains phosphatidyl serine after it is translocated to the exterior surface of the cell membrane, was used to measure apoptotic cells. Cells in the lower right quadrant have initiated the apoptotic cascade and are stained with Annexin V but have not lost membrane integrity and so do not stain with PI. The effect of this resistance is to prolong the survival of cells in a hostile environment. The proportion of live cells after 24 hours of serum starvation is more than 50% greater in the cells over-expressing C21 than in the control cells. The reduction in apoptotic cells accounts for all of the increased survival. The protection is not permanent and by 48 hours, the effect on viability became marginal but the number of apoptotic cells was still reduced. By 72 hours, the differences were lost. Thus, over-expression of C21α delays, but does not prevent apoptosis in 3T3. This is consistent with the suggestion that the mechanism through which C21 acts to delay apoptosis is the stabilization of an NHR-co-repressor complex.

Influence of Apoptotic Signals on the Intracellular Localization of C21

To determine the intracellular localization of C21, the anti-peptide antibodies described above were used in an indirect immunofluorescence assay. The results are shown in FIG. 13. C21α stains 3T3 more brightly than C21β. The staining is primarily cytoplasmic (FIG. 13, row 2). After treatment with CPT (row 1), the intensity of the staining increased. Both cytoplasmic (with perinuclear intensification) and nuclear staining increased. In serum-starved cells, staining with both antibodies became predominantly nuclear. The increase in nuclear staining suggests that under conditions of stress C21 levels increase, and suggests a physiologic role for C21 in the response to these apoptotic stimuli.

Transgenic Mice

Because C21 is expressed at high levels in fetal hematopoietic tissues and in cell lines originating from hematologic malignancies, it was thought important to examine the effects of over-expression of C21 in hematopoietic cells. The consequences of over-expression of human C21 in mice have begun to be examined using transgenic technology. The hC21α transgene, after transfer to the HS/vav vector was excised, purified, and introduced into the inbred C57BL/6J mouse genome by pronuclear microinjection. To make HS/vav C21, it was necessary to eliminate the two HinDIII sites from the hC21 cDNA. The variant was made by PCR-based silent mutagenesis in which caagcttatagagataagcttgca (SEQ ID NO:14) was changed to caggcttatagagataaacttgca (SEQ ID NO:15). The mutant hC21 cDNA was then digested with BamHI and NotI and ligated into the pcDNA4 HIS vector. The DNA sequence was determined and protein expression was confirmed. The cDNA containing hC21 mutant sequence, an upstream translation enhancer and the HIS tag sequence was re-amplified by PCR using proof reading enzyme using pCDNA 4–21 mutant vector as a template and ligated into a blunted HS/vav vector (Ogilvy et al, 1999). The orientation of the insert was determined by analyzing the results of a digestion with Sal1. Plasmids with the correct insert were used to prepare the DNA for blastocyst injection into the inbred C57BL/6J mouse genome by pronuclear microinjection.

Transgenic pups were identified by PCR on tail DNA, by using primers specific to the SV40 pA sequence. Both of the original pups were females and so additional breeding was required before homozygous recombinants could be obtained. Several litters have now been obtained. The homozygotes are viable but 4-week-old animals have distinctly abnormal white counts. Granulocytes are present in normal numbers but do not mature normally. Segmented neutrophils are reduced by almost 90%. These results are summarized in Table 1 below. Only male mice have been used since the Jackson labs indicate that there is a sex difference in the proportion of granulocytes (males=28.8±2.8: females=16.6±2.3)I n C57B1/6 mice. The results demonstrate that over-expression of C21α has a profound effect on granulocyte development. The smears of these mice resemble those reported for mice in which the RAR gene was knocked out. Myeloid progenitors (Colony-forming Units; CFU) including G, GM and GEMM colonies are present in these mice but enough animals have not been examined to determine their frequency.

TABLE 1

Differential Counts of Peripheral Blood WBC in C21 Transgenic Mice

| | | Segmented PMN | Immature Neutrophils | LYMPH | MONO | EOS | BLASTS |
|---|---|---|---|---|---|---|---|
| C21 TRANSGENIC | mean | 10.1 | 18.3 | 61.7 | 4.9 | 1.2 | 4.7 |
| | S.D. | 4.8 | 2.6 | 6.6 | 1.5 | 0.8 | 3.8 |
| WILD TYPE | mean | 30.8 | 6.6 | 58.0 | 5.6 | 0.8 | 0.0 |
| | S.D. 7.3 | 2.4 | 9.2 | 1.5 | 0.3 | 0.0 | |

Interaction of C21 with Transcriptional Regulators

The interaction of C21 with components of the transcription regulatory complex can be demonstrated by both GST "pull-down" and co-precipitation.

GST Pull-Down

Labeled C21 prepared by in vitro translation using $^{35}S$ methionine can be "pulled-down" by immobilized SMRT. As shown in FIG. 14A, full-length C21 is pulled down by GST SMRT but does not bind to a control GST column. Truncated forms of C21 lacking the F-Box ([δF-box]) or just the N-terminal 40 amino acid (21[δN]) are not pulled down by GST-SMRT (FIG. 14B) indicating that both the putative F-box and the N-terminus are critical for the high affinity interaction of C21 with SMRT. A fragment (21[δC]) consisting only of the first 230 amino acids (i.e., lacking all of the WD40 repeats and the carboxyl terminus) was as efficient as the full-length protein in reacting with SMRT. These results not only demonstrate the importance of the N-terminal end of C21 for the interaction with the co-repressors, but highlight the importance of identifying the protein(s) that react with the WD-40-rich carboxyl end of C21.

Co-Precipitation of C21 with HDAC

FIG. 15 shows that C21 associates with HDAC3. In this experiment the cells were transfected with HDAC and C21. The HDAC3 in both lysates was adsorbed to Ni-agarose columns. When present C21 binds to the bound HDAC. The flag-tagged C21 does not bind to Ni-agarose columns that have not bound HDAC. While these data do not show a direct interaction between C21 and HDAC, they demonstrate a complex containing HDAC, will bind C21 when both proteins are expressed in the same cells.

Effect of Co-Transfection of C21 on SMRT Expression

SMRT expression is greatly increased in cells expressing both SMRT and C21. Truncated forms of C21 (21[δC] and 21[δN+F-box]) are more effective than the wild type molecule (FIG. 16). These results indicate that the mechanism by which C21 increases SMRT expression is complex. They provide evidence that C21 is serving some adaptor function, linking two molecules, whose interaction regulates SMRT expression. Elimination of either end ("docking site") creates molecules that interfere with this regulation and lead to large increases in C21 expression. The effect is seen with the fragment that binds SMRT (21[δC]) and one that has no affinity for SMRT (21[δN+F-box]). However, since co-transfection with the wild type C21 also leads to a significant increase in SMRT expression, it appears that the region between amino acids 80 and 175 may also play an autonomous role increasing SMRT expression. If this is correct, then it is likely that primary role of C21 is the regulation of proteasomal targeting and that the amino terminal end docks the molecule to the co-repressor; the central portion interacts with the ubiquitination pathway and the carboxy-terminal provides tissue specific activation.

The expression of the C21 mutants varies considerably. The most protection was produced by co-transfection with C21δNf, which was also the most highly expressed C21 protein. However the next most effective protein was C21δC which was the least expressed of the three C21 proteins. Co-transfection with siah-1, a factor known to contribute to the targeting of N-CoR for proteolytic destruction did not affect SMRT expression. COS 7 cells were co-transfected with pCDNA His-SMRT (1-300) and the His-tagged C21 constructs described above. Control cells were transfected with pCDNA His-SMRT (1-300) and an empty vector.

Effect of Co-Transfection of C21 on SMRT Stability

Co-transfection of C21 with SMRT retards the degradation of SMRT. The results of a pulse-chase experiment showing this are in FIG. 17. In control 293T cells the $^{35}$S SMRT is undetectable after 3 hours and barely detectable after 1 hour, while in cells transfected with C21, labeled SMRT was easily detected throughout the experiment. The difference in the intensity of the labeling at 0 time reflects the instability of the labeled SMRT in the control cells. Much of the material labeled during the pulse is degraded during the labeling period. The band marked *** is an unknown protein that co-purified with SMRT. The label in this protein is stable and the intensity of the band serves as an internal control for loading etc.

Effect of Proteasome Inhibitors on SMRT Expression

To demonstrate the levels of SMRT found in COS 7 cells are controlled by ubiquitination the transfected cells were treated with MG132 in DMSO or with DMSO as a control and the level of SMRT was measured by Western blotting as described above. MG 132 (N-CBZ-Leu-Leu-Leu-al) is a potent, membrane-permeable proteasome inhibitor (Lee et al, 1998). To control for differences in cell survival etc., the COS cells were co-transfected with a vector that expressed His-GFP along with the His-SMRT vector. GFP is not degraded via the ubiquitin-proteasome pathway. As shown in FIG. 18, MG132 treated COS7 cells express levels of SMRT that are ~25 times those found in the DMS) control. Only a small difference in GFP expression was observed.

In summary, the present inventor has identified C21 as a novel transcriptional regulator. The gene encoding this protein has been cloned and identified as a member of a small family of proteins that include at least two isoforms encoded by the same gene and another X-linked protein called TBL1. The family members interact with the co-repressors that regulate the activity of hormone-dependent, nuclear transcription factors. The evidence suggests that these proteins act by altering the stability of the co-repressor complex and that they may also contribute, or recruit other proteins that provide, an autonomous repressor function. The functional effects of altering C21 expression are likely to alter many aspect of cellular metabolism. When over-expressed in hematopoietic cells, C21α alters the pathway of myeloid differentiation, inhibiting the formation of mature granulocytes. When over-expressed in fibroblasts, C21 inhibits the apoptotic response.

Having now fully described this invention, it will be appreciated by those skilled in the art that the same can be performed within a wide range of equivalent parameters, concentrations, and conditions without departing from the spirit and scope of the invention and without undue experimentation.

While this invention has been described in connection with specific embodiments thereof, it will be understood that it is capable of further modifications. This application is intended to cover any variations, uses, or adaptations of the inventions following, in general, the principles of the invention and including such departures from the present disclosure as come within known or customary practice within the art to which the invention pertains and as may be applied to the essential features hereinbefore set forth as follows in the scope of the appended claims.

All references cited herein, including journal articles or abstracts, published or corresponding U.S. or foreign patent applications, issued U.S. or foreign patents, or any other references, are entirely incorporated by reference herein, including all data, tables, figures, and text presented in the cited references. Additionally, the entire contents of the references cited within the references cited herein are also entirely incorporated by references.

Reference to known method steps, conventional methods steps, known methods or conventional methods is not in any way an admission that any aspect, description or embodiment of the present invention is disclosed, taught or suggested in the relevant art.

REFERENCES

Alessi et al, "The human CL100 gene encodes a Tyr/Thr-protein phosphatase which potently and specifically inactivates MAP kinase and suppresses its activation by oncogenic ras in Xenopus oocyte extracts", Oncogene 8:2015–2020 (1993)

Bassi et al, "X-linked late-onset sensorineural deafness caused by a deletion involving OA1 and a novel gene containing WD-40 repeats", Am J Hum Genet 64:1604–1616 (1999)

Bennett et al, "Regulation of distinct stages of skeletal muscle differentiation by mitogen-activated protein kinases", Science 278:1288–1291 (1997)

Better et al, "Escherichia coli secretion of an active chimeric antibody fragment", Science 240:1041–1043 (1988)

Bierhuizen et al, "Green fluorescent protein variants as markers of retroviral- mediated gene transfer in primary hematopoietic cells and cell lines", Biochem Biophys Res Commun 234:371–375 (1997)

Bjornson et al, "Turning brain into blood: a hematopoietic fate adopted by adult neural stem cells in vivo", Science 283:534–537 (1999)

Boulianne et al, "Production of functional chimaeric mouse/human antibody", Nature 312:643–646 (1984)

Boulton et al, "A role for ebi in neuronal cell cycle control", EMBO J. 19:5376–5386 (2000)

Brady et al, "Construction of cDNA libraries from single cells", Methods Enzymol 225:611–23 (1993)

Burke et al, "Co-repressors 2000" FASEB J 14:1876–1888 (2000)

Cabilly et al, "Generation of antibody activity from immunoglobulin polypeptide chains produced in Escherichia coli", Proc Natl Acad Sci USA 81:3273–3277 (1984)

Capel et al, "Long- and short-lived murine hematopoietic stem cell clones individually identified with retroviral integration markers", Blood 75:2267–2270 (1990)

Chen et al, "A transcriptional co-repressor that interacts with nuclear hormone receptors", *Nature* 377:454–457 (1995)

Cheng et al, "Temporal mapping of gene expression levels during the differentiation of primary hematopoietic cells", *Proc Nat Acad Sci USA* 93:13158–13163 (1996)

Chomczynski et al, "Single-step method of RNA isolation by acid guanidinium thiocyanate-phenol-chloroform extraction", *Anal Biochem* 162:156–159 (1987)

Ciechanover A "The ubiquitin-mediated proteolytic pathway," *Brain Pathol* 3:67–75 (1993)

Colligan et al, *Current Protocols in Immunology*, Green Publishing Assoc., and Wiley Interscience, New York (2001)

Decker et al, "Diversity of cytoplasmic functions for the 3' untranslated region of eukaryotic transcripts", *Curr Opin Cell Biol* 7:386–392 (1995)

DeSalle et al, "Regulation of the G1 to S transition by the ubiquitin pathway", *FEBS Lett* 490:179–189 (2001)

Dong et al, "ebi regulates epidermal growth factor receptor signaling pathways in *Drosophila*", *Genes Dev* 13:954–965 (1999)

Dosil et al, "Cloning and characterization of fetal liver phosphatase 1, a nuclear protein tyrosine phosphatase isolated from hematopoietic stem cells", *Blood* 88:4510–4525 (1996)

Eaves et al, "The human hematopoietic stem cell in vitro and in vivo", *Blood Cells* 18:301–307 (1992)

Eshhar et al, "Chimeric T cell receptor which incorporates the anti-tumour specificity of a monoclonal antibody with the cytolytic activity of T cells: a model system for immunotherapeutical approach", *Br J Cancer Suppl*, 10:27–29 (1990)

Glotzer et al, "Cyclin is degraded by the ubiquitin pathway", *Nature* 349:132–138 (1991)

Gussoni et al, "Dystrophin expression in the mdx mouse restored by stem cell transplantation", *Nature* 401:390–394 (1999)

Graf et al, "Identification of a novel DNA sequence differentially expressed between normal human CD34+CD38'and CD34+CD38'° Marrow cells", *Blood* 86:548–556 (1995)

Grimwade et al, "The importance of diagnostic cytogenetics on outcome in AML: analysis of 1,612 patients entered into the MRC AML 10 trial. The Medical Research Council Adult and Children's Leukaemia Working Parties", *Blood* 92:2322–2333 (1998)

Gross et al, "Expression of immunoglobulin-T-cell receptor chimeric molecules as functional receptors with antibody-type specificity", *Proc Natl Acad Sci USA*, 86:10024–10028 (1989)

Guenther et al, "A core SMRT corepressor complex containing HDAC3 and TBL1, a WD40-repeat protein linked to deafness", *Genes Dev* 14:1048–1057 (2000)

Harlow et al, *Antibodies: A Laboratory Manual*, Cold Spring Harbor Laboratory, Cold Spring Harbor, N.Y. (1988)

He et al, "Distinct interactions of PML-RARalpha and PLZF-RARalpha with co-repressors determine differential responses to RA in APL", *Nat Genet* 18:126–135 (1998)

Hershko et al, "Components of ubiquitin-protein ligase system. Resolution, affinity purification, and role in protein breakdown", *J Biol Chem* 258:8206–8214 (1983)

Hochstrasser M, "Ubiquitin and intracellular protein degradation", *Curr Opin Cell Biol* 4:1024–1031 (1992)

Hodgson et al, "Properties of haematopoietic stem cells surviving 5-fluorouracil treatment: evidence for a pre-CFU-s cell", *Nature* 281:381–382 (1979)

Hoehn et al, "Tnk1: A novel intracellular tyrosine kinase gene isolated from human umbilical cord blood CD34+/Lin-/CD38–stem/progenitor cells", *Oncogene* 12:903–913 (1996)

Horlein et al, "Ligand-independent repression by the thyroid hormone receptor mediated by a nuclear receptor co-repressor", *Nature* 377:397–404 (1995)

Horn et al, "Molecular analysis of ligand binding to the second cluster of complement-type repeats of the low density lipoprotein receptor- related protein. Evidence for an allosteric component in receptor-associated protein-mediated inhibition of ligand binding", *J Biol Chem* 272:13608–13613 (1997)

Hu et al, "Transcriptional Repression by Nuclear Hormone Receptors", *Trends Endocrinol Metab* 11:6–10 (2000)

Huang et al, "Nuclear receptor corepressors partner with class II histone deacetylases in a Sin3-independent repression pathway", *Genes Dev* 14:45–54 (2000)

Jackson et al, "Hematopoietic potential of stem cells isolated from murine skeletal muscle", *Proc Natl Acad Sci USA* 96:14482–14486 (1999)

Jacobsen et al, "Molecular characterization of a novel human hybrid-type receptor that binds the alpha2-macroglobulin receptor-associated protein", *J Biol. Chem.* 271:31379–31383 (1996)

Jepsen et al, "Combinatorial roles of the nuclear receptor corepressor in transcription and development", *Cell* 102:753–763 (2000)

Jones et al, "Separation of pluripotent haematopoietic stem cells from spleen colony-forming cells", *Nature* 347:188–189 (1990)

Jordan et al, "Cellular and developmental properties of fetal hematopoietic stem cells", *Cell* 61:953–963 (1990)

Kastner et al, "Positive and negative regulation of granulopoiesis by endogenous RARalpha", *Blood* 97:1314–1320 (2001)

Keller et al, "Hematopoietic commitment during embryonic stem cell differentiation in culture", *Mol Cell Biol* 13:473–486 (1993)

Kipreos et al, "The F-box protein family", *Genome Biol* 1:REVIEWS3002 (2000)

Kohler et al, "Continuous cultures of fused cells secreting antibody of predefined specificity", *Nature* 256:495–497 (1975)

Kosugi et al, "Histone deacetylase inhibitors are the potent inducer/enhancer of differentiation in acute myeloid leukemia: a new approach to anti-leukemia therapy", *Leukemia* 13:1316–1324 (1999)

Kramer et al, "Histone deacetylase as a therapeutic target", *Trends in Endocrinology and Metabolism* 12:294–300 (2001)

Krause et al, "CD34: Structure, biology, and clinical utility", *Blood* 87:1–13 (1996)

Kurebayashi et al, "Retinoid-related orphan receptor gamma (RORgamma) is essential for lymphoid organogenesis and controls apoptosis during thymopoiesis", *Proc Natl Acad Sci USA* 97:10132–10137 (2000)

Lai et al, "Mitogen-activated protein kinase phosphatase-1 in rat arterial smooth muscle cell proliferation", *J Clin Invest* 98:1560–1567 (1996)

Lansdorp et al, "Expression of CD45 isoforms on functional subpopulations of CD34+hemopoietic cells from human bone marrow", *J Exp Med* 172:363–366 (1990) Selective Lee et al, "Proteasome inhibitors: valuable new tools for cell biologists", *Trends Cell Biol* 8:397–403 (1998)

Lee et al, "All-trans-retinoic acid inhibits Jun N-terminal kinase by increasing dual-specificity phosphatase activity", *Mol Cell Biol* 19:1973–1980 (1999)

Lemischka I, "The power of stem cells reconsidered?", *Proc Natl Acad Sci USA*, 96:14193–14195 (1999)

Lessard et al, "Stage-Specific Expression of Polycomb Group Genes in Human Bone Marrow Cells", *Blood* 91:1216 (1998)

Li et al, "Both corepressor proteins SMRT and N-CoR exist in large protein complexes containing HDAC3", *EMBO J.* 19:4342–4350 (2000)

Lindquist et al, "Mutagen exposures and chromosome 3 aberrations in acute myelocytic leukemia", *Leukemia* 14:112–118 (2000)

Liu et al, "Chimeric mouse-human IgG1 antibody that can mediate lysis of cancer cells" *Proc Natl Acad Sci USA* 84:3439–3443 (1987)

Liu et al, "Siah-1 mediates a novel beta-catenin degradation pathway linking p53 to the adenomatous polyposis coli protein", *Mol Cell* 7:927–936 (2001)

Magli et al, "Transient nature of early haematopoietic spleen colonies", *Nature* 295:527–529 (1982)

Mao et al, "Identification of genes expressed in human CD34+hematopoietic stem/progenitor cells by expressed sequence tags and efficient full-length cDNA cloning", *Proc Nat Acad Sci USA* 95:8175 (1998)

Matsuzawa et al, "Siah-1, SIP, and Ebi Collaborate in a Novel Pathway for beta-Catenin Degradation Linked to p53 Responses", *Mol Cell* 7:915–926 (2001)

Meinkoth et al, "Hybridization of nucleic acids immobilized on solid supports", *Anal Biochem* 138:267–284 (1984)

Meyer et al, "Carboxyl-Truncated STAT5 beta Is Generated by a Nucleus-Associated Serine Protease in Early Hematopoietic Progenitors", *Blood* 91:1901–1908 (1998)

Morrison et al, "Chimeric human antibody molecules: mouse antigen-binding domains with human constant region domains". *Proc Natl Acad Sci USA* 81:6851–6855 (1984)

Munoz et al, "Absence of p53 mutation in 15 cases of myeloid malignancies with structural rearrangements of 3q" [letter], *Haematologica* 84:757–758 (1999)

Muramatsu et al, "Reversible integration of the dominant negative retinoid receptor gene for ex vivo expansion of hematopoietic stem/progenitor cells", *Biochem Biophys Res Commun* 285:891–896 (2001)

Muth et al, "Disruption of Genes Regulated During Hematopoietic Differentiation of Mouse Embryonic Stem Cells", *Dev Dyn* 212:277–283 (1998)

Neer et al, "The ancient regulatory-protein family of WD-repeat proteins", *Nature* 371, 297–300 (1994)

Neubauer et al, "Jak2 Deficiency Defines an Essential Developmental Checkpoint in Definitive Hematopoiesis", *Cell* 93:397–409 (1998)

Neuberger et al, "A hapten-specific chimaeric IgE antibody with human physiological effector function", *Nature* 314: 268–270 (1985)

Novak et al, "A new low density lipoprotein receptor homologue with 8 ligand binding repeats in brain of chicken and mouse", *J Biol Chem* 271:11732–11736 (1996)

Nowell et al, "Evidence for the Existence of Multipotential Lympho-hematopoietic Stem Cells in the Adult Rat", *J Cell Physiol* 75:151–158 (1969)

Ogilvy et al, "Promoter elements of vav drive transgene expression in vivo throughout the hematopoietic compartment" *Blood* 94:1855–1863 (1999)

Okuda et al, "Expression of a Knocked-In AML1-ETO Leukemia Gene Inhibits the Establishment of Normal Definite Hematopoiesis and Directly Generates Dysplastic Hematopoietic Progenitors", *Blood* 91:3134 (1998)

Orlic et al, "What defines a pluripotent hematopoietic stem cell (PHSC): Will the real PHSC please stand up", *Blood* 84:3991–3994 (1994)

Orlic et al, "Pluripotent hematopoietic stem cells contain high levels of mRNA for c-kit, GATA-2, p45 NF-E2, and c-myb and low levels or no mRNA for c-fms and the receptors for granulocyte colony-stimulating factor and interleukins 5 and 7", *Proc Natl Acad Sci USA* 92:4601–4605 (1995)

Pesole et al, "UTRdb: a specialized database of 5'- and 3'-untranslated regions of eukaryotic mRNAs", *Nucleic Acids Res* 26:192–195 (1998)

Pesole et al, "UTRdb and UTRsite: specialized databases of sequences and functional elements of 5' and 3' untranslated regions of eukaryotic mRNAs", *Nucleic Acids Res* 28:193–196 (2000)

Purton et al, "All-trans retinoic acid delays the differentiation of primitive hematopoietic precursors (lin-c-kit+Sca-1(+)) while enhancing the terminal maturation of committed granulocyte/monocyte progenitors", *Blood* 94:483–495 (1999)

Purton et al, "All-trans retinoic acid enhances the long-term repopulating activity of cultured hematopoietic stem cells", Blood 95:470–477Simon MC (1998) PU.1 and hematopoiesis: Lessons learned from gene targeting experiments", *Seminars in immunology* 10:111 (2000)

Rajagopalan et al, "Regulation of eukaryotic messenger RNA turnover", *Prog Nucleic Acid Res Mol Biol* 56:257–286 (1997)

Sahagan et al, "A genetically engineered murine/human chimeric antibody retains specificity for human tumor-associated antigen" *J Immunol* 137:1066–1074 (1986)

Salamov et al, "Recognition of 3'-processing sites of human mRNA precursors", *Comput Appl Biosci* 13:23–28 (1997)

Schwob et al, "The B-type cyclin kinase inhibitor p40SIC1 controls the G1 to S transition in *S. cerevisiae*", *Cell* 79:233–244 (1994)

Spangrude et al, "Purification and Characterization of mouse hematopoietic stem cells", *Science* 241:58–62 (1988)

Sun et al, "Chimeric antibody with human constant regions and mouse variable regions directed against carcinoma-associated antigen 17-1A", *Proc Natl Acad Sci USA* 84:214–218 (1987)

Terstappen et al, "Sequential generations of hematopoietic colonies derived from single nonlineage-committed CD34+CD38− progenitor cells", *Blood* 77:1218–1227 (1991)

Theise et al, "Derivation of Hepatocytes From Bone Marrow Cells in Mice After Radiation-Induced Myeloablation", *Hepatology* 31:235–240 (2000)

Welch et al, "The human Arp2/3 complex is composed of evolutionarily conserved subunits and is localized to cellular regions of dynamic actin filament assembly", *J Cell Biol* 138:375–384 (1997)

Wong et al, "Transcriptional repression by the SMRT-mSin3 corepressor: multiple interactions, multiple mechanisms, and a potential role for TFIIB", *Mol Cell Biol* 18:5500–5510 (1998)

Wu et al, "Evidence for a relationship between mouse hemopoietic stem cells and cells forming colonies in culture", *Proc Natl Acad Sci USA* 59:1209–215 (1968)

Xu et al, "Coactivator and corepressor complexes in nuclear receptor function", *Curr Opin Genet Dev* 9: 40–147 (1999)

Yang et al, "Human CD34+ cell EST database: Single-pass sequencing of 402 clones from a directional cDNA library", *Experimental Hematology* 24:605–612 (1996)

Yamazaki et al, "Elements of neural adhesion molecules and a yeast vacuolar protein sorting receptor are present in a novel mammalian low density lipoprotein receptor family member", *J Biol Chem* 271:24761–24768 (1996)

Yamazaki et al, "A novel member of the LDL receptor gene family with eleven binding repeats is structurally related to neural adhesion molecules and a yeast vacuolar protein sorting receptor", *J Atheroscler Thromb* 4:20–26 (1997)

Zhang et al, "Proteasomal regulation of nuclear receptor corepressor-mediated repression", *Genes Dev* 12:1775–1780 1998a)

Zhang et al, "Nf1 regulates hematopoietic progenitor cell growth and Ras signaling in response to multiple cytokines", *J Exp Med* 187:1893 (1998b)

What is claimed is:

1. An isolated polypeptide which interacts with, and has the activity of modulating the stability of transcriptional regulatory complexes that regulate nuclear hormone receptor activity, comprising an amino acid sequence of SEQ ID NO:2, or a fragment or variant thereof, wherein said fragment retains the activity of the polypeptide and said variant comprises an amino acid sequence having at least 90% sequence identity with SEQ ID NO:2 and has the activity of modulating the stability of transcriptional regulatory complexes that regulate nuclear hormone receptor activity.

2. The isolated polypeptide of claim 1 which comprises the amino acid sequence of SEQ ID NO:2.

3. The isolated polypeptide of claim 1, which comprises the amino acid sequence of SEQ ID NO:4.

4. The isolated polypeptide of claim 1, wherein said sequence identity is at least 95%.

5. The isolated polypeptide of claim 4, which comprises the amino acid sequence of SEQ ID NO:12.

6. A molecule which includes the antigen-binding portion of an antibody specific for the isolated polypeptide of claim 1.

7. The molecule of claim 6, which is selected from the group consisting of monoclonal antibody, humanized antibody and single-chain antibody.

* * * * *

SEQUENCE LISTING

```
<160> NUMBER OF SEQ ID NOS: 17

<210> SEQ ID NO 1
<211> LENGTH: 3885
<212> TYPE: DNA
<213> ORGANISM: Homo sapiens
<220> FEATURE:
<221> NAME/KEY: CDS
<222> LOCATION: (161)..(1705)
<223> OTHER INFORMATION:
<221> NAME/KEY: misc_feature
<222> LOCATION: (2487)..(2487)
<223> OTHER INFORMATION: n is a, c, g or t.
<221> NAME/KEY: misc_feature
<222> LOCATION: (2788)..(2788)
<223> OTHER INFORMATION: n is a, c, g or t.

<400> SEQUENCE: 1
ccgggagggg ggagcggcgt tggaggccac cgtttccagc atcaacaaca gcaacttgtg      60
attggcggtg accggatatt cagttgcaca tccccacatc aatgcactgc caatgggtta     120
tatcctgtgt tgtgacctca tggtttaagt gggaataaag atg agt ata agc agt      175
                                              Met Ser Ile Ser Ser
                                              1               5 gat gag gtc aac ttc ttg gta tat aga tac ttg caa gag tca gga ttt      223
Asp Glu Val Asn Phe Leu Val Tyr Arg Tyr Leu Gln Glu Ser Gly Phe
            10                  15                  20 tct cat tca gca ttt acc ttt ggt ata aaa agc cat atc agt cag tcc      271
Ser His Ser Ala Phe Thr Phe Gly Ile Lys Ser His Ile Ser Gln Ser
        25                  30                  35 aat ata aat ggt gcc ctc gtc cca ccc gct gca ttg att tct atc atc      319
Asn Ile Asn Gly Ala Leu Val Pro Pro Ala Ala Leu Ile Ser Ile Ile
    40                  45                  50 cag aaa ggt cta cag tat gta gaa gca gaa gtt agt att aat gag gat      367
Gln Lys Gly Leu Gln Tyr Val Glu Ala Glu Val Ser Ile Asn Glu Asp
55                  60                  65 ggt acc ttg ttt gat ggt cga cca ata gag tct ctg tcc ctg ata gat      415
Gly Thr Leu Phe Asp Gly Arg Pro Ile Glu Ser Leu Ser Leu Ile Asp
70                  75                  80                  85 gcc gta atg cct gat gta gta caa aca aga caa caa gct tat aga gat      463
Ala Val Met Pro Asp Val Val Gln Thr Arg Gln Gln Ala Tyr Arg Asp
                90                  95                 100 aag ctt gca cag caa cag gca gca gct gct gca gct gcc gca gct gca      511
Lys Leu Ala Gln Gln Gln Ala Ala Ala Ala Ala Ala Ala Ala Ala Ala
            105                 110                 115 gcc agc caa caa gga tct gca aaa aat gga gaa aac aca gca aat ggg      559
Ala Ser Gln Gln Gly Ser Ala Lys Asn Gly Glu Asn Thr Ala Asn Gly
        120                 125                 130 gag gag aat gga gca cat act ata gca aat aat cat act gat atg atg      607
Glu Glu Asn Gly Ala His Thr Ile Ala Asn Asn His Thr Asp Met Met
    135                 140                 145 gaa gtg gat ggg gat gtt gaa atc cct cct aat aaa gct gtt gtg ttg      655
```

-continued

| | | | | | | | | | | | | | | | | |
|---|---|---|---|---|---|---|---|---|---|---|---|---|---|---|---|---|
|Glu|Val|Asp|Gly|Asp|Val|Glu|Ile|Pro|Pro|Asn|Lys|Ala|Val|Val|Leu| |
|150| | | | |155| | | | |160| | | | |165| |

```
cgg ggc cat gaa tct gaa gtt ttt atc tgt gcc tgg aac cct gtt agt    703
Arg Gly His Glu Ser Glu Val Phe Ile Cys Ala Trp Asn Pro Val Ser
                170             175             180 gat ctc cta gca tca ggg tct gga gac tca aca gca aga ata tgg aat    751
Asp Leu Leu Ala Ser Gly Ser Gly Asp Ser Thr Ala Arg Ile Trp Asn
                185             190             195 ctt agt gag aac agc acc agt ggc tct aca cag tta gta ctt aga cat    799
Leu Ser Glu Asn Ser Thr Ser Gly Ser Thr Gln Leu Val Leu Arg His
                200             205             210 tgt ata cga gaa gga ggg caa gat gtt ccg agc aac aag gat gtc aca    847
Cys Ile Arg Glu Gly Gly Gln Asp Val Pro Ser Asn Lys Asp Val Thr
                215             220             225 tct cta gat tgg aat agt gaa ggt aca ctt cta gca act ggt tcc tat    895
Ser Leu Asp Trp Asn Ser Glu Gly Thr Leu Leu Ala Thr Gly Ser Tyr
230             235             240             245 gat ggg ttt gcc aga ata tgg act aaa gat ggt aac ctt gct agc acc    943
Asp Gly Phe Ala Arg Ile Trp Thr Lys Asp Gly Asn Leu Ala Ser Thr
                250             255             260 tta ggg cag cat aaa ggc cct ata ttt gca tta aaa tgg aat aag aaa    991
Leu Gly Gln His Lys Gly Pro Ile Phe Ala Leu Lys Trp Asn Lys Lys
                265             270             275 gga aat ttc atc cta agt gct gga gta gac aag act aca att att tgg   1039
Gly Asn Phe Ile Leu Ser Ala Gly Val Asp Lys Thr Thr Ile Ile Trp
                280             285             290 gac gca cat act ggt gaa gcc aag caa cag ttt cct ttt cat tca gca   1087
Asp Ala His Thr Gly Glu Ala Lys Gln Gln Phe Pro Phe His Ser Ala
295             300             305 cca gca ttg gat gtt gat tgg cag agc aac aac acc ttt gct tct tgt   1135
Pro Ala Leu Asp Val Asp Trp Gln Ser Asn Asn Thr Phe Ala Ser Cys
310             315             320             325 agt aca gat atg tgc att cat gtc tgt aaa tta gga caa gac aga cct   1183
Ser Thr Asp Met Cys Ile His Val Cys Lys Leu Gly Gln Asp Arg Pro
                330             335             340 att aaa aca ttc caa gga cat acg aat gaa gta aat gct atc aaa tgg   1231
Ile Lys Thr Phe Gln Gly His Thr Asn Glu Val Asn Ala Ile Lys Trp
                345             350             355 gac cca act ggc aat ctc ttg gcc tcc tgt tct gac gac atg act tta   1279
Asp Pro Thr Gly Asn Leu Leu Ala Ser Cys Ser Asp Asp Met Thr Leu
                360             365             370 aag ata tgg agt atg aaa caa gac aat tgt gtc cat gat ttg cag caa   1327
Lys Ile Trp Ser Met Lys Gln Asp Asn Cys Val His Asp Leu Gln Gln
375             380             385 cat aat aaa gaa att tat act atc aaa tgg agt cca aca gga cca ggg   1375
His Asn Lys Glu Ile Tyr Thr Ile Lys Trp Ser Pro Thr Gly Pro Gly
390             395             400             405 act aat aat cca aat gcc aac ctt atg tta gca agt gca tcc ttt gat   1423
Thr Asn Asn Pro Asn Ala Asn Leu Met Leu Ala Ser Ala Ser Phe Asp
                410             415             420 tct act gtt agg tta tgg gat gta gac cga ggg ata tgc atc cat acc   1471
Ser Thr Val Arg Leu Trp Asp Val Asp Arg Gly Ile Cys Ile His Thr
                425             430             435 ttg aca aaa cac caa gag cct gtg tac agt gta gct ttc agt cct gat   1519
Leu Thr Lys His Gln Glu Pro Val Tyr Ser Val Ala Phe Ser Pro Asp
                440             445             450 ggc agg tat ctg gca agt ggt tct ttt gac aaa tgt gta cac atc tgg   1567
Gly Arg Tyr Leu Ala Ser Gly Ser Phe Asp Lys Cys Val His Ile Trp
455             460             465
```

| | | | | | | | | | | | | | | |
|---|---|---|---|---|---|---|---|---|---|---|---|---|---|---|
| aac | acg | cag | aca | ggt | gct | cta | gtt | cac | agc | tat | agg | gga | aca | ggt | gga | 1615 |
| Asn | Thr | Gln | Thr | Gly | Ala | Leu | Val | His | Ser | Tyr | Arg | Gly | Thr | Gly | Gly |
| 470 | | | | 475 | | | | | 480 | | | | | 485 |

| | | | | | | | | | | | | | |
|---|---|---|---|---|---|---|---|---|---|---|---|---|---|
| ata | ttt | gaa | gtt | tgc | tgg | aat | gca | gca | gga | gac | aaa | gtt | gga | gcc | agt | 1663 |
| Ile | Phe | Glu | Val | Cys | Trp | Asn | Ala | Ala | Gly | Asp | Lys | Val | Gly | Ala | Ser |
| | | | | 490 | | | | | 495 | | | | | 500 |

| | | | | | | | | | | | | |
|---|---|---|---|---|---|---|---|---|---|---|---|---|
| gca | tca | gat | ggt | tca | gtt | tgt | gta | tta | gac | ctt | cgg | aaa | tag | 1705 |
| Ala | Ser | Asp | Gly | Ser | Val | Cys | Val | Leu | Asp | Leu | Arg | Lys |
| | | | 505 | | | | | 510 |

```
cgctactagt tggaagccat ggaccgacta tgaatgtgta catagccaaa atgagtgtcc      1765
ctgacccatg taatgttata gtcccacttg aaccatggcc agtccaatac agccaaatct      1825
aaaagaaata tacataca gtgtatataa acaaaattac accctgaaga tgacagagtt        1885
ttgtcacagc ttgtgaattc tgttcaccaa gtgctggaat ctaatctgct gtgcccctaa      1945
aatagcattt agaagttttg gatatgaaaa acagaagaga gaaaatatac attataaaag      2005
cagtacatac atgtaccagt ttttggatac taaatgacag ccttgtttct ccccttgaa       2065
tcagcagaca ccatggatta tattcttttt ttcccttcag tagtgagcag tttgtatgta      2125
cagagaaaat ggacttacaa aaacttgcag cagtagtttg ttcttgcttt aaaatttcgt      2185
ttttggttta gattatggat gcatgaagta agggagtgaa tcagtttctt gtttatattt      2245
ttttcacctt ttaaacaaaa aattctttaa aatattttaa tgcattcttt tgaagaggta      2305
gatgtttggt acattttatg gctcccagag catatattca gttggtgcat gttgtggaag      2365
ggggaattgg aaattaaatg gaaaacctat gactttggtc ctgtcaatct gtaagacaca      2425
tcagtaaaaa ggtattatgc tctgttggtt ttgttttttt gttttgcttt tttttttttt      2485
tncttttttg tttttttggtg atgtggctta aatgcaatag tttctttttt gggacatatt     2545
tctgccaatt aaagactaga agggcacaac ttttttttta attaccatag agaagataca      2605
ttaaaaaaaa tcttctgatg ttttgtagcc ataactaaat tatggtaaaa atgtgcacta      2665
ttgtgaaaag gagcaacgta gtttttgggtt ttttgttgtt tgtttgtttt gctttgtttt    2725
ttaagagatt aaaatgtttc tggataagga ttagcttctc gaagtgtcca tcattctgtg      2785
tanaagctta aatatgtaat gtaaccaaac tccagtatta aaaatctctc atgttgtttt     2845
ctttatacaa agcaagataa cggcatataa cactgccatt acatggcaaa atgtttgcta     2905
ccttagttta aaaacaatc tcaaacaaaa gacttgcttc aaggtgtttt taaatagcag      2965
tgattcagaa ttttttttaa tgaaagtata attgcactaa ccttcttcct gctgctctga     3025
ttctgcattt gtggtacttg tgactacgtt ttttcaaata tagatagatt taagctgcta    3085
atttttttt ttttagtaat cactactata tcatgtcttt tactctgttt ataatatcaa      3145
gtattttctt aaagatatag atattaaacc ttgtgctcat gcaacttaga gtaacatata     3205
cagacaaatg attgcatgag gccatgttta tatgtgtgac taataaggct tgtcatgatt    3265
aacataatcc aggtatgtca tttctgaaga gaatagtcat caaatttata tctcgaagat    3325
tttaattaag ggaattgctt attgtttgag cttagcaaat taataacact atttctgtca   3385
ctaattattt tgaggccttt tagtactaaa attttaacct gtgttctaag tagaaactga    3445
tttaacccaa gtaatgcagc tttgattgat ttcagcattc gttgctttgc tattttaca     3505
aaacagcatt gattgaagca gttttggtt ttactaaggt agggtagcat ttgctattgg     3565
taaagagaat aaatacactt aatttcacaa tacattgtta tatgtacccc agttgttgtt    3625
agtgggggact atgatactgt aataatattt ttaaaaattt acatcaagag aggcagtcat   3685
tcacgatggt tttgtgccag ctcttttttag ggttttggat cacattagag atatttagaa    3745
```

-continued

```
catattaccc tgtgacttac gtaggaaacc taatatgctg agtatctggc acttgaattc      3805
ctgcttttat tgctggaggt ccacatgtgt ggttgacctc tgttattgtt taaaaaaaaa      3865
aaaaaaaaaa aaaaaaaaaa                                                  3885
```

<210> SEQ ID NO 2
<211> LENGTH: 514
<212> TYPE: PRT
<213> ORGANISM: Homo sapiens
<220> FEATURE:

<400> SEQUENCE: 2

```
Met Ser Ile Ser Ser Asp Glu Val Asn Phe Leu Val Tyr Arg Tyr Leu
1               5                   10                  15

Gln Glu Ser Gly Phe Ser His Ser Ala Phe Thr Phe Gly Ile Lys Ser
            20                  25                  30

His Ile Ser Gln Ser Asn Ile Asn Gly Ala Leu Val Pro Pro Ala Ala
        35                  40                  45

Leu Ile Ser Ile Ile Gln Lys Gly Leu Gln Tyr Val Glu Ala Glu Val
    50                  55                  60

Ser Ile Asn Glu Asp Gly Thr Leu Phe Asp Gly Arg Pro Ile Glu Ser
65                  70                  75                  80

Leu Ser Leu Ile Asp Ala Val Met Pro Asp Val Val Gln Thr Arg Gln
                85                  90                  95

Gln Ala Tyr Arg Asp Lys Leu Ala Gln Gln Ala Ala Ala Ala Ala
            100                 105                 110

Ala Ala Ala Ala Ala Ser Gln Gln Gly Ser Ala Lys Asn Gly Glu
        115                 120                 125

Asn Thr Ala Asn Gly Glu Glu Asn Gly Ala His Thr Ile Ala Asn Asn
    130                 135                 140

His Thr Asp Met Met Glu Val Asp Gly Asp Val Glu Ile Pro Pro Asn
145                 150                 155                 160

Lys Ala Val Val Leu Arg Gly His Glu Ser Glu Val Phe Ile Cys Ala
                165                 170                 175

Trp Asn Pro Val Ser Asp Leu Leu Ala Ser Gly Ser Gly Asp Ser Thr
            180                 185                 190

Ala Arg Ile Trp Asn Leu Ser Glu Asn Ser Thr Ser Gly Ser Thr Gln
        195                 200                 205

Leu Val Leu Arg His Cys Ile Arg Glu Gly Gly Gln Asp Val Pro Ser
    210                 215                 220

Asn Lys Asp Val Thr Ser Leu Asp Trp Asn Ser Glu Gly Thr Leu Leu
225                 230                 235                 240

Ala Thr Gly Ser Tyr Asp Gly Phe Ala Arg Ile Trp Thr Lys Asp Gly
                245                 250                 255

Asn Leu Ala Ser Thr Leu Gly Gln His Lys Gly Pro Ile Phe Ala Leu
            260                 265                 270

Lys Trp Asn Lys Lys Gly Asn Phe Ile Leu Ser Ala Gly Val Asp Lys
        275                 280                 285

Thr Thr Ile Ile Trp Asp Ala His Thr Gly Glu Ala Lys Gln Gln Phe
    290                 295                 300

Pro Phe His Ser Ala Pro Ala Leu Asp Val Asp Trp Gln Ser Asn Asn
305                 310                 315                 320

Thr Phe Ala Ser Cys Ser Thr Asp Met Cys Ile His Val Cys Lys Leu
                325                 330                 335
```

-continued

```
Gly Gln Asp Arg Pro Ile Lys Thr Phe Gln Gly His Thr Asn Glu Val
            340                 345                 350
Asn Ala Ile Lys Trp Asp Pro Thr Gly Asn Leu Leu Ala Ser Cys Ser
            355                 360                 365
Asp Asp Met Thr Leu Lys Ile Trp Ser Met Lys Gln Asp Asn Cys Val
        370                 375                 380
His Asp Leu Gln Gln His Asn Lys Glu Ile Tyr Thr Ile Lys Trp Ser
385                 390                 395                 400
Pro Thr Gly Pro Gly Thr Asn Asn Pro Asn Ala Asn Leu Met Leu Ala
                405                 410                 415
Ser Ala Ser Phe Asp Ser Thr Val Arg Leu Trp Asp Val Asp Arg Gly
                420                 425                 430
Ile Cys Ile His Thr Leu Thr Lys His Gln Glu Pro Val Tyr Ser Val
            435                 440                 445
Ala Phe Ser Pro Asp Gly Arg Tyr Leu Ala Ser Gly Ser Phe Asp Lys
        450                 455                 460
Cys Val His Ile Trp Asn Thr Gln Thr Gly Ala Leu Val His Ser Tyr
465                 470                 475                 480
Arg Gly Thr Gly Gly Ile Phe Glu Val Cys Trp Asn Ala Ala Gly Asp
                485                 490                 495
Lys Val Gly Ala Ser Ala Ser Asp Gly Ser Val Cys Val Leu Asp Leu
                500                 505                 510
Arg Lys
```

```
<210> SEQ ID NO 3
<211> LENGTH: 2078
<212> TYPE: DNA
<213> ORGANISM: Homo sapiens
<220> FEATURE:
<221> NAME/KEY: CDS
<222> LOCATION: (161)..(1705)
<223> OTHER INFORMATION:

<400> SEQUENCE: 3
```

```
ccgggagggg ggagcggcgt tggaggccac cgtttccagc atcaacaaca gcaacttgtg      60
attggcggtg accgatatt  cagttgcaca tccccacatc aatgcactgc caatgggtta    120
tatcctgtgt tgtgacctca tggtttaagt gggaataaag atg agt ata agc agt     175
                                            Met Ser Ile Ser Ser
                                              1               5 gat gag gtc aac ttc ttg gta tat aga tac ttg caa gag tca gga ttt    223
Asp Glu Val Asn Phe Leu Val Tyr Arg Tyr Leu Gln Glu Ser Gly Phe
             10                  15                  20 tct cat tca gca ttt acc ttt ggt ata aaa agc cat atc agt cag tcc    271
Ser His Ser Ala Phe Thr Phe Gly Ile Lys Ser His Ile Ser Gln Ser
         25                  30                  35 aat ata aat ggt gcc ctc gtc cca ccc gct gca ttg att tct atc atc    319
Asn Ile Asn Gly Ala Leu Val Pro Pro Ala Ala Leu Ile Ser Ile Ile
     40                  45                  50 cag aaa ggt cta cag tat gta gaa gca gaa gtt agt att aat gag gat    367
Gln Lys Gly Leu Gln Tyr Val Glu Ala Glu Val Ser Ile Asn Glu Asp
 55                  60                  65 ggt acc ttg ttt gat ggt cga cca ata gag tct ctg tcc ctg ata gat    415
Gly Thr Leu Phe Asp Gly Arg Pro Ile Glu Ser Leu Ser Leu Ile Asp
 70                  75                  80                  85 gcc gta atg cct gat gta gta caa aca aga caa caa gct tat aga gat    463
Ala Val Met Pro Asp Val Val Gln Thr Arg Gln Gln Ala Tyr Arg Asp
             90                  95                 100
```

-continued

```
aag ctt gca cag caa cag gca gca gct gct gca gct gcc gct gca      511
Lys Leu Ala Gln Gln Gln Ala Ala Ala Ala Ala Ala Ala Ala Ala
        105                 110                 115 gcc agc caa caa gga tct gca aaa aat gga gaa aac aca gca aat ggg  559
Ala Ser Gln Gln Gly Ser Ala Lys Asn Gly Glu Asn Thr Ala Asn Gly
    120                 125                 130 gag gag aat gga gca cat act ata gca aat aat cat act gat atg atg  607
Glu Glu Asn Gly Ala His Thr Ile Ala Asn Asn His Thr Asp Met Met
135                 140                 145 gaa gtg gat ggg gat gtt gaa atc cct cct aat aaa gct gtt gtg ttg  655
Glu Val Asp Gly Asp Val Glu Ile Pro Pro Asn Lys Ala Val Val Leu
150                 155                 160                 165 cgg ggc cat gaa tct gaa gtt ttt atc tgt gcc tgg aac cct gtt agt  703
Arg Gly His Glu Ser Glu Val Phe Ile Cys Ala Trp Asn Pro Val Ser
                170                 175                 180 gat ctc cta gca tca ggg tct gga gac tca aca gca aga ata tgg aat  751
Asp Leu Leu Ala Ser Gly Ser Gly Asp Ser Thr Ala Arg Ile Trp Asn
            185                 190                 195 ctt agt gag aac agc acc agt ggc tct aca cag tta gta ctt aga cat  799
Leu Ser Glu Asn Ser Thr Ser Gly Ser Thr Gln Leu Val Leu Arg His
        200                 205                 210 tgt ata cga gaa gga ggg caa gat gtt ccg agc aac aag gat gtc aca  847
Cys Ile Arg Glu Gly Gly Gln Asp Val Pro Ser Asn Lys Asp Val Thr
    215                 220                 225 tct cta gat tgg aat agt gaa ggt aca ctt cta gca act ggt tcc tat  895
Ser Leu Asp Trp Asn Ser Glu Gly Thr Leu Leu Ala Thr Gly Ser Tyr
230                 235                 240                 245 gat ggg ttt gcc aga ata tgg act aaa gat ggt aac ctt gct agc acc  943
Asp Gly Phe Ala Arg Ile Trp Thr Lys Asp Gly Asn Leu Ala Ser Thr
                250                 255                 260 tta ggg cag cat aaa ggc cct ata ttt gca tta aaa tgg aat aag aaa  991
Leu Gly Gln His Lys Gly Pro Ile Phe Ala Leu Lys Trp Asn Lys Lys
            265                 270                 275 gga aat ttc atc cta agt gct gga gta gac aag act aca att att tgg  1039
Gly Asn Phe Ile Leu Ser Ala Gly Val Asp Lys Thr Thr Ile Ile Trp
        280                 285                 290 gac gca cat act ggt gaa gcc aag caa cag ttt cct ttt cat tca gca  1087
Asp Ala His Thr Gly Glu Ala Lys Gln Gln Phe Pro Phe His Ser Ala
    295                 300                 305 cca gca ttg gat gtt gat tgg cag agc aac aac acc ttt gct tct tgt  1135
Pro Ala Leu Asp Val Asp Trp Gln Ser Asn Asn Thr Phe Ala Ser Cys
310                 315                 320                 325 agt aca gat atg tgc att cat gtc tgt aaa tta gga caa gac aga cct  1183
Ser Thr Asp Met Cys Ile His Val Cys Lys Leu Gly Gln Asp Arg Pro
                330                 335                 340 att aaa aca ttc caa gga cat acg aat gaa gta aat gct atc aaa tgg  1231
Ile Lys Thr Phe Gln Gly His Thr Asn Glu Val Asn Ala Ile Lys Trp
            345                 350                 355 gac cca act ggg aat ctc ttg gcc tcc tgt tct gac gac atg act tta  1279
Asp Pro Thr Gly Asn Leu Leu Ala Ser Cys Ser Asp Asp Met Thr Leu
        360                 365                 370 aag ata tgg agt atg aaa caa gac aat tgt gtc cat gat ttg cag caa  1327
Lys Ile Trp Ser Met Lys Gln Asp Asn Cys Val His Asp Leu Gln Gln
    375                 380                 385 cat aat aaa gaa att tat act atc aaa tgg agt cca aca gga cca ggg  1375
His Asn Lys Glu Ile Tyr Thr Ile Lys Trp Ser Pro Thr Gly Pro Gly
390                 395                 400                 405 act aat aat cca aat gcc aac ctt atg tta gca agt gca tcc ttt gat  1423
Thr Asn Asn Pro Asn Ala Asn Leu Met Leu Ala Ser Ala Ser Phe Asp
                410                 415                 420
```

-continued

```
tct act gtt agg tta tgg gat gta gac cga ggg ata tgc atc cat acc      1471
Ser Thr Val Arg Leu Trp Asp Val Asp Arg Gly Ile Cys Ile His Thr
            425                 430                 435 ttg aca aaa cac caa gag cct gtg tac agt gta gct ttc agt cct gat      1519
Leu Thr Lys His Gln Glu Pro Val Tyr Ser Val Ala Phe Ser Pro Asp
        440                 445                 450 ggc agg tat ctg gca agt ggt tct ttt gac aaa tgt gta cac atc tgg      1567
Gly Arg Tyr Leu Ala Ser Gly Ser Phe Asp Lys Cys Val His Ile Trp
    455                 460                 465 aac acg cag gta tgt ctt cat tat tta aat ggt caa gtg ctc tta aat      1615
Asn Thr Gln Val Cys Leu His Tyr Leu Asn Gly Gln Val Leu Leu Asn
470                 475                 480                 485 tta ggt aga agc att tgc cta tac act ctg cct cac cat ttg gtt gtc      1663
Leu Gly Arg Ser Ile Cys Leu Tyr Thr Leu Pro His His Leu Val Val
                490                 495                 500 att cct ctt gtg gca tta att gaa tta ttg gtt tta aaa taa              1705
Ile Pro Leu Val Ala Leu Ile Glu Leu Leu Val Leu Lys
                505                 510 gatagaaact aatggaagtt atatctttat ggagactgga attttgaaat ggattttgat    1765
catttgtttt attatttatt attgtattct tttgtttttt tccaacggtt ttgcagatat    1825
cagatgtgaa tgtttaagat gtatttattt agataaatga cagattttat ttttcaaaat   1885
agttgtctcc gaaggagcta tatgtgagca gtaaaagtca aggaccaga ttttatggct    1945 gaatgcaata atttatgaga aagaaactta caactacatt accttttcag gtaagtatgt   2005
atggtgtttc aaagattctt agaagtggag aaaacagtct ggtgctttca attttttaaa   2065
tcttctcaat ggt                                                       2078
```

<210> SEQ ID NO 4
<211> LENGTH: 514
<212> TYPE: PRT
<213> ORGANISM: Homo sapiens

<400> SEQUENCE: 4

```
Met Ser Ile Ser Ser Asp Glu Val Asn Phe Leu Val Tyr Arg Tyr Leu
1               5                   10                  15

Gln Glu Ser Gly Phe Ser His Ser Ala Phe Thr Phe Gly Ile Lys Ser
            20                  25                  30

His Ile Ser Gln Ser Asn Ile Asn Gly Ala Leu Val Pro Pro Ala Ala
        35                  40                  45

Leu Ile Ser Ile Ile Gln Lys Gly Leu Gln Tyr Val Glu Ala Glu Val
    50                  55                  60

Ser Ile Asn Glu Asp Gly Thr Leu Phe Asp Gly Arg Pro Ile Glu Ser
65                  70                  75                  80

Leu Ser Leu Ile Asp Ala Val Met Pro Asp Val Val Gln Thr Arg Gln
                85                  90                  95

Gln Ala Tyr Arg Asp Lys Leu Ala Gln Gln Ala Ala Ala Ala
            100                 105                 110

Ala Ala Ala Ala Ala Ser Gln Gln Gly Ser Ala Lys Asn Gly Glu
        115                 120                 125

Asn Thr Ala Asn Gly Glu Glu Asn Gly Ala His Thr Ile Ala Asn Asn
    130                 135                 140

His Thr Asp Met Met Glu Val Asp Gly Asp Val Glu Ile Pro Pro Asn
145                 150                 155                 160

Lys Ala Val Val Leu Arg Gly His Glu Ser Glu Val Phe Ile Cys Ala
                165                 170                 175
```

Trp Asn Pro Val Ser Asp Leu Leu Ala Ser Gly Ser Gly Asp Ser Thr
            180                 185                 190

Ala Arg Ile Trp Asn Leu Ser Glu Asn Ser Thr Ser Gly Ser Thr Gln
        195                 200                 205

Leu Val Leu Arg His Cys Ile Arg Glu Gly Gly Gln Asp Val Pro Ser
        210                 215                 220

Asn Lys Asp Val Thr Ser Leu Asp Trp Asn Ser Glu Gly Thr Leu Leu
225                 230                 235                 240

Ala Thr Gly Ser Tyr Asp Gly Phe Ala Arg Ile Trp Thr Lys Asp Gly
                245                 250                 255

Asn Leu Ala Ser Thr Leu Gly Gln His Lys Gly Pro Ile Phe Ala Leu
            260                 265                 270

Lys Trp Asn Lys Lys Gly Asn Phe Ile Leu Ser Ala Gly Val Asp Lys
        275                 280                 285

Thr Thr Ile Ile Trp Asp Ala His Thr Gly Glu Ala Lys Gln Gln Phe
        290                 295                 300

Pro Phe His Ser Ala Pro Ala Leu Asp Val Asp Trp Gln Ser Asn Asn
305                 310                 315                 320

Thr Phe Ala Ser Cys Ser Thr Asp Met Cys Ile His Val Cys Lys Leu
                325                 330                 335

Gly Gln Asp Arg Pro Ile Lys Thr Phe Gln Gly His Thr Asn Glu Val
            340                 345                 350

Asn Ala Ile Lys Trp Asp Pro Thr Gly Asn Leu Leu Ala Ser Cys Ser
        355                 360                 365

Asp Asp Met Thr Leu Lys Ile Trp Ser Met Lys Gln Asp Asn Cys Val
        370                 375                 380

His Asp Leu Gln Gln His Asn Lys Glu Ile Tyr Thr Ile Lys Trp Ser
385                 390                 395                 400

Pro Thr Gly Pro Gly Thr Asn Asn Pro Asn Ala Asn Leu Met Leu Ala
                405                 410                 415

Ser Ala Ser Phe Asp Ser Thr Val Arg Leu Trp Asp Val Asp Arg Gly
            420                 425                 430

Ile Cys Ile His Thr Leu Thr Lys His Gln Glu Pro Val Tyr Ser Val
        435                 440                 445

Ala Phe Ser Pro Asp Gly Arg Tyr Leu Ala Ser Gly Ser Phe Asp Lys
        450                 455                 460

Cys Val His Ile Trp Asn Thr Gln Val Cys Leu His Tyr Leu Asn Gly
465                 470                 475                 480

Gln Val Leu Leu Asn Leu Gly Arg Ser Ile Cys Leu Tyr Thr Leu Pro
                485                 490                 495

His His Leu Val Val Ile Pro Leu Val Ala Leu Ile Glu Leu Leu Val
            500                 505                 510

Leu Lys

<210> SEQ ID NO 5
<211> LENGTH: 20
<212> TYPE: DNA
<213> ORGANISM: Artificial Sequence
<220> FEATURE:
<223> OTHER INFORMATION: Synthetic

<400> SEQUENCE: 5
agggaatgta acccttctca                                            20

```
<210> SEQ ID NO 6
<211> LENGTH: 20
<212> TYPE: DNA
<213> ORGANISM: Artificial Sequence
<220> FEATURE:
<223> OTHER INFORMATION: Synthetic

<400> SEQUENCE: 6
tcttactaga tgcagtgacc                                                    20

<210> SEQ ID NO 7
<211> LENGTH: 21
<212> TYPE: DNA
<213> ORGANISM: Artificial Sequence
<220> FEATURE:
<223> OTHER INFORMATION: Synthetic

<400> SEQUENCE: 7
gatgagtata agcagtgatg t                                                  21

<210> SEQ ID NO 8
<211> LENGTH: 29
<212> TYPE: DNA
<213> ORGANISM: Artificial Sequence
<220> FEATURE:
<223> OTHER INFORMATION: Synthetic

<400> SEQUENCE: 8 ctattttgt tctttccgaa ggtctaata                                           29

<210> SEQ ID NO 9
<211> LENGTH: 21
<212> TYPE: DNA
<213> ORGANISM: Artificial Sequence
<220> FEATURE:
<223> OTHER INFORMATION: Synthetic

<400> SEQUENCE: 9
caacagagct tcactttacc c                                                  21

<210> SEQ ID NO 10
<211> LENGTH: 19
<212> TYPE: DNA
<213> ORGANISM: Artificial Sequence
<220> FEATURE:
<223> OTHER INFORMATION: Synthetic

<400> SEQUENCE: 10
ctagggatgg tttccatga                                                     19

<210> SEQ ID NO 11
<211> LENGTH: 1853
<212> TYPE: DNA
<213> ORGANISM: Mus musculus
<220> FEATURE:
<221> NAME/KEY: CDS
<222> LOCATION: (197)..(1741)
<223> OTHER INFORMATION:

<400> SEQUENCE: 11
tagctccagc ctctgcatca gctcctgctt tcttacctga gttccagtcc tgacttcctt        60
ggtgatgaac aacaatgtgg aagtcttcag taacttgtga ttggtggttg ctatccagt       120 tgttcatcct cacatcaatg cactgccaat gggttatgtc ctgtgttgtg acctcatggt      180
ttaagtggga ataaag atg agt ata agc agt gat gag gtc aac ttc ttg gta     232
                 Met Ser Ile Ser Ser Asp Glu Val Asn Phe Leu Val
```

-continued

```
            1                       5                      10
tat agg tac ttg caa gag tca gga ttt tct cat tct gcg ttt acc ttt        280
Tyr Arg Tyr Leu Gln Glu Ser Gly Phe Ser His Ser Ala Phe Thr Phe
         15                  20                  25 ggt ata gag agc cat ata agt cag tcc aac ata aat ggt gcc ctg gtt        328
Gly Ile Glu Ser His Ile Ser Gln Ser Asn Ile Asn Gly Ala Leu Val
     30                  35                  40 cca ccc gct gca ctc atc tct atc atc cag aaa ggc ctg cag tat gta        376
Pro Pro Ala Ala Leu Ile Ser Ile Ile Gln Lys Gly Leu Gln Tyr Val
45                  50                  55                  60 gag gca gaa gtt agc ata aat gag gat ggc acc tta ttt gat ggt cga        424
Glu Ala Glu Val Ser Ile Asn Glu Asp Gly Thr Leu Phe Asp Gly Arg
                 65                  70                  75 ccc atc gag tct ctg tcc ctg ata gat gct gtt atg ccc gat gta gtc        472
Pro Ile Glu Ser Leu Ser Leu Ile Asp Ala Val Met Pro Asp Val Val
                     80                  85                  90 caa aca aga caa caa gcc tac aga gac aag ctt gca cag cag cat gca        520
Gln Thr Arg Gln Gln Ala Tyr Arg Asp Lys Leu Ala Gln Gln His Ala
             95                 100                 105 gcc gca gcc gct gcc gct gct gcc gcc act aac cag caa gga tct gca        568
Ala Ala Ala Ala Ala Ala Ala Ala Thr Asn Gln Gln Gly Ser Ala
        110                 115                 120 aaa aat gga gag aat aca gca aat ggg gag gag aat gga gca cat acc        616
Lys Asn Gly Glu Asn Thr Ala Asn Gly Glu Glu Asn Gly Ala His Thr
125                 130                 135                 140 atc gca aat aat cac act gac atg atg gaa gta gat ggg gat gtg gaa        664
Ile Ala Asn Asn His Thr Asp Met Met Glu Val Asp Gly Asp Val Glu
                145                 150                 155 atc cct tcc aat aaa gcg gtt gtg ctt cgg ggc cat gaa tct gaa gtt        712
Ile Pro Ser Asn Lys Ala Val Val Leu Arg Gly His Glu Ser Glu Val
                    160                 165                 170 ttc atc tgt gcc tgg aac cct gtt agt gat ctc ctg gta tca ggg tct        760
Phe Ile Cys Ala Trp Asn Pro Val Ser Asp Leu Leu Val Ser Gly Ser
            175                 180                 185 gga gac tcc acg gca aga atc tgg aac ctc agt gag aac agc acg agt        808
Gly Asp Ser Thr Ala Arg Ile Trp Asn Leu Ser Glu Asn Ser Thr Ser
        190                 195                 200 ggc cct acg cag ctc gtg ctt aga cac tgc ata cgg gaa gga ggg cag        856
Gly Pro Thr Gln Leu Val Leu Arg His Cys Ile Arg Glu Gly Gly Gln
205                 210                 215                 220 gac gtg ccc agt aac aag gat gtc acg tct cta gat tgg aat agt gaa        904
Asp Val Pro Ser Asn Lys Asp Val Thr Ser Leu Asp Trp Asn Ser Glu
                225                 230                 235 ggt aca ctt cta gca act ggg tca tat gat gga ttt gcc aga ata tgg        952
Gly Thr Leu Leu Ala Thr Gly Ser Tyr Asp Gly Phe Ala Arg Ile Trp
            240                 245                 250 act aaa gat ggt aat ctt gcc agc acc ttg ggg cag cat aaa ggt cct       1000
Thr Lys Asp Gly Asn Leu Ala Ser Thr Leu Gly Gln His Lys Gly Pro
        255                 260                 265 ata ttt gca tta aag tgg aat aag aaa gga aat ttc atc cta agt gct       1048
Ile Phe Ala Leu Lys Trp Asn Lys Lys Gly Asn Phe Ile Leu Ser Ala
270                 275                 280 ggc gta gat aag acc acc atc att tgg gat gcg cat act ggt gaa gcc       1096
Gly Val Asp Lys Thr Thr Ile Ile Trp Asp Ala His Thr Gly Glu Ala
285                 290                 295                 300 aag cag cag ttt cct ttc cat tca gcc cca gca ttg gat gtt gac tgg       1144
Lys Gln Gln Phe Pro Phe His Ser Ala Pro Ala Leu Asp Val Asp Trp
                305                 310                 315 cag agc aac aac acc ttt gca tct tgt agt aca gat atg tgc att cac       1192
Gln Ser Asn Asn Thr Phe Ala Ser Cys Ser Thr Asp Met Cys Ile His
```

```
              Gln Ser Asn Asn Thr Phe Ala Ser Cys Ser Thr Asp Met Cys Ile His
                              320                 325                 330 gtc tgc aaa tta gga caa gac aga cct atc aaa aca ttc cag gga cac        1240
Val Cys Lys Leu Gly Gln Asp Arg Pro Ile Lys Thr Phe Gln Gly His
            335                 340                 345 acg aat gaa gta aat gct atc aaa tgg gac cca act ggc aat ctc cta        1288
Thr Asn Glu Val Asn Ala Ile Lys Trp Asp Pro Thr Gly Asn Leu Leu
350                 355                 360 gcc tcc tgt tca gat gac atg aca ttg aag atc tgg agt atg aag caa        1336
Ala Ser Cys Ser Asp Asp Met Thr Leu Lys Ile Trp Ser Met Lys Gln
365                 370                 375                 380 gat aac tgt gtc cat gat ttg caa gca cat aat aaa gaa att tat act        1384
Asp Asn Cys Val His Asp Leu Gln Ala His Asn Lys Glu Ile Tyr Thr
                385                 390                 395 att aag tgg agt cca aca gga cca ggg aca aat aat cca aat gcc aac        1432
Ile Lys Trp Ser Pro Thr Gly Pro Gly Thr Asn Asn Pro Asn Ala Asn
            400                 405                 410 ctt atg cta gca agt gca tcc ttt gat tct aca gtt agg tta tgg gac        1480
Leu Met Leu Ala Ser Ala Ser Phe Asp Ser Thr Val Arg Leu Trp Asp
        415                 420                 425 gta gac aga ggg att tgc atc cat act ttg aca aaa cat caa gag ccc        1528
Val Asp Arg Gly Ile Cys Ile His Thr Leu Thr Lys His Gln Glu Pro
    430                 435                 440 gtg tac agt gtg gct ttt agt cct gat ggc agg tat ctg gca agt ggt        1576
Val Tyr Ser Val Ala Phe Ser Pro Asp Gly Arg Tyr Leu Ala Ser Gly
445                 450                 455                 460 tct ttt gac aag tgt gtg cac atc tgg aac aca cag aca ggt gct cta        1624
Ser Phe Asp Lys Cys Val His Ile Trp Asn Thr Gln Thr Gly Ala Leu
                465                 470                 475 gtt cac agt tac agg gga aca ggt gga att ttt gaa gtt tgc tgg aac        1672
Val His Ser Tyr Arg Gly Thr Gly Gly Ile Phe Glu Val Cys Trp Asn
            480                 485                 490 gca gca gga gac aaa gtt gga gcc agt gct tcg gac ggt tca gtt tgt        1720
Ala Ala Gly Asp Lys Val Gly Ala Ser Ala Ser Asp Gly Ser Val Cys
        495                 500                 505 gtc tta gac ctt cgg aaa tag cgttactagt tggaagccat ggaccgacta           1771
Val Leu Asp Leu Arg Lys
    510 tgaatgtgta catagccaca agactatccc tgacccatat actgctatag tcccacttga     1831 accatggcca gtccactaca gc                                               1853

<210> SEQ ID NO 12
<211> LENGTH: 514
<212> TYPE: PRT
<213> ORGANISM: Mus musculus

<400> SEQUENCE: 12

Met Ser Ile Ser Ser Asp Glu Val Asn Phe Leu Val Tyr Arg Tyr Leu
1               5                   10                  15

Gln Glu Ser Gly Phe Ser His Ser Ala Phe Thr Phe Gly Ile Glu Ser
                20                  25                  30

His Ile Ser Gln Ser Asn Ile Asn Gly Ala Leu Val Pro Ala Ala
            35                  40                  45

Leu Ile Ser Ile Ile Gln Lys Gly Leu Gln Tyr Val Glu Ala Glu Val
        50                  55                  60

Ser Ile Asn Glu Asp Gly Thr Leu Phe Asp Gly Arg Pro Ile Glu Ser
65                  70                  75                  80

Leu Ser Leu Ile Asp Ala Val Met Pro Asp Val Val Gln Thr Arg Gln
```

-continued

```
                 85                  90                  95
Gln Ala Tyr Arg Asp Lys Leu Ala Gln Gln His Ala Ala Ala Ala
                100                 105                 110
Ala Ala Ala Ala Ala Thr Asn Gln Gln Gly Ser Ala Lys Asn Gly Glu
                115                 120                 125
Asn Thr Ala Asn Gly Glu Glu Asn Gly Ala His Thr Ile Ala Asn Asn
            130                 135                 140
His Thr Asp Met Met Glu Val Asp Gly Asp Val Glu Ile Pro Ser Asn
145                 150                 155                 160
Lys Ala Val Val Leu Arg Gly His Glu Ser Glu Val Phe Ile Cys Ala
                165                 170                 175
Trp Asn Pro Val Ser Asp Leu Leu Val Ser Gly Ser Gly Asp Ser Thr
            180                 185                 190
Ala Arg Ile Trp Asn Leu Ser Glu Asn Ser Thr Ser Gly Pro Thr Gln
            195                 200                 205
Leu Val Leu Arg His Cys Ile Arg Glu Gly Gly Gln Asp Val Pro Ser
        210                 215                 220
Asn Lys Asp Val Thr Ser Leu Asp Trp Asn Ser Glu Gly Thr Leu Leu
225                 230                 235                 240
Ala Thr Gly Ser Tyr Asp Gly Phe Ala Arg Ile Trp Thr Lys Asp Gly
                245                 250                 255
Asn Leu Ala Ser Thr Leu Gly Gln His Lys Gly Pro Ile Phe Ala Leu
                260                 265                 270
Lys Trp Asn Lys Lys Gly Asn Phe Ile Leu Ser Ala Gly Val Asp Lys
            275                 280                 285
Thr Thr Ile Ile Trp Asp Ala His Thr Gly Glu Ala Lys Gln Gln Phe
        290                 295                 300
Pro Phe His Ser Ala Pro Ala Leu Asp Val Asp Trp Gln Ser Asn Asn
305                 310                 315                 320
Thr Phe Ala Ser Cys Ser Thr Asp Met Cys Ile His Val Cys Lys Leu
                325                 330                 335
Gly Gln Asp Arg Pro Ile Lys Thr Phe Gln Gly His Thr Asn Glu Val
            340                 345                 350
Asn Ala Ile Lys Trp Asp Pro Thr Gly Asn Leu Leu Ala Ser Cys Ser
            355                 360                 365
Asp Asp Met Thr Leu Lys Ile Trp Ser Met Lys Gln Asp Asn Cys Val
        370                 375                 380
His Asp Leu Gln Ala His Asn Lys Glu Ile Tyr Thr Ile Lys Trp Ser
385                 390                 395                 400
Pro Thr Gly Pro Gly Thr Asn Asn Pro Asn Ala Asn Leu Met Leu Ala
                405                 410                 415
Ser Ala Ser Phe Asp Ser Thr Val Arg Leu Trp Asp Val Asp Arg Gly
                420                 425                 430
Ile Cys Ile His Thr Leu Thr Lys His Gln Glu Pro Val Tyr Ser Val
            435                 440                 445
Ala Phe Ser Pro Asp Gly Arg Tyr Leu Ala Ser Gly Ser Phe Asp Lys
            450                 455                 460
Cys Val His Ile Trp Asn Thr Gln Thr Gly Ala Leu Val His Ser Tyr
465                 470                 475                 480
Arg Gly Thr Gly Gly Ile Phe Glu Val Cys Trp Asn Ala Ala Gly Asp
                485                 490                 495
Lys Val Gly Ala Ser Ala Ser Asp Gly Ser Val Cys Val Leu Asp Leu
            500                 505                 510
```

Arg Lys

<210> SEQ ID NO 13
<211> LENGTH: 10
<212> TYPE: PRT
<213> ORGANISM: Artificial Sequence
<220> FEATURE:
<223> OTHER INFORMATION: Synthetic

<400> SEQUENCE: 13

Cys Gly Val Ser His Gln Asn Pro Ser Lys
1               5                   10

<210> SEQ ID NO 14
<211> LENGTH: 24
<212> TYPE: DNA
<213> ORGANISM: Artificial Sequence
<220> FEATURE:
<223> OTHER INFORMATION: Synthetic

<400> SEQUENCE: 14
caagcttata gagataagct tgca                                              24

<210> SEQ ID NO 15
<211> LENGTH: 24
<212> TYPE: DNA
<213> ORGANISM: Artificial Sequence
<220> FEATURE:
<223> OTHER INFORMATION: Synthetic

<400> SEQUENCE: 15
caggcttata gagataaact tgca                                              24

<210> SEQ ID NO 16
<211> LENGTH: 22
<212> TYPE: DNA
<213> ORGANISM: Artificial Sequence
<220> FEATURE:
<223> OTHER INFORMATION: Synthetic

<400> SEQUENCE: 16
gtaagactct ccaactccca at                                                22

<210> SEQ ID NO 17
<211> LENGTH: 44
<212> TYPE: PRT
<213> ORGANISM: Artificial Sequence
<220> FEATURE:
<223> OTHER INFORMATION: Synthetic

<400> SEQUENCE: 17

Thr Gln Thr Gly Ala Leu Val His Ser Tyr Arg Gly Thr Gly Gly Ile
1               5                   10                  15

Phe Glu Val Cys Trp Asn Ala Cys Ala Gly Asp Lys Val Gly Ala Ser
            20                  25                  30

Ala Ser Asp Gly Ser Val Cys Val Leu Asp Leu Arg
        35                  40